US008790678B2

(12) United States Patent
Elbert et al.

(10) Patent No.: US 8,790,678 B2
(45) Date of Patent: Jul. 29, 2014

(54) BIOMATERIALS HAVING NANOSCALE LAYERS AND COATINGS

(75) Inventors: Donald Elbert, Clayton, MO (US); Megan Kaneda, St. Louis, MO (US); Evan Scott, University City, MO (US); Brad Wacker, St. Louis, MO (US); Shannon Alford, Cambridge, MA (US)

(73) Assignee: Washington University, St. Louis, MO (US)

( * ) Notice: Subject to any disclaimer, the term of this patent is extended or adjusted under 35 U.S.C. 154(b) by 1177 days.

(21) Appl. No.: 12/281,399

(22) PCT Filed: Mar. 2, 2007

(86) PCT No.: PCT/US2007/063142

§ 371 (c)(1), (2), (4) Date: Feb. 20, 2009

(87) PCT Pub. No.: WO2007/103775

PCT Pub. Date: Sep. 13, 2007

(65) Prior Publication Data

US 2009/0214616 A1 Aug. 27, 2009

Related U.S. Application Data

(60) Provisional application No. 60/779,149, filed on Mar. 3, 2006.

(51) Int. Cl.
*A61F 2/00* (2006.01)
*A61K 38/43* (2006.01)
*A61K 9/00* (2006.01)

(52) U.S. Cl.
USPC .......................... 424/423; 424/94.1; 424/400

(58) Field of Classification Search
USPC ........................................ 424/423, 94.1, 400
See application file for complete search history.

(56) References Cited

U.S. PATENT DOCUMENTS 6,743,778 B2 * 6/2004 Kohno ...................... 424/130.1
2004/0028655 A1 * 2/2004 Nelson et al. ................ 424/93.2
2005/0175666 A1 * 8/2005 Ding ............................ 424/423

FOREIGN PATENT DOCUMENTS

WO WO 0228406 A2 * 4/2002
WO WO 2004046332 A2 * 6/2004

* cited by examiner

*Primary Examiner* — Frederick Krass
*Assistant Examiner* — Dennis J Parad
(74) *Attorney, Agent, or Firm* — Armstrong Teasdale LLP

(57) ABSTRACT

The invention generally relates to substrates and surfaces having substrates. Generally speaking, the substrates may be thinly layered substrates, and the surfaces may comprise thinly layered substrates. Additionally, the substrates may comprise a multifunctional water soluble polymer and a lipoprotein and the surfaces may comprise a multifunctional water soluble polymer and a lipoprotein.

44 Claims, 38 Drawing Sheets

A

B

A

B

A

B

A

B

SEQUENCE LISTING

<160> NUMBER OF SEQ ID NOS: 9

<210> SEQ ID NO 1
<211> LENGTH: 1857
<212> TYPE: DNA
<213> ORGANISM: Artificial
<220> FEATURE:
<223> OTHER INFORMATION: HUMAN

<400> SEQUENCE: 1
atgtccccta tactaggtta ttggaaaatt aagggccttg tgcaacccac tcgacttctt 60
ttggaatatc ttgaagaaaa atatgaagag catttgtatg agcgcgatga aggtgataaa 120
tggcgaaaca aaaagtttga attgggtttg gagtttccca atcttcctta ttatattgat 180
ggtgatgtta aattaacaca gtctatggcc atcatacgtt atatagctga caagcacaac 240
atgttgggtg gttgtccaaa agagcgtgca gagatttcaa tgcttgaagg agcggttttg 300
gatattagat acggtgtttc gagaattgca tatagtaaag actttgaaac tctcaaagtt 360
gattttctta gcaagctacc tgaaatgctg aaaatgttcg aagatcgttt atgtcataaa 420
acatatttaa atggtgatca tgtaacccat cctgacttca tgttgtatga cgctcttgat 480
gttgttttat acatggaccc aatgtgcctg gatgcgttcc caaaattagt ttgttttaaa 540
aaacgtattg aagctatccc acaaattgat aagtacttga aatccagcaa gtatatagca 600
tggcctttgc agggctggca agccacgttt ggtggtggcg accatcctcc aaaatcggat 660
ctggaagttc tgttccaggg gcccctggga tccccggaat tcatggatcc agcgggcggc 720
ccccggggcg tgctcccgcg gccctgccgc gtgctggtgc tgctgaaccc gcgcggcggc 780
aagggcaagg ccttgcagct cttccggagt cacgtgcagc ccctttggc tgaggctgaa 840 atctccttca cgctgatgct cactgagcgg cggaaccacg cgcgggagct ggtgcggtcg 900
gaggagctgg gccgctggga cgctctggtg gtcatgtctg gagacgggct gatgcacgag 960
gtggtgaacg ggctcatgga gcggcctgac tgggagaccg ccatccagaa gcccctgtgt 1020

```
agcctcccag caggctctgg caacgcgctg gcagcttcct tgaaccatta tgctggctat   1080

gagcaggtca ccaatgaaga cctcctgacc aactgcacgc tattgctgtg ccgccggctg   1140

ctgtcaccca tgaacctgct gtctctgcac acggcttcgg ggctgcgcct cttctctgtg   1200

ctcagcctgg cctggggctt cattgctgat gtggacctag agagtgagaa gtatcggcgt   1260

ctgggggaga tgcgcttcac tctgggcacc ttcctgcgtc tggcagccct gcgcacctac   1320

cgcggccgac tggcctacct ccctgtagga agagtgggtt ccaagacacc tgcctccccc   1380

gttgtggtcc agcagggccc ggtagatgca caccttgtgc cactggagga gccagtgccc   1440

tctcactgga cagtggtgcc cgacgaggac tttgtgctag tcctggcact gctgcactcg   1500

cacctgggca gtgagatgtt tgctgcaccc atgggccgct gtgcagctgg cgtcatgcat   1560

ctgttctacg tgcgggcggg agtgtctcgt gccatgctgc tgcgcctctt cctggccatg   1620

gagaagggca ggcatatgga gtatgaatgc ccctacttgg tatatgtgcc cgtggtcgcc   1680

ttccgcttgg agcccaagga tgggaaaggt gtgtttgcag tggatgggga attgatggtt   1740

agcgaggccg tgcagggcca ggtgcaccca aactacttct ggatggtcag cggttgcgtg   1800

gagcccccgc ccagctggaa gccccagcag atgccaccgc cagaagagcc cttatga      1857


<210> SEQ ID NO 2
<211> LENGTH: 1860
<212> TYPE: DNA
<213> ORGANISM: Artificial
<220> FEATURE:
<223> OTHER INFORMATION: HUMAN

<400> SEQUENCE: 2

atgtccccta tactaggtta ttggaaaatt aagggccttg tgcaacccac tcgacttctt     60

ttggaatatc ttgaagaaaa atatgaagag catttgtatg agcgcgatga aggtgataaa    120

tggcgaaaca aaaagtttga attgggtttg gagtttccca atcttcctta ttatattgat    180

ggtgatgtta aattaacaca gtctatggcc atcatacgtt atatagctga caagcacaac    240

atgttgggtg gttgtccaaa agagcgtgca gagatttcaa tgcttgaagg agcggttttg    300

gatattagat acggtgtttc gagaattgca tatagtaaag actttgaaac tctcaaagtt    360

gattttctta gcaagctacc tgaaatgctg aaaatgttcg aagatcgttt atgtcataaa    420

acatatttaa atggtgatca tgtaacccat cctgacttca tgttgtatga cgctcttgat    480

gttgttttat acatggaccc aatgtgcctg gatgcgttcc caaaattagt ttgttttaaa    540

aaacgtattg aagctatccc acaaattgat aagtacttga aatccagcaa gtatatagca    600

tggcctttgc agggctggca agccacgttt ggtggtggcg accatcctcc aaaatcggat    660

ctggaagttc tgttccaggg gcccctggga tccccggaat tctgtatgga tccagcgggc    720

ggcccccggg gcgtgctccc gcggccctgc cgcgtgctgg tgctgctgaa cccgcgcggc    780

ggcaagggca aggccttgca gctcttccgg agtcacgtgc agccccttt ggctgaggct     840

gaaatctcct tcacgctgat gctcactgag cggcggaacc acgcgcggga gctggtgcgg    900

tcggaggagc tgggccgctg ggacgctctg gtggtcatgt ctggagacgg gctgatgcac    960

gaggtggtga acgggctcat ggagcggcct gactgggaga ccgccatcca gaagcccctg   1020

tgtagcctcc cagcaggctc tggcaacgcg ctggcagctt ccttgaacca ttatgctggc   1080

tatgagcagg tcaccaatga agacctcctg accaactgca cgctattgct gtgccgccgg   1140

ctgctgtcac ccatgaacct gctgtctctg cacacggctt cggggctgcg cctcttctct   1200

gtgctcagcc tggcctgggg cttcattgct gatgtggacc tagagagtga gaagtatcgg   1260
```

```
cgtctggggg agatgcgctt cactctgggc accttcctgc gtctggcagc cctgcgcacc   1320

taccgcggcc gactggccta cctccctgta ggaagagtgg gttccaagac acctgcctcc   1380

cccgttgtgg tccagcaggg cccggtagat gcacaccttg tgccactgga ggagccagtg   1440

ccctctcact ggacagtggt gcccgacgag gactttgtgc tagtcctggc actgctgcac   1500

tcgcacctgg gcagtgagat gtttgctgca cccatgggcc gctgtgcagc tggcgtcatg   1560

catctgttct acgtgcgggc gggagtgtct cgtgccatgc tgctgcgcct cttcctggcc   1620

atggagaagg gcaggcatat ggagtatgaa tgcccctact tggtatatgt gcccgtggtc   1680

gccttccgct tggagcccaa ggatgggaaa ggtgtgtttg cagtggatgg ggaattgatg   1740

gttagcgagg ccgtgcaggg ccaggtgcac ccaaactact tctggatggt cagcggttgc   1800

gtggagcccc cgcccagctg gaagccccag cagatgccac cgccagaaga gcccttatga   1860
```

<210> SEQ ID NO 3
<211> LENGTH: 738
<212> TYPE: DNA
<213> ORGANISM: Artificial
<220> FEATURE:
<223> OTHER INFORMATION: HUMAN

<400> SEQUENCE: 3

```
atgtgtgatg aacccccccca gagcccctgg gatcgagtga aggacctggc cactgtgtac     60

gtggatgtgc tcaaagacag cggcagagac tatgtgtccc agtttgaagg ctccgccttg    120

ggaaaacagc taaacctaaa gctccttgac aactgggaca gcgtgacctc caccttcagc    180

aagctgcgcg aacagctcgg ccctgtgacc caggagttct gggataacct ggaaaaggag    240

acagagggcc tgaggcagga gatgagcaag gatctggagg aggtgaaggc caaggtgcag    300

ccctacctgg acgacttcca gaagaagtgg caggaggaga tggagctcta ccgccagaag    360

gtggagccgc tgcgcgcaga gctccaagag ggcgcgcgcc agaagctgca cgagctgcaa    420

gagaagctga gcccactggg cgaggagatg cgcgaccgcg cgcgcgccca tgtggacgcg    480

ctgcgcacgc atctggcccc ctacagcgac gagctgcgcc agcgcttggc cgcgcgcctt    540

gaggctctca aggagaacgg cggcgccaga ctggccgagt accacgccaa ggccaccgag    600

catctgagca cgctcagcga gaaggccaag cccgcgctcg aggacctccg ccaaggcctg    660

ctgcccgtgc tggagagctt caaggtcagc ttcctgagcg ctctcgagga gtacactaag    720

aagctcaaca cccagtga                                                  738
```

<210> SEQ ID NO 4
<211> LENGTH: 741
<212> TYPE: DNA
<213> ORGANISM: Artificial
<220> FEATURE:
<223> OTHER INFORMATION: HUMAN

<400> SEQUENCE: 4

```
atgtgtgatg aacccccccca gagcccctgg gatcgagtga aggacctggc cactgtgtac     60

gtggatgtgc tcaaagacag cggcagagac tatgtgtccc agtttgaagg ctccgccttg    120

ggaaaacagc taaacctaaa gctccttgac aactgggaca gcgtgacctc caccttcagc    180

aagctgcgcg aacagctcgg ccctgtgacc caggagttct gggataacct ggaaaaggag    240

acagagggcc tgaggcagga gatgagcaag gatctggagg aggtgaaggc caaggtgcag    300

ccctacctgg acgacttcca gaagaagtgg caggaggaga tggagctcta ccgccagaag    360
```

```
gtggagccgc tgcgcgcaga gctccaagag ggcgcgcgcc agaagctgca cgagctgcaa    420

gagaagctga gcccactggg cgaggagatg cgcgaccgcg cgcgcgccca tgtggacgcg    480

ctgcgcacgc atctggcccc ctacagcgac gagctgcgcc agcgcttggc cgcgcgcctt    540

gaggctctca aggagaacgg cggcgccaga ctggccgagt accacgccaa ggccaccgag    600

catctgagca cgctcagcga gaaggccaag cccgcgctcg aggacctccg ccaaggcctg    660

ctgcccgtgc tggagagctt caaggtcagc ttcctgagcg ctctcgagga gtacactaag    720

aagctcaaca cccagtgttg a                                              741
```

```
<210> SEQ ID NO 5
<211> LENGTH: 11
<212> TYPE: PRT
<213> ORGANISM: Artificial
<220> FEATURE:
<223> OTHER INFORMATION: HUMAN
<220> FEATURE:
<221> NAME/KEY: misc_feature
<222> LOCATION: (1)..(1)
<223> OTHER INFORMATION: ACETYL

<400> SEQUENCE: 5

Gly Cys Gly Tyr Gly Arg Gly Asp Ser Pro Gly
1               5                   10
```

```
<210> SEQ ID NO 6
<211> LENGTH: 12
<212> TYPE: PRT
<213> ORGANISM: Artificial
<220> FEATURE:
<223> OTHER INFORMATION: HUMAN
<220> FEATURE:
<221> NAME/KEY: misc_feature
<222> LOCATION: (1)..(1)
<223> OTHER INFORMATION: ACETYL
<220> FEATURE:
<221> NAME/KEY: misc_feature
<222> LOCATION: (2)..(2)
<223> OTHER INFORMATION: TRITYL
<220> FEATURE:
<221> NAME/KEY: misc_feature
<222> LOCATION: (5)..(5)
<223> OTHER INFORMATION: METHOXY-TRITYL
<220> FEATURE:
<221> NAME/KEY: misc_feature
<222> LOCATION: (11)..(11)
<223> OTHER INFORMATION: METHOXY-TRITYL

<400> SEQUENCE: 6

Gly Cys Asn Ala Cys Arg Gly Asp Gly Trp Cys Gly
1               5                   10
```

```
<210> SEQ ID NO 7
<211> LENGTH: 21
<212> TYPE: DNA
<213> ORGANISM: Artificial
<220> FEATURE:
<223> OTHER INFORMATION: HUMAN

<400> SEQUENCE: 7

ctgtcagcct ccgtgttcag t                                               21
```

```
<210> SEQ ID NO 8
<211> LENGTH: 24
<212> TYPE: DNA
<213> ORGANISM: Artificial
<220> FEATURE:
<223> OTHER INFORMATION: HUMAN
```

```
<400> SEQUENCE: 8

tcgccatcgc cattgagcgc tata                                    24


<210> SEQ ID NO 9
<211> LENGTH: 24
<212> TYPE: DNA
<213> ORGANISM: Artificial
<220> FEATURE:
<223> OTHER INFORMATION: HUMAN

<400> SEQUENCE: 9

tcgccatcgc cattgagcgc tata                                    24
```

BIOMATERIALS HAVING NANOSCALE LAYERS AND COATINGS

GOVERNMENTAL RIGHTS

This invention was made with government support under T32 HL07916-05 awarded by the NIH. The government has certain rights in the invention.

FIELD OF THE INVENTION

The invention generally relates to thinly layered substrates and surfaces having thinly layered substrates, as well as substrates comprising a multifunctional water soluble polymer layer and a recombinant high density lipoprotein and surfaces having substrates comprising a multifunctional water soluble polymer layer and a recombinant high density lipoprotein.

BACKGROUND OF THE INVENTION

Biomaterials are synthetic or natural materials that function in intimate contact with living tissue. Biomaterials may be applied to the surface of a tissue to form a tissue surface, or they may be applied to the surface of a medical device, sensor, or implant. Synthetic biomaterials comprising hydrophilic polymers (hydrogels) are favorable because water associates with the water-soluble polymer, and the structure of the water around the polymer hinders protein adsorption.

Because of their ability to be in intimate contact with tissue, several attempts have been made to produce thinly layered, durable biomaterials that can be utilized to deliver a drug in vivo. But producing a thinly layered biomaterial suitable for drug delivery has proven to be a challenge. Several thinly layered biomaterials have been produced, but are not utilized for drug delivery. For example, thin polymer films comprising multiple layers of polyelectrolytes linked non-covalently have been formed and stabilized by chemical cross-links. Thin polymer films comprising multiple layers of covalently cross-linked hydrophilic polymers have also been formed layer-by-layer.

Attempts have been made to include proteins in biomaterials to function as drug carrying agents. Proteins, for example, have been cross-linked with hydrophilic polymers to form thick hydrogels (U.S. Pat. No. 5,733,563). Drugs or enzymes have been added to thick PEG/albumin hydrogels (Journal of Artificial Cells, Blood Substitutes, and Immobilization Biotechnology 1995, 23, 605-611; Biotechnology Applied Biochemistry 2001, 33, 201-207). It is difficult, however, to form certain surface coatings with these thick hydrogels. Additionally, it is difficult to achieve controlled drug release with these thick hydrogels. A need, therefore, remains for both thick and thinly layered biomaterials having proteins that can be utilized to deliver drugs in vivo.

SUMMARY OF THE INVENTION

In one embodiment, the invention encompasses a substrate. The substrate is comprised of a plurality of cross-linked, distinctly-formed layers, where the distinctly-formed layers are comprised of multifunctional, water soluble polymer layers and protein layers. The protein is comprised of at least one lipid binding site, and each protein layer is disposed between two layers of the water soluble polymer, whereby each protein layer cross-links the water soluble polymer layers together to form the plurality of distinctly-formed layers.

In another embodiment, the invention encompasses a surface. The surface is coated with a plurality of cross-linked, distinctly-formed layers, the distinctly-formed layers are comprised of multifunctional, water soluble polymer layers and protein layers. The protein is comprised of at least one lipid binding site, and each protein layer is disposed between two layers of the water soluble polymer, whereby each protein layer cross-links the water soluble polymer layers together to form the plurality of distinctly-formed layers.

In yet another embodiment, the invention encompasses a substrate, the substrate comprising a multifunctional water soluble polymer layer and a recombinant high density lipoprotein, whereby the recombinant high density lipoprotein cross-links the water soluble polymer.

In still another embodiment, the invention encompasses a surface, the surface being coated with a substrate comprising a multifunctional water soluble polymer layer and a recombinant high density lipoprotein, whereby the recombinant high density lipoprotein cross-links the water soluble polymer.

DETAILED DESCRIPTION OF THE INVENTION

Figure 1:
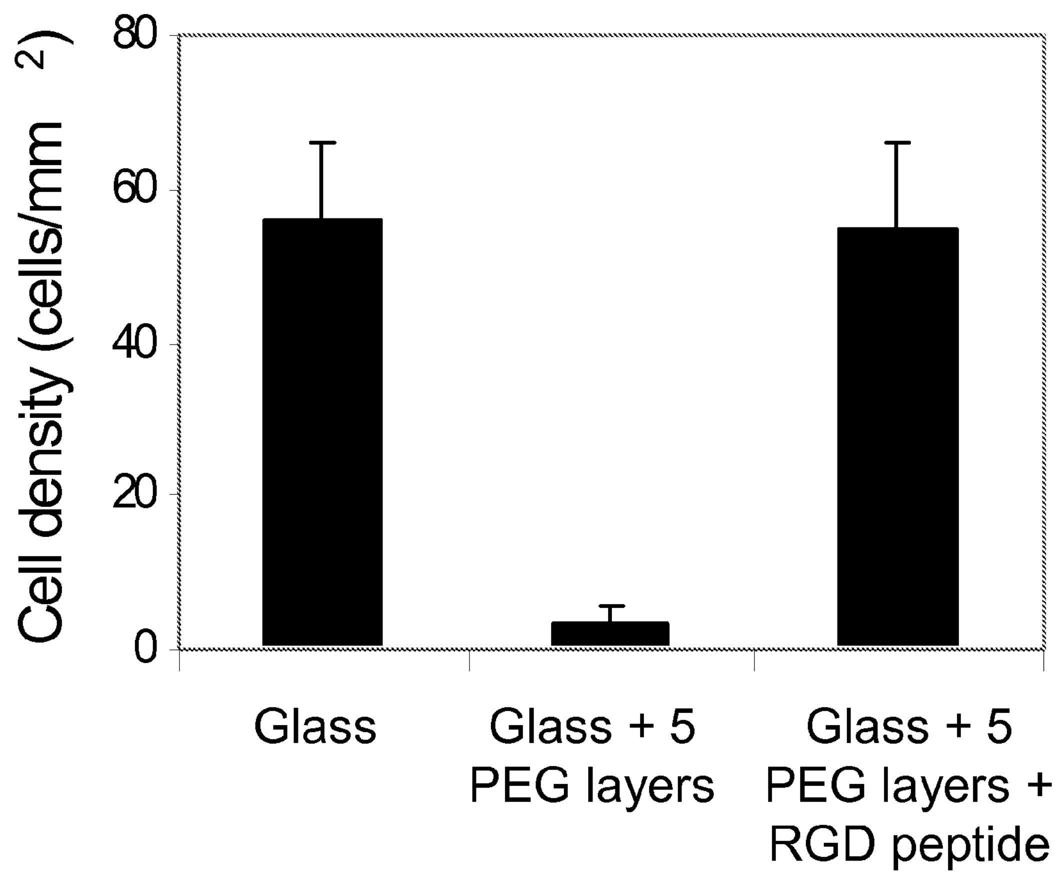
FIG. 1 depicts a schematic of a graph illustrating the density of human umbilical vein endothelial cells that adhered to the different multilayered hydrogel materials. Data represent mean±standard deviation.

A process has been discovered to produce substrates and surfaces coated with the substrates. Typically, the substrate will be biocompatible. The thickness, elasticity, and density of the layers may advantageously be altered to provide a substrate or surface suitable for a variety of applications. In addition, the composition of the layers may be altered to provide a substrate suitable for a variety of applications. In some medical applications, for example, the substrate or surface may further include a therapeutic agent. The amount of therapeutic agent, and the duration of its administration, may be altered by varying the density and number of layers comprising the substrate or coating the surface.

I. Substrate

One aspect of the invention provides a substrate having one or more layers comprised of polymer and protein. In one embodiment, the substrate is comprised of a plurality of distinctly formed layers of polymer and protein. In these embodiments, the protein layers are disposed between polymer layers and cross-link the polymer layers together to form a continuous matrix having a thickness, elasticity and density suitable for a particular application. In other embodiments, the polymer and protein form a single layer having a thickness, elasticity and density suitable for a particular application. In some embodiments, the substrate may optionally include one or more agents selected from a therapeutic agent, a therapeutic molecule that converts an endogenous precursor to an active form, and an agent that promotes adhesion of cells.

(a) Polymer

As will be appreciated by a skilled artisan, a variety of polymers are suitable for use in the invention. Typically, the polymer will be a water soluble polymer. If the substrate is layered, generally speaking the water soluble polymer will form the first layer of the substrate. Suitable examples of water soluble polymers include hydrophilic polymers, cellulose derivatives, polysaccharide or carbohydrate polymers, and biodegradable polymers.

In one embodiment, the water soluble polymer may be a hydrophilic polymer. A variety of hydrophilic polymers are suitable for use in the invention. Non-limiting examples of suitable hydrophilic polymers include polyacrylate, polyacrylamide, poly(acrylamide sulphonic acid), polyacrylonitrile, polyamines, poly(ethylene glycol), poly(ethylene imine), poly(ethylene oxide), poly(ethyloxazoline), polyhydroxyethylacrylate, polymethacrylate, polymethacrylamide, poly(oxyalkylene oxide), poly(propylene oxide), polyurethane, poly(vinyl alcohol), and poly(vinyl pyrrolidone). In one embodiment, the hydrophilic polymer is poly(ethylene imine). In another embodiment, the polymer is poly(ethylene oxide). In an exemplary embodiment, the hydrophilic polymer is poly(ethylene glycol), commonly referred to as "PEG."

In an alternative embodiment, the water soluble polymer is a cellulose derivative. Suitable cellulose derivatives include methylcellulose, carboxymethylcellulose, hydroxyethylcellulose, hydroxypropylcellulose, and hydroxy-propylmethylcellulose.

In a further alternative embodiment, the water soluble polymer is a polysaccharide or carbohydrate. Suitable polysaccharides or carbohydrate polymers include hyaluronic acid, dextran, dextrin, heparan sulfate, chondroitin sulfate, heparin, alginate, agar, carrageenan, xanthan, and guar.

In another embodiment, the water soluble polymer is a poly(amino acid). Non-limiting examples of suitable poly (amino acids) include polylysine, polyglycine, and polyserine.

In yet another alternative embodiment, the water soluble polymer is a biodegradable polymer. Suitable biodegradable polymers include polyanhydride, polyhydroxy acid, and polycarbonate.

The water soluble polymer may be a variety of molecular weights and may be either linear or branched (i.e., a "branched" polymer is comprised of a plurality of arms). As will be appreciated by a skilled artisan, the elasticity of the polymer is generally proportional to the polymer's average molecular weight and more precisely for a branched polymer, to the average molecular weight of the polymer's arms. As the average molecular weight of the polymer or its arms increases, typically the elasticity of the polymer increases. Conversely, as the average molecular weight of the polymer or its arms decreases, typically the elasticity of the polymer decreases. Depending on the application for the substrate, the elasticity of the polymer can and will vary. In some applications, for example, a highly elastic polymer may be desirable, while in other applications a polymer having a moderate to brittle degree of elasticity may be desirable. Generally speaking, branched polymers having a high degree of elasticity (e.g., that can stretch approximately 300 percent or more without breaking) may have an average molecular weight for each arm of about 35,000 daltons. Branched polymers having a medium degree of elasticity may have an average molecular weight for each arm of about 2000 daltons to about 15,000 daltons. Branched polymers having a low degree of elasticity (i.e., brittle) may have an average molecular weight for each arm of less than about 500 daltons.

A variety of water soluble polymers that have different branching patterns are suitable for use in the invention. For example, in one embodiment, the polymer is poly(ethylene glycol) that has four-arms. In another embodiment, the polymer is poly(ethylene glycol) that has six-arms. In yet another embodiment, the polymer is poly(ethylene glycol) that has eight arms. Similarly, each arm comprising a polymer, such as the poly(ethylene glycol), may have a different molecular weight. In one embodiment, each arm of the water soluble polymer may have an average molecular weight of from about 500 daltons to about 35,000 daltons. In another embodiment, each arm of the water soluble polymer has an average molecular weight of from about 15,000 daltons to about 35,000 daltons. In yet another embodiment, each arm of the water soluble polymer has an average molecular weight of from about 2,000 daltons to about 15,000 daltons. In a further embodiment, each arm of the water soluble polymer has an average molecular weight of from about 500 daltons to about 2,000 daltons.

According to the process of the invention, generally the polymer is contacted with a reagent to form a polymer derivatized with one or more reactive groups. The reactive group added to the polymer is selected so that the reactive group, when contacted with the protein, forms a cross-link between the polymer and protein layers. A variety of reagents are suitable for use to add reactive groups to polymers. Suitable reactive groups include sulfones, sulfoxides, sulfonates or sulfonamides, phosphonates or phosphonamides. In one preferred embodiment, the reactive group is a vinyl sulfone. In another embodiment, the reactive group is a diacrylate. In yet another embodiment, the reactive group is a diamine. In particular, the reactive group may be any reactive group that creates a modified polymer having high reactivity and specificity towards a functional group in a desired protein. In one embodiment, the modified polymer provides high reactivity and specificity towards sulfhydryl groups in a protein. In another embodiment, the modified polymer provides reactivity and specificity toward amino groups in a protein.

(b) Protein

A variety of proteins are suitable for use in the invention. Those skilled in the art will appreciate that the protein can and will vary depending on the polymer and the desired use of the substrate. Generally, as detailed above, the protein is selected so that it has at least one functional group that reacts with the reactive group of the polymer to form a cross-linked layer. Suitable functional groups include an amino, a sulfhydryl, a hydroxyl, or a carboxyl group. In one preferred embodiment, the protein has an amino functional group. In another embodiment, the protein has a thiol functional group. In an exemplary embodiment, as detailed in the examples, the protein is a recombinant protein engineered to have additional functional groups as compared to the native protein.

In an exemplary embodiment, the protein is a lipoprotein. A lipoprotein is a protein that has the ability to stabilize, retain and transport one or more lipids, and may also bind lipid-like molecules and lipid-binding proteins. Because lipoproteins normally function as lipid transporters in vivo, a protein layer comprised of lipoproteins advantageously provide a means to store and deliver lipophilic molecules, such as therapeutic agents. In some embodiments, the lipoprotein may have from about one to about seven lipid binding sites. In other embodiments, the lipoprotein may have more than about seven lipid binding sites.

Numerous suitable lipoproteins may be used. By way of non-limiting example, suitable lipoproteins include chylomicrons, very low density lipoproteins, intermediate density lipoproteins, low density lipoproteins, and high density lipoproteins. In one embodiment, the lipoprotein is selected from the group consisting of Apo A-I, Apo A-II, Apo A-IV, Apo B-48, Apo B-100, Apo C-1, Apo C-II, Apo C-III, Apo D, Apo E, Apo H, and cholesterol ester transfer protein, i.e., "CETP." In a preferred embodiment, the lipoprotein is selected from the group consisting of Apo A-1, Apo B-48, Apo B-100. In another embodiment, the protein is a high density lipoprotein particle comprising Apo A-I and lipids. In another embodiment, the protein is another lipid-binding protein, such as albumin. Suitable sources of albumin are blood serum (e.g. BSA), milk (lactalbumin), or egg (ovalbumin).

In another embodiment, the protein is a recombinant protein. In an exemplary embodiment, the recombinant protein is a recombinant lipoprotein. Generally speaking, the recombinant protein typically will have added amino acid residues (compared to the native protein) with groups that react with the reactive group of the polymer to form a cross-linked layer. In one embodiment, additional cysteine residues may be added to the recombinant protein by attaching a GST tag to one end of the protein. In an alternative embodiment, the recombinant protein may have one or more cysteine residues added to one or both ends of the protein. In still another alternative embodiment, the recombinant protein may have one or more lysine residues added to the N-terminus, the C-terminus, or both. In a further embodiment, the recombinant protein may have additional serine residues added to one or both ends of the protein. In still an additional embodiment, the recombinant protein may have a mixture of additional amino acids having groups selected from amino groups, sulfhydryl groups, and hydroxyl groups.

In one embodiment, the recombinant protein is a recombinant high density lipoprotein. In another embodiment, the recombinant protein is a recombinant high density lipoprotein comprised of Apo AI.

In an exemplary embodiment, the recombinant protein is encoded by a nucleic acid sequence of either SEQ ID NO: 3 or 4, which contain either one or two additional cysteine residues. In another embodiment, the recombinant protein has an amino acid sequence that is at least 50, 55, 60 or 65 percent identical to a protein encoded by a nucleic acid sequence of either SEQ ID NO. 3 or 4. In yet another embodiment, the recombinant protein has an amino acid sequence that is at least 70, 75, 80, or 85 percent identical to a protein encoded by a nucleic acid sequence of either SEQ ID NO. 3 or 4. In still another embodiment, the recombinant protein has an amino acid sequence that is at least 94, 95, 96, or 97 percent identical to a protein encoded by a nucleic acid sequence of either SEQ ID NO. 3 or 4. In a further embodiment, the recombinant protein has an amino acid sequence that is at least 97, 98, or 99 percent identical to a protein encoded by a nucleic acid sequence of either SEQ ID NO. 3 or 4.

In determining whether a recombinant protein is substantially identical to the recombinant protein of the invention, sequence similarity may be determined by conventional algorithms, which typically allow introduction of a small number of gaps in order to achieve the best fit. In particular, "percent identity" of two polypeptides or two nucleic acid sequences is determined using the algorithm of Karlin and Altschul (Proc. Natl. Acad. Sci. USA 87:2264-2268, 1993). Such an algorithm is incorporated into the BLASTN and BLASTX programs of Altschul et al. (J. Mol. Biol. 215:403-410, 1990). BLAST nucleotide searches may be performed with the BLASTN program to obtain nucleotide sequences homologous to a nucleic acid molecule of the invention. Equally, BLAST protein searches may be performed with the BLASTX program to obtain amino acid sequences that are homologous to a recombinant fusion protein of the invention. To obtain gapped alignments for comparison purposes, Gapped BLAST is utilized as described in Altschul et al. (Nucleic Acids Res. 25:3389-3402, 1997). When utilizing BLAST and Gapped BLAST programs, the default parameters of the respective programs (e.g., BLASTX and BLASTN) are employed. See http://www.ncbi.nlm.nih.gov for more details.

The recombinant protein of the invention may be synthesized, produced by recombinant technology, or purified from cells. In one embodiment, the subject recombinant protein may also be expressed and purified from cell and cell-free systems. Any of the molecular and biochemical methods known in the art are available for biochemical synthesis, molecular expression and purification of the recombinant fusion protein of the invention, see e.g. Molecular Cloning, A Laboratory Manual (Sambrook, et al. Cold Spring Harbor Laboratory), Current Protocols in Molecular Biology (Eds. Ausubel, et al., Greene Publ. Assoc., Wiley-Interscience, New York).

(c) Therapeutic Molecule

The substrate may optionally include one or more therapeutic molecules (e.g., drugs). The substrate, as such, may be used to store or deliver a drug in vivo effective for treating a desired indication in a subject. In an exemplary embodiment, the substrate may be used to deliver a drug to a targeted location, such as a specific tissue or organ, in the subject. By way of non-limiting example, the substrate may be a hydrogel having an anticoagulant. In this application, the hydrogel may be applied to the heart area of a subject that has recently had heart surgery to prevent blood clot formation. In another application, for example, the substrate may be a hydrogel having a chemotherapeutic agent. In this application, the hydrogel may be applied directly to a specific tissue or organ in a subject to target the drug to cancer cells. By way of further non-limiting example, the substrate may be a hydrogel having an antibiotic. In this application, the hydrogel may be applied to the bacterial-infected area of a subject to treat the infection. A detailed discussion of hydrogel embodiments is described below.

As can and will be appreciated by a skilled artisan, depending on the indication being treated, a variety of therapeutic molecules may be non covalently conjugated to the substrate by any method generally known in the art. In some embodiments, the therapeutic agent may be non covalently conjugated to a polymer comprising the polymer layer in a layered substrate. In other embodiments, the therapeutic agent may be non covalently conjugated to a lipoprotein comprising the protein layer in a layered substrate. In an alternative embodiment, the therapeutic agent may be non covalently conjugated to a polymer comprising a single layer substrate. In another alternative, the therapeutic agent may be non covalently conjugated to a lipoprotein comprising a single layer substrate. Suitable therapeutic molecules, for example, may be selected from the group consisting of anti-inflammatory agents, chemotherapeutic agents, endothelial cell migration promoting agents, angiogenesis promoting agents, anticoagulants, antibacterial agents, antiparasitic agents, antifungal agents, antiviral agents, analgesic agents, local anesthetics, and immunomodulatory agents.

In one embodiment, the therapeutic molecule is an anti-inflammatory agent. Suitable anti-inflammatory agents may be either nonsteroidal or steroidal. Nonsteroidal anti-inflammatory agents, for example, include acetylsalicylic acid, indomethacin, naproxen, and selective cyclooxygenase-2 inhibitors. Steroidal anti-inflammatory agents, for example, include hydrocortisone, and prednisone.

In another embodiment, the therapeutic molecule is a chemotherapeutic agent. Suitable chemotherapeutic agents may be selected from the group consisting of DNA synthesis inhibitors, mitotic inhibitors, antimetabolites, alkylating agents, nitrosoureas, anthracyclines, topoisomerase inhibitors, cytotoxins, anti-cytoskeletals, and angiogenesis inhibitors. Examples of DNA synthesis inhibitors include, but are not limited to, daunorubicin and adriamycin. Examples of mitotic inhibitors include paclitaxel, docetaxel, vinblastine, vincristine, and vinorelbine. Examples of antimetabolites include 5-fluorouracil, capecitabine, 6-mercaptopurine, methotrexate, gemcitabine, cytarabine (ara-C), fludarabine, pemetrexed, cytosine arabinoside, methotrexate, and aminopterin. Examples of alkylating agents include busulfan, cisplatin, carboplatin, chlorambucil, cyclophosphamide, ifosfamide, dacarbazine (DTIC), mechlorethamine, melphalan, and temozolomide. Examples of nitrosoureas include carmustine (BCNU) and iomustine (CCNU). Examples of anthracyclines include daunorubicin, doxorubicin, epirubicin, idarubicin, and mitoxantrone. Examples of topoisomerase inhibitors include topotecan, irinotecan, etoposide (VP-16), and teniposide. Examples of cytotoxins include paclitaxel, vinblastine, and macromycin. Examples of anti-cytoskeletals include taxol and cholchicine. Examples of angiogenesis inhibitors include thalidomide, angiogenic growth factor inhibitors, and matrix metalloproteinase inhibitors.

In another embodiment, the therapeutic molecule is an anticoagulant. Suitable anticoagulants include heparin, coumarins, 1,3-indanediones, argatroban, lepirudin, and bivalirudin.

In yet another embodiment, the therapeutic molecule is an angiogenesis promoting agent. Suitable angiogenesis promoting agents include vascular endothelial growth factor (VEGF), fibroblast growth factor (FGF), interleukin-8 (IL-8), angiogenin, angiopoietin-1, angiotropin, epidermal growth factor (EGF), platelet derived endothelial cell growth factor (PDGF), granulocyte colony-stimulating factor (GCSF), transforming growth factor a (TGF-a), transforming growth factor b (TGF-b), proliferin, leptin, sphingosine 1-phospate (S1P), and nitric oxide (See Möller et al, J. Biol. Chem. 280: 8850-8854).

In a further embodiment, the therapeutic molecule is an antibacterial agent. Suitable antibacterial agents include penicillin, cephalosporins, and bacitracin. In another embodiment, the therapeutic molecule is an antiparasitic agent. Suitable antiparasitic agents include quinacrine and chloroquine. In another embodiment, the therapeutic molecule is an antifungal agent. Suitable antifungal agents include nystatin and gentamicin. In yet another embodiment, the therapeutic molecule is an antiviral agent. Suitable antiviral agents include acyclovir, ribavirin, and interferons.

In one embodiment, the therapeutic molecule is an analgesic agent. Suitable analgesic agents include salicylic acid, acetaminophen, ibuprofen, flurbiprofen, and morphine. In another embodiment, the therapeutic molecule is a local anesthetic. Suitable local anesthetics include lidocaine, bupivacaine, and benzocaine. In yet another embodiment, the therapeutic molecule is an immunomodulatory agent. Suitable immunomodulatory agents include granulocyte colony-stimulating factor (G-CSF), interferons, imiquimod, IL-12, chemokines, synthetic cytosine phosphate-guanosine (CpG) oligodeoxynucleotides, and glucans.

Depending on the therapeutic molecule and the intended use of the substrate, the therapeutic molecule may be introduced into the substrate using a variety of methods. In one embodiment, the therapeutic molecule may be non covalently attached to the lipoproteins in the protein layers of an already formed layered substrate. In another embodiment, the therapeutic molecule may be non covalently attached to the lipoproteins that will be used to form the protein layers of a layered substrate. In yet another embodiment, the therapeutic molecule may be non covalently attached to the lipoproteins that will comprise a single layered substrate. In still another embodiment, the therapeutic molecule may be non covalently attached to the lipoprotein of an already formed single layered substrate.

Generally speaking, by non covalently attaching the therapeutic molecule to the substrate, the drug may be administered to a subject in a time controlled manner. The therapeutic molecule is generally slowly released from the substrate after the substrate has been contacted in vivo with a subject's blood or tissue. In one embodiment, less than about 75 percent of the therapeutic molecule is released from the substrate in about 24 hours after the substrate has been contacted in vivo with a subject's blood or tissue. In another embodiment, less than about 90 percent of the therapeutic molecule is released from the substrate in about 24 hours after the substrate has been contacted in vivo with a subject's blood or tissue. In another embodiment, the therapeutic molecule is released from the substrate in a controlled release formulation over a period of about thirty days after the substrate has been contacted in vivo with a subject's blood.

The concentration of therapeutic agent loaded on the substrate may readily be varied to optimize the amount of drug administered to a subject. To achieve a relatively high loading density of drug, the substrate will generally have a relatively high concentration of lipoprotein. The concentration of lipoprotein, for example, may be increased by increasing the thickness of individual layers, by increasing the total number of layers, by selecting a lipoprotein having several lipid binding sites or any combination thereof. Conversely, to achieve a relatively low loading density of drug, the substrate will generally have a relatively low concentration of lipoprotein. The concentration of lipoprotein may be decreased by decreasing the thickness of individual layers, by decreasing the total number of layers, by selecting a lipoprotein having few lipid binding sites or any combination thereof.

(d) Therapeutic Molecule that Converts Inactive Precursor

The substrate may optionally include a therapeutic molecule that converts an endogenous precursor form of a molecule to the active form of the endogenous molecule. Typically, the therapeutic molecule may be an enzyme that will convert an inactive agent present in the blood of a subject to an active form. Suitable enzymes, by way of non-limiting example, include sphingosine kinase, lysophosphatidic acid (LPA) acetyl transferase, phospholipase C, phospholipase A2, phospholipase D, PI3 kinase, and sphingomyelinase. In one embodiment, the enzyme is a recombinant sphingosine kinase. In an exemplary embodiment, the recombinant sphingosine kinase is encoded by a nucleic acid sequence of either SEQ ID NO: 1 or 2. In another embodiment, the recombinant protein has an amino acid sequence that is at least 50, 55, 60 or 65 percent identical to a protein encoded by a nucleic acid sequence of either SEQ ID NO. 1 or 2. In yet another embodiment, the recombinant protein has an amino acid sequence that is at least 70, 75, 80, or 85 percent identical to a protein encoded by a nucleic acid sequence of either SEQ ID NO. 1 or 2. In still another embodiment, the recombinant protein has an amino acid sequence that is at least 94, 95, 96, or 97 percent identical to a protein encoded by a nucleic acid sequence of either SEQ ID NO. 1 or 2. In a further embodiment, the recombinant protein has an amino acid sequence that is at least 97, 98, or 99 percent identical to a protein encoded by a nucleic acid sequence of either SEQ ID NO. 1 or 2. As described above, sequences similar to the recombinant enzyme may be determined by conventional algorithms.

The therapeutic molecule that converts an endogenous precursor form of a molecule to the active form of the molecule may also be a blood clotting factor. Examples of activating molecules in the blood clotting cascade include tissue factor, factor VIIa, factor Xa, and thrombin.

(e) Proteins that Promote Cell Adhesion

The substrate of the invention may optionally include an agent that promotes adhesion of cells onto the substrate. Typically, the agent will be a polypeptide that promotes adhesion of cells onto the substrate. In one embodiment, the adhesion-promoting polypeptides may be added by contacting the substrate with a solution containing a polypeptide. In another embodiment, the adhesion-promoting polypeptide may comprise one or more proteins layers in the substrate. Suitable adhesion-promoting polypeptides may be selected from the group consisting of integrins, cadherins, immunoglobulin family of cell adhesion molecules, fibronectins, laminins, selectins, mucins, proteoglycans, and fibrillin.

In one exemplary embodiment, the adhesion promoting polypeptide contains an RGD moiety. In one embodiment, the adhesion promoting polypeptide containing an RGD moiety is linear. In another embodiment, the adhesion promoting polypeptide containing an RGD moiety is circular. In one alternative embodiment, the adhesion promoting polypeptide having an RGD moiety has an amino acid sequence comprising SEQ ID NO:5 or SEQ ID NO:6. In another embodiment, the polypeptide having an RGD moiety has an amino acid sequence that is at least 50, 55, 60 or 65 percent identical to SEQ ID NO:5 or SEQ ID NO:6. In yet another embodiment, the polypeptide having an RGD moiety has an amino acid sequence that is at least 70, 75, 80, or 85 percent identical to SEQ ID NO:5 or SEQ ID NO:6. In still another embodiment, the polypeptide having an RGD moiety has an amino acid sequence that is at least 94, 95, 96, or 97 percent identical to SEQ ID NO:5 or SEQ ID NO:6. In a further embodiment, the polypeptide having an RGD moiety has an amino acid sequence that is at least 97, 98, or 99 percent identical to SEQ ID NO:5 or SEQ ID NO:6. Sequence identity may be determined by conventional algorithms as detailed above.

(f) Substrate Hydrogels

In an exemplary embodiment, the substrate will comprise a porous matrix that is a biocompatible hydrogel. In this context, biocompatible means that the hydrogel can be placed in vivo and substantially doesn't provoke an immune response from the subject. A porous matrix is typically a substrate having an average pore diameter of from about 1 nm to 100 μm and generally may weigh from about 10 micrograms to approximately 300 micrograms. As will be appreciated, however, the pore size and weight can and will vary and the present invention includes substrates having average pore diameters and weights outside of the ranges stated herein.

As detailed above, the hydrogel may include a plurality of cross-linked, distinctly formed layers. The process of making a hydrogel having a plurality of cross-linked, distinctly formed layers includes modifying a water soluble polymer to form a polymer layer having polymers with reactive groups. The process also includes contacting the water soluble polymer layer with a protein solution, the protein solution having proteins with at least one lipid binding site and a functional group. The reactive group on the polymers reacts with the functional group in the proteins to form a protein layer cross-linked to the polymer layer. The process can be repeated to form a plurality of cross-linked layers. For more details, see the Examples below. Alternatively, the hydrogel may comprise a single layer. The process of making a hydrogel having a single layer includes modifying a water soluble polymer to form a polymer with reactive groups. The process also includes contacting the water soluble polymer with a protein, the protein having at least one lipid binding site and a functional group. The reactive group on the polymer reacts with the functional group in the protein to form a single layer of protein cross-linked water soluble polymer. In another alternative, the hydrogel may comprise a single layer consisting of particles formed by reaction in solution of a molar excess of one component (protein or polymer) over another. The process of making a hydrogel having a single layer of multilayered particles includes modifying a water soluble polymer to form a polymer with reactive groups. The process also includes contacting the water soluble polymer with a protein, the protein having at least one lipid binding site and a functional group. The reactive group on the polymer reacts with the functional group in the protein to form a soluble protein cross-linked water soluble particle with sizes ranging from 10 nm to 1 micron. The particles are then reacted with a surface. Using particles formed with excess of the opposite component, multilayer films can also be produced with particles. Furthermore, in the formation of particles, if large excesses of one component are used, dendrimeric growth in particle size may be observed with little crosslinking. In this case, the particles themselves may be multilayer in structure, produced by successive reaction with large excesses of alternating components. These multilayer-particles may then be reacted to form a single surface layer or a multilayer surface coating.

As will be appreciated by a skilled artisan, the number of layers forming a layered hydrogel can and will vary depending upon its intended use. In one embodiment, the layered substrate has from about 2 to about 100 distinctly formed layers. In another embodiment, the layered substrate has from about 5 to about 20 distinctly formed layers.

Typically, increasing the number of layers forming the hydrogel will increase its density along the surface, which will concomitantly, increase the hydrogel's protein rejecting properties. In general, protein rejecting refers to the ability of the hydrogel to prevent interaction or adsorption with endogenous proteins for which the substrate is not specific. The hydrogel typically has a resistance to protein adsorption (i.e., the hydrogel is protein rejecting). In one embodiment, the hydrogel is from about 90 percent to about 99 percent protein rejecting. In another embodiment, the hydrogel is at least about 95 percent protein rejecting. In yet another embodiment the hydrogel is at least about 99 percent protein rejecting.

Suitable components forming the layers of the hydrogel include any of the polymers, proteins, therapeutic molecules, and adhesion promoting peptides described herein or otherwise known in the art. Non-limiting examples of such hydrogels are set-forth in Table A.

TABLE A

| Polymer | Protein | Other Agent |
|---|---|---|
| poly(ethylene glycol) | Apo AI | anti-inflammatory agent |
| poly(ethylene glycol) | Apo AI | chemotherapeutic agent |
| poly(ethylene glycol) | Apo AI | endothelial cell migration promoting agent |
| poly(ethylene glycol) | Apo AI | angiogenesis promoting agent |
| poly(ethylene glycol) | Apo AI | anticoagulant |
| poly(ethylene glycol) | Apo AI | antibacterial agent |
| poly(ethylene glycol) | Apo AI | antiparasitic agent |
| poly(ethylene glycol) | Apo AI | antifungal agent |
| poly(ethylene glycol) | Apo AI | antiviral agent |
| poly(ethylene glycol) | Apo AI | analgesic agent |
| poly(ethylene glycol) | Apo AI | local anesthetic |
| poly(ethylene glycol) | Apo AI | immunomodulatory agent |
| poly(ethylene glycol) | Apo AI | cell adhesion promoting agent |
| poly(ethylene glycol) | Apo AI | enzyme that converts inactive precursor to active molecule |
| poly(ethylene glycol) | Apo AI | chemotherapeutic agent and immunomodulatory agent |
| poly(ethylene glycol) | Apo AI | chemotherapeutic agent and analgesic agent |
| poly(ethylene glycol) | Apo AI | anti-inflammatory agent and analgesic agent |
| poly(ethylene glycol) | Apo AI | cell adhesion promoting agent and angiogenesis promoting agent |
| poly(ethylene glycol) | Apo AI | cell adhesion promoting agent and endothelial cell migration promoting agent |
| poly(ethylene glycol) | Apo AI | cell adhesion promoting agent and enzyme that converts inactive precursor to active molecule |
| poly(ethylene glycol) | Apo AI | chemotherapeutic agent and enzyme that converts inactive precursor to active molecule |
| poly(ethylene glycol) | Apo B-100 | anti-inflammatory agent |
| poly(ethylene glycol) | Apo B-100 | chemotherapeutic agent |
| poly(ethylene glycol) | Apo B-100 | endothelial cell migration promoting agent |
| poly(ethylene glycol) | Apo B-100 | angiogenesis promoting agent |
| poly(ethylene glycol) | Apo B-100 | anticoagulant |
| poly(ethylene glycol) | Apo B-100 | antibacterial agent |
| poly(ethylene glycol) | Apo B-100 | antiparasitic agent |
| poly(ethylene glycol) | Apo B-100 | antifungal agent |
| poly(ethylene glycol) | Apo B-100 | antiviral agent |
| poly(ethylene glycol) | Apo B-100 | analgesic agent |
| poly(ethylene glycol) | Apo B-100 | local anesthetic |

TABLE A-continued

| Polymer | Protein | Other Agent |
|---|---|---|
| poly(ethylene glycol) | Apo B-100 | immunomodulatory agent |
| poly(ethylene glycol) | Apo B-100 | cell adhesion promoting agent |
| poly(ethylene glycol) | Apo B-100 | enzyme that converts inactive precursor to active molecule |
| poly(ethylene glycol) | Apo B-100 | chemotherapeutic agent and immunomodulatory agent |
| poly(ethylene glycol) | Apo B-100 | chemotherapeutic agent and analgesic agent |
| poly(ethylene glycol) | Apo B-100 | anti-inflammatory agent and analgesic agent |
| poly(ethylene glycol) | Apo B-100 | cell adhesion promoting agent and angiogenesis promoting agent |
| poly(ethylene glycol) | Apo B-100 | cell adhesion promoting agent and endothelial cell migration promoting agent |
| poly(ethylene glycol) | Apo B-100 | cell adhesion promoting agent and enzyme that converts inactive precursor to active molecule |
| poly(ethylene glycol) | Apo B-100 | chemotherapeutic agent and enzyme that converts inactive precursor to active molecule |
| poly(ethylene oxide) | Apo AI | anti-inflammatory agent |
| poly(ethylene oxide) | Apo AI | chemotherapeutic agent |
| poly(ethylene oxide) | Apo AI | endothelial cell migration promoting agent |
| poly(ethylene oxide) | Apo AI | angiogenesis promoting agent |
| poly(ethylene oxide) | Apo AI | anticoagulant |
| poly(ethylene oxide) | Apo AI | antibacterial agent |
| poly(ethylene oxide) | Apo AI | antiparasitic agent |
| poly(ethylene oxide) | Apo AI | antifungal agent |
| poly(ethylene oxide) | Apo AI | antiviral agent |
| poly(ethylene oxide) | Apo AI | analgesic agent |
| poly(ethylene oxide) | Apo AI | local anesthetic |
| poly(ethylene oxide) | Apo AI | immunomodulatory agent |
| poly(ethylene oxide) | Apo AI | cell adhesion promoting agent |
| poly(ethylene oxide) | Apo AI | enzyme that converts inactive precursor to active molecule |
| poly(ethylene oxide) | Apo AI | chemotherapeutic agent and immunomodulatory agent |
| poly(ethylene oxide) | Apo AI | chemotherapeutic agent and analgesic agent |
| poly(ethylene oxide) | Apo AI | anti-inflammatory agent and analgesic agent |
| poly(ethylene oxide) | Apo AI | cell adhesion promoting agent and angiogenesis promoting agent |
| poly(ethylene oxide) | Apo AI | cell adhesion promoting agent and endothelial cell migration promoting agent |
| poly(ethylene oxide) | Apo AI | cell adhesion promoting agent and enzyme that converts inactive precursor to active molecule |
| poly(ethylene oxide) | Apo AI | chemotherapeutic agent and enzyme that converts inactive precursor to active molecule |
| poly(ethylene oxide) | Apo B-100 | anti-inflammatory agent |
| poly(ethylene oxide) | Apo B-100 | chemotherapeutic agent |
| poly(ethylene oxide) | Apo B-100 | endothelial cell migration promoting agent |
| poly(ethylene oxide) | Apo B-100 | angiogenesis promoting agent |
| poly(ethylene oxide) | Apo B-100 | anticoagulant |
| poly(ethylene oxide) | Apo B-100 | antibacterial agent |
| poly(ethylene oxide) | Apo B-100 | antiparasitic agent |
| poly(ethylene oxide) | Apo B-100 | antifungal agent |
| poly(ethylene oxide) | Apo B-100 | antiviral agent |
| poly(ethylene oxide) | Apo B-100 | analgesic agent |
| poly(ethylene oxide) | Apo B-100 | local anesthetic |
| poly(ethylene oxide) | Apo B-100 | immunomodulatory agent |
| poly(ethylene oxide) | Apo B-100 | cell adhesion promoting agent |
| poly(ethylene oxide) | Apo B-100 | enzyme that converts inactive precursor to active molecule |
| poly(ethylene oxide) | Apo B-100 | chemotherapeutic agent and immunomodulatory agent |
| poly(ethylene oxide) | Apo B-100 | anti-inflammatory agent and analgesic agent |
| poly(ethylene oxide) | Apo B-100 | cell adhesion promoting agent and angiogenesis promoting agent |

TABLE A-continued

| Polymer | Protein | Other Agent |
|---|---|---|
| poly(ethylene oxide) | Apo B-100 | cell adhesion promoting agent and endothelial cell migration promoting agent |
| poly(ethylene oxide) | Apo B-100 | cell adhesion promoting agent and enzyme that converts inactive precursor to active molecule |
| poly(ethylene oxide) | Apo B-100 | chemotherapeutic agent and enzyme that converts inactive precursor to active molecule |

The hydrogels or other substrates of the invention may be used in several applications, including applications described herein or otherwise known in the art. Typically, the hydrogels and other substrates of the invention will be biocompatible so that they may be utilized to treat a variety of indications in a subject. The subject may be a variety of mammals and will generally be a companion animal such as a dog or cat, or a zoo animal or farm animal (i.e., horse, cow, pig, sheep or goat). In an exemplary embodiment the subject will be a human. For therapeutic applications, the substrate will generally include a therapeutic molecule as detailed herein or otherwise known in the art. By way of non limiting examples, suitable applications include local application, either at the time of surgery or via injection into tissue, to prevent adhesion of tissues; to deliver bioactive compounds where release is effected more efficiently or at a more desirable rate or where tissue encapsulation could detrimentally affect or delay release; to prevent thrombus formation at blood vessel surfaces, for example, following angioplasty; to alter cellular attachment, especially to prevent cellular attachment, and therefore decrease metastasis of tumor cells; and to coat prosthetic implants such as heart valves and vascular grafts derived from processed tissues.

II. Surfaces Coated with Nanolayers

Another aspect of the invention encompasses surfaces coated with a substrate having a plurality of distinctly formed polymer and protein layers, or a substrate having a single layer comprised of polymer and protein. Suitable components for the substrates (i.e., polymer, protein, therapeutic molecules and adhesion promoting peptides) are described in section 1. The layers of a layered substrate will generally be thin, ranging from about 1 nm to about 10 microns. In a further embodiment, the layers of a layered substrate are less than 10 microns. The layers of a substrate may also be relatively dense to produce coatings with high protein rejection properties. In one embodiment, the coating is from about 90 percent to about 99 percent protein rejecting. In another embodiment, the coating is at least about 95 percent protein rejecting. In yet another embodiment the coating is at least about 99 percent protein rejecting.

In one embodiment, the substrate of the invention may be coated onto the surface of a medical device. The process for producing a surface coated with a plurality of cross-linked, distinctly-formed layers, of the invention, includes contacting a surface with a solution, the solution having a functional group that binds to the surface to form an activated surface. In one embodiment, the surface is activated by contacting the surface with 3-aminopropyltriethoxysilane thereby forming amine reactive groups on the surface. The activated surface is then contacted with a first water soluble polymer solution, the polymers having a first and a second reactive group, the functional group on the surface reacting with the first reactive group on the polymers to form a first water soluble polymer layer. The first water soluble polymer layer is then contacted with a protein solution, the protein solution having proteins with at least one lipid binding site and a first and a second functional group, the second reactive group on the polymers reacting with the first functional group on the proteins to form a protein layer cross-linked to the first water soluble polymer layer. The protein layer is then contacted with a second water soluble polymer solution, the polymers having a first and second reactive group, the first reactive group on the polymers reacting with the second functional group on the protein to form a polymer layer cross-linked to the protein layer. The process steps can be repeated to form a plurality of cross-linked, distinctly-formed layers. For more details, see the Examples.

The process for producing a surface coated with a single layer includes contacting a surface with a solution, the solution having a functional group that binds to the surface to form an activated surface. In one embodiment, the surface is activated by contacting the surface with 3-aminopropyltriethoxysilane thereby forming amine reactive groups on the surface. The activated surface is then contacted with a mixture comprising a water soluble polymer solution, the polymers having a first and a second reactive group. The functional group on the surface may react with the first reactive group on the polymers. The mixture also comprises a protein solution, the protein solution having proteins with at least one lipid binding site and a first and a second functional group, the second reactive group on the polymers reacting with the first functional group on the proteins to form a single layered substrate comprising a protein cross-linked water soluble polymer. For more details, see the Examples.

Suitable medical devices include cardiovascular devices, such as vascular grafts and stents, artificial blood vessels, artificial bone joints, such as hip joints, and scaffolds that support tissue growth in such anatomical structures as nerves, pancreas, eye and muscle. Other suitable medical devices include biosensors and percutaneous devices, such as catheters, that penetrate the skin and link a living body to a medical device, such as a kidney dialysis machine. The substrate may also be applied to contact lenses, intraocular lenses, ultrafiltration membranes, and containers for biological materials. Additionally, cell culture dishes, or portions thereof, may be treated to minimize adhesion of cells to the dish. Cell culture dishes treated in this manner only allow cell spreading in those areas which are not treated, when the cells are anchorage dependent cells, that must be anchored to a solid support in order to spread.

The substrate may be applied to the treatment of macrocapsular surfaces, such as those used for ultrafiltration, hemodialysis and non-microencapsulated immunoisolation of animal tissue. The surface may be in the form of a hollow fiber, a spiral module, a flat sheet or other configuration.

In another embodiment, the substrate may also be coated onto metal surfaces. Generally, the substrate may be used to coat conduits for the flow of biological fluids, devices in contact with biological fluids, including those devices that are implanted into humans or animals. The metals include stainless steel, silver, gold, and titanium, or surfaces with metal oxides such as iron oxide, titanium oxide and silicon oxide. Other materials include glass, silicon containing materials, cadmium, palladium, iron, nickel, cobalt, and copper.

The metals are coated with the substrate as a part of conduit or device manufacture, or are treated in situ, following assembly of the conduit or device, or as part of the normal operation of the device. The treatment may be applied by reaction from a liquid solution, or by spraying.

Another aspect of the invention includes a process of making a substrate having a therapeutic molecule non covalently bound to the substrate. The process includes derivatizing the end groups of a branched water soluble polymer to yield a reaction group, such as a vinyl sulfone group. The derivatized polymer is then contacted with a protein solution, the protein solution having a protein with at least one lipid binding site and functional amino or sulfhydryl groups. The reactive vinyl sulfone group the polymer reacts with the functional amino or sulfhydryl groups in the protein to form a substrate. Finally, the substrate is contacted with a therapeutic molecule under conditions such that the therapeutic molecule is non covalently conjugated to the substrate. The surface coated with a therapeutic molecule may be utilized in vivo to deliver a drug or drug producing enzyme to a subject. Suitable therapeutic molecules include any generally known in the art or described herein.

Suitable components coating the surface include any of the polymers, proteins, therapeutic molecules, and adhesion promoting peptides described herein or otherwise known in the art. Non-limiting examples of such coated surfaces are set-forth in Table B.

TABLE B

| Surface | Polymer layer of coating | Protein layer of coating | Other agent in coating |
|---|---|---|---|
| plastic | poly(ethylene glycol) | Apo AI | anti-inflammatory agent |
| plastic | poly(ethylene glycol) | Apo AI | chemotherapeutic agent |
| plastic | poly(ethylene glycol) | Apo AI | angiogenesis promoting agent |
| plastic | poly(ethylene glycol) | Apo AI | anticoagulant |
| plastic | poly(ethylene glycol) | Apo AI | antibacterial agent |
| plastic | poly(ethylene glycol) | Apo AI | antiviral agent |
| plastic | poly(ethylene glycol) | Apo AI | analgesic agent |
| plastic | poly(ethylene glycol) | Apo AI | local anesthetic |
| plastic | poly(ethylene glycol) | Apo AI | immunomodulatory agent |
| plastic | poly(ethylene glycol) | Apo AI | cell adhesion promoting agent |
| plastic | poly(ethylene glycol) | Apo AI | activating enzyme |
| plastic | poly(ethylene glycol) | Apo AI | chemotherapeutic agent and analgesic agent |
| plastic | poly(ethylene glycol) | Apo AI | anti-inflammatory agent and analgesic agent |
| plastic | poly(ethylene glycol) | Apo AI | cell adhesion promoting agent and angiogenesis promoting agent |
| plastic | poly(ethylene glycol) | Apo AI | cell adhesion promoting agent and activating enzyme |
| plastic | poly(ethylene oxide) | Apo AI | anti-inflammatory agent |
| plastic | poly(ethylene oxide) | Apo AI | chemotherapeutic agent |

TABLE B-continued

| Surface | Polymer layer of coating | Protein layer of coating | Other agent in coating |
|---|---|---|---|
| plastic | poly(ethylene oxide) | Apo AI | angiogenesis promoting agent |
| plastic | poly(ethylene oxide) | Apo AI | anticoagulant |
| plastic | poly(ethylene oxide) | Apo AI | antibacterial agent |
| plastic | poly(ethylene oxide) | Apo AI | antiviral agent |
| plastic | poly(ethylene oxide) | Apo AI | analgesic agent |
| plastic | poly(ethylene oxide) | Apo AI | local anesthetic |
| plastic | poly(ethylene oxide) | Apo AI | immunomodulatory agent |
| plastic | poly(ethylene oxide) | Apo AI | cell adhesion promoting agent |
| plastic | poly(ethylene oxide) | Apo AI | activating enzyme |
| plastic | poly(ethylene oxide) | Apo AI | chemotherapeutic agent and analgesic agent |
| plastic | poly(ethylene oxide) | Apo AI | anti-inflammatory agent and analgesic agent |
| plastic | poly(ethylene oxide) | Apo AI | cell adhesion promoting agent and angiogenesis promoting agent |
| plastic | poly(ethylene oxide) | Apo AI | cell adhesion promoting agent and activating enzyme |
| plastic | poly(ethylene glycol) | Apo B-100 | anti-inflammatory agent |
| plastic | poly(ethylene glycol) | Apo B-100 | chemotherapeutic agent |
| plastic | poly(ethylene glycol) | Apo B-100 | angiogenesis promoting agent |
| plastic | poly(ethylene glycol) | Apo B-100 | anticoagulant |
| plastic | poly(ethylene glycol) | Apo B-100 | antibacterial agent |
| plastic | poly(ethylene glycol) | Apo B-100 | antiviral agent |
| plastic | poly(ethylene glycol) | Apo B-100 | analgesic agent |
| plastic | poly(ethylene glycol) | Apo B-100 | local anesthetic |
| plastic | poly(ethylene glycol) | Apo B-100 | immunomodulatory agent |
| plastic | poly(ethylene glycol) | Apo B-100 | cell adhesion promoting agent |
| plastic | poly(ethylene glycol) | Apo B-100 | activating enzyme |
| plastic | poly(ethylene glycol) | Apo B-100 | chemotherapeutic agent and analgesic agent |
| plastic | poly(ethylene glycol) | Apo B-100 | anti-inflammatory agent and analgesic agent |
| plastic | poly(ethylene glycol) | Apo B-100 | cell adhesion promoting agent and angiogenesis promoting agent |
| plastic | poly(ethylene glycol) | Apo B-100 | cell adhesion promoting agent and activating enzyme |
| plastic | poly(ethylene oxide) | Apo B-100 | anti-inflammatory agent |
| plastic | poly(ethylene oxide) | Apo B-100 | chemotherapeutic agent |
| plastic | poly(ethylene oxide) | Apo B-100 | angiogenesis promoting agent |
| plastic | poly(ethylene oxide) | Apo B-100 | anticoagulant |
| plastic | poly(ethylene oxide) | Apo B-100 | antibacterial agent |
| plastic | poly(ethylene oxide) | Apo B-100 | antiviral agent |
| plastic | poly(ethylene oxide) | Apo B-100 | analgesic agent |
| plastic | poly(ethylene oxide) | Apo B-100 | local anesthetic |
| plastic | poly(ethylene oxide) | Apo B-100 | immunomodulatory agent |
| plastic | poly(ethylene oxide) | Apo B-100 | cell adhesion promoting agent |
| plastic | poly(ethylene oxide) | Apo B-100 | activating enzyme |
| plastic | poly(ethylene oxide) | Apo B-100 | chemotherapeutic agent and analgesic agent |
| plastic | poly(ethylene oxide) | Apo B-100 | anti-inflammatory agent and analgesic agent |
| plastic | poly(ethylene oxide) | Apo B-100 | cell adhesion promoting agent and angiogenesis promoting agent |
| plastic | poly(ethylene oxide) | Apo B-100 | cell adhesion promoting agent and activating enzyme |
| metal | poly(ethylene glycol) | Apo AI | anti-inflammatory agent |
| metal | poly(ethylene glycol) | Apo AI | chemotherapeutic agent |
| metal | poly(ethylene glycol) | Apo AI | angiogenesis promoting agent |
| metal | poly(ethylene glycol) | Apo AI | anticoagulant |
| metal | poly(ethylene glycol) | Apo AI | antibacterial agent |
| metal | poly(ethylene glycol) | Apo AI | antiviral agent |
| metal | poly(ethylene glycol) | Apo AI | analgesic agent |
| metal | poly(ethylene glycol) | Apo AI | local anesthetic |
| metal | poly(ethylene glycol) | Apo AI | immunomodulatory agent |
| metal | poly(ethylene glycol) | Apo AI | cell adhesion promoting agent |
| metal | poly(ethylene glycol) | Apo AI | activating enzyme |
| metal | poly(ethylene glycol) | Apo AI | chemotherapeutic agent and analgesic agent |
| metal | poly(ethylene glycol) | Apo AI | anti-inflammatory agent and analgesic agent |
| metal | poly(ethylene glycol) | Apo AI | cell adhesion promoting agent and angiogenesis promoting agent |

TABLE B-continued

| Surface | Polymer layer of coating | Protein layer of coating | Other agent in coating |
|---|---|---|---|
| metal | poly(ethylene glycol) | Apo AI | cell adhesion promoting agent and activating enzyme |
| metal | poly(ethylene oxide) | Apo AI | anti-inflammatory agent |
| metal | poly(ethylene oxide) | Apo AI | chemotherapeutic agent |
| metal | poly(ethylene oxide) | Apo AI | angiogenesis promoting agent |
| metal | poly(ethylene oxide) | Apo AI | anticoagulant |
| metal | poly(ethylene oxide) | Apo AI | antibacterial agent |
| metal | poly(ethylene oxide) | Apo AI | antiviral agent |
| metal | poly(ethylene oxide) | Apo AI | analgesic agent |
| metal | poly(ethylene oxide) | Apo AI | local anesthetic |
| metal | poly(ethylene oxide) | Apo AI | immunomodulatory agent |
| metal | poly(ethylene oxide) | Apo AI | cell adhesion promoting agent |
| metal | poly(ethylene oxide) | Apo AI | activating enzyme |
| metal | poly(ethylene oxide) | Apo AI | chemotherapeutic agent and analgesic agent |
| metal | poly(ethylene oxide) | Apo AI | anti-inflammatory agent and analgesic agent |
| metal | poly(ethylene oxide) | Apo AI | cell adhesion promoting agent and angiogenesis promoting agent |
| metal | poly(ethylene oxide) | Apo AI | cell adhesion promoting agent and activating enzyme |
| metal | poly(ethylene glycol) | Apo B-100 | anti-inflammatory agent |
| metal | poly(ethylene glycol) | Apo B-100 | chemotherapeutic agent |
| metal | poly(ethylene glycol) | Apo B-100 | angiogenesis promoting agent |
| metal | poly(ethylene glycol) | Apo B-100 | anticoagulant |
| metal | poly(ethylene glycol) | Apo B-100 | antibacterial agent |
| metal | poly(ethylene glycol) | Apo B-100 | antiviral agent |
| metal | poly(ethylene glycol) | Apo B-100 | analgesic agent |
| metal | poly(ethylene glycol) | Apo B-100 | local anesthetic |
| metal | poly(ethylene glycol) | Apo B-100 | immunomodulatory agent |
| metal | poly(ethylene glycol) | Apo B-100 | cell adhesion promoting agent |
| metal | poly(ethylene glycol) | Apo B-100 | activating enzyme |
| metal | poly(ethylene glycol) | Apo B-100 | chemotherapeutic agent and analgesic agent |
| metal | poly(ethylene glycol) | Apo B-100 | anti-inflammatory agent and analgesic agent |
| metal | poly(ethylene glycol) | Apo B-100 | cell adhesion promoting agent and angiogenesis promoting agent |
| metal | poly(ethylene glycol) | Apo B-100 | cell adhesion promoting agent and activating enzyme |
| metal | poly(ethylene oxide) | Apo B-100 | anti-inflammatory agent |
| metal | poly(ethylene oxide) | Apo B-100 | chemotherapeutic agent |
| metal | poly(ethylene oxide) | Apo B-100 | angiogenesis promoting agent |
| metal | poly(ethylene oxide) | Apo B-100 | anticoagulant |
| metal | poly(ethylene oxide) | Apo B-100 | antibacterial agent |
| metal | poly(ethylene oxide) | Apo B-100 | antiviral agent |
| metal | poly(ethylene oxide) | Apo B-100 | analgesic agent |
| metal | poly(ethylene oxide) | Apo B-100 | local anesthetic |
| metal | poly(ethylene oxide) | Apo B-100 | immunomodulatory agent |
| metal | poly(ethylene oxide) | Apo B-100 | cell adhesion promoting agent |
| metal | poly(ethylene oxide) | Apo B-100 | activating enzyme |
| metal | poly(ethylene oxide) | Apo B-100 | chemotherapeutic agent and analgesic agent |
| metal | poly(ethylene oxide) | Apo B-100 | anti-inflammatory agent and analgesic agent |
| metal | poly(ethylene oxide) | Apo B-100 | cell adhesion promoting agent and angiogenesis promoting agent |
| metal | poly(ethylene oxide) | Apo B-100 | cell adhesion promoting agent and activating enzyme |
| glass or silica | poly(ethylene glycol) | Apo AI | anti-inflammatory agent |
| glass or silica | poly(ethylene glycol) | Apo AI | chemotherapeutic agent |
| glass or silica | poly(ethylene glycol) | Apo AI | angiogenesis promoting agent |
| glass or silica | poly(ethylene glycol) | Apo AI | anticoagulant |
| glass or silica | poly(ethylene glycol) | Apo AI | antibacterial agent |
| glass or silica | poly(ethylene glycol) | Apo AI | antiviral agent |
| glass or silica | poly(ethylene glycol) | Apo AI | analgesic agent |
| glass or silica | poly(ethylene glycol) | Apo AI | local anesthetic |
| glass or silica | poly(ethylene glycol) | Apo AI | immunomodulatory agent |
| glass or silica | poly(ethylene glycol) | Apo AI | cell adhesion promoting agent |
| glass or silica | poly(ethylene glycol) | Apo AI | activating enzyme |
| glass or silica | poly(ethylene glycol) | Apo AI | chemotherapeutic agent and analgesic agent |
| glass or silica | poly(ethylene glycol) | Apo AI | anti-inflammatory agent and analgesic agent |

TABLE B-continued

| Surface | Polymer layer of coating | Protein layer of coating | Other agent in coating |
|---|---|---|---|
| glass or silica | poly(ethylene glycol) | Apo AI | cell adhesion promoting agent and angiogenesis promoting agent |
| glass or silica | poly(ethylene glycol) | Apo AI | cell adhesion promoting agent and activating enzyme |
| glass or silica | poly(ethylene oxide) | Apo AI | anti-inflammatory agent |
| glass or silica | poly(ethylene oxide) | Apo AI | chemotherapeutic agent |
| glass or silica | poly(ethylene oxide) | Apo AI | angiogenesis promoting agent |
| glass or silica | poly(ethylene oxide) | Apo AI | anticoagulant |
| glass or silica | poly(ethylene oxide) | Apo AI | antibacterial agent |
| glass or silica | poly(ethylene oxide) | Apo AI | antiviral agent |
| glass or silica | poly(ethylene oxide) | Apo AI | analgesic agent |
| glass or silica | poly(ethylene oxide) | Apo AI | local anesthetic |
| glass or silica | poly(ethylene oxide) | Apo AI | immunomodulatory agent |
| glass or silica | poly(ethylene oxide) | Apo AI | cell adhesion promoting agent |
| glass or silica | poly(ethylene oxide) | Apo AI | activating enzyme |
| glass or silica | poly(ethylene oxide) | Apo AI | chemotherapeutic agent and analgesic agent |
| glass or silica | poly(ethylene oxide) | Apo AI | anti-inflammatory agent and analgesic agent |
| glass or silica | poly(ethylene oxide) | Apo AI | cell adhesion promoting agent and angiogenesis promoting agent |
| glass or silica | poly(ethylene oxide) | Apo AI | cell adhesion promoting agent and activating enzyme |
| glass or silica | poly(ethylene glycol) | Apo B-100 | anti-inflammatory agent |
| glass or silica | poly(ethylene glycol) | Apo B-100 | chemotherapeutic agent |
| glass or silica | poly(ethylene glycol) | Apo B-100 | angiogenesis promoting agent |
| glass or silica | poly(ethylene glycol) | Apo B-100 | anticoagulant |
| glass or silica | poly(ethylene glycol) | Apo B-100 | antibacterial agent |
| glass or silica | poly(ethylene glycol) | Apo B-100 | antiviral agent |
| glass or silica | poly(ethylene glycol) | Apo B-100 | analgesic agent |
| glass or silica | poly(ethylene glycol) | Apo B-100 | local anesthetic |
| glass or silica | poly(ethylene glycol) | Apo B-100 | immunomodulatory agent |
| glass or silica | poly(ethylene glycol) | Apo B-100 | cell adhesion promoting agent |
| glass or silica | poly(ethylene glycol) | Apo B-100 | activating enzyme |
| glass or silica | poly(ethylene glycol) | Apo B-100 | chemotherapeutic agent and analgesic agent |
| glass or silica | poly(ethylene glycol) | Apo B-100 | anti-inflammatory agent and analgesic agent |
| glass or silica | poly(ethylene glycol) | Apo B-100 | cell adhesion promoting agent and angiogenesis promoting agent |
| glass or silica | poly(ethylene glycol) | Apo B-100 | cell adhesion promoting agent and activating enzyme |
| glass or silica | poly(ethylene oxide) | Apo B-100 | anti-inflammatory agent |
| glass or silica | poly(ethylene oxide) | Apo B-100 | chemotherapeutic agent |
| glass or silica | poly(ethylene oxide) | Apo B-100 | angiogenesis promoting agent |
| glass or silica | poly(ethylene oxide) | Apo B-100 | anticoagulant |
| glass or silica | poly(ethylene oxide) | Apo B-100 | antibacterial agent |
| glass or silica | poly(ethylene oxide) | Apo B-100 | antiviral agent |
| glass or silica | poly(ethylene oxide) | Apo B-100 | analgesic agent |
| glass or silica | poly(ethylene oxide) | Apo B-100 | local anesthetic |
| glass or silica | poly(ethylene oxide) | Apo B-100 | immunomodulatory agent |
| glass or silica | poly(ethylene oxide) | Apo B-100 | cell adhesion promoting agent |
| glass or silica | poly(ethylene oxide) | Apo B-100 | activating enzyme |
| glass or silica | poly(ethylene oxide) | Apo B-100 | chemotherapeutic agent and analgesic agent |
| glass or silica | poly(ethylene oxide) | Apo B-100 | anti-inflammatory agent and analgesic agent |
| glass or silica | poly(ethylene oxide) | Apo B-100 | cell adhesion promoting agent and angiogenesis promoting agent |
| glass or silica | poly(ethylene oxide) | Apo B-100 | cell adhesion promoting agent and activating enzyme |

As various changes could be made in the above compounds, products and methods without departing from the scope of the invention, it is intended that all matter contained in the above description and in the examples given below, shall be interpreted as illustrative and not in a limiting sense.

EXAMPLES

Example 1

Layer-by-Layer Synthesis of Hydrogels Comprising PEG Polymers and PEG Crosslinkers with Attached RGD Peptide PEG Synthesis Conversion of the endgroups on PEG to Michael-type acceptors allows the addition of peptides or other biological factors to the materials via conjugate addition reactions. Vinyl sulfone endgroups provide high reactivity and a high specificity towards thiols at neutral pH, without a competing hydrolysis reaction. Additionally, reaction of vinyl sulfone with amines in a slightly basic environment is feasible, allowing for reaction of PEG with lysine groups in proteins.

PEG-vinylsulfone (PEG-VS) was synthesized from four-arm or eight-arm PEG (mol. wt. 10,000, Shearwater Polymers, Huntsville, Ala.) in four steps using a modification of the methods described by Morpurgo et al. (Bioconjugate Chemistry, 1996, 7: 363-368). In the first step, PEGmesylate was formed by the reaction of mesyl chloride with PEG under nitrogen. PEG (25 g) dissolved in 300 mL toluene was dried by azeotropic distillation until the final volume was 150 mL. After cooling, 50 mL of dichloromethane (DCM) was added to prevent precipitation of PEG. The solution was cooled on ice for 15 min, and 5.58 mL triethylamine (TEA, 2 equiv.) was added. Next, 3.10 mL methane sulfonyl chloride (2 equiv.) was added dropwise and allowed to react for 20 h. The TEA salt was filtered out and the total volume was reduced to approx. 20 mL by rotary evaporation. PEG was precipitated by addition of ice-cold diethyl ether, recovered by filtration, and dried under vacuum: $^1$H NMR ($CDCl_3$) 3.13 ppm (s, 3H, —$SO_2CH_3$), 3.61 ppm (PEG backbone), 4.35 ppm (t, 2H, —$CH_2OSO_2$—). In the second step, PEG-mesylate was reacted with β-mercaptoethanol to form PEG-hydroxyethylsulfide. The PEG-mesylate (15.5 g) was dissolved in 150 mL sodium borate buffer (50 mM, pH 8), 3.5 mL of 14.3 M β-mercaptoethanol (4 equiv.) was added, and the solution was allowed to react at reflux under nitrogen for 3 h. The PEG was extracted twice with DCM, and the volume was reduced to approx. 20 mL by rotary evaporation. PEG was precipitated by addition of ice-cold diethyl ether, recovered by filtration, and dried under vacuum: $^1$H NMR ($CDCl_3$) 2.72 ppm (t, 2H, —$CH_2S$—), 2.75 ppm (t, 2H, —$SCH_2$—), 3.61 ppm (PEG backbone). Next, the sulfide was oxidized using hydrogen peroxide to form PEG-hydroxyethylsulfone. PEG-hydroxyethylsulfide (12.79 g) was dissolved in 50 mL distilled water with 1.69 g sodium tungstate (0.5 equiv.). The solution was cooled to near 0° C. and reacted with 2.09 mL 30% hydrogen peroxide (2 equiv.) overnight on ice. The PEG was extracted twice with DCM. The total volume of DCM was reduced to approx. 20 mL by rotary evaporation. PEG was precipitated by addition of ice-cold diethyl ether, recovered by filtration, and dried under vacuum: $^1$H NMR ($CDCl_3$) 3.32 ppm (t, 2H, —$CH_2SO_2$—), 3.39 ppm (t, 2H, —$SO_2CH_2$—), 3.61 ppm (PEG backbone), 3.92 ppm (t, 2H, —$OCH_2CH_2SO_2$—), 4.03 ppm (t, 2H, —$SO_2CH_2CH_2OH$). In the final step, the hydroxyethylsulfone was converted to a vinyl sulfone. PEG-hydroxyethylsulfone (7.97 g) was dried by azeotropic distillation in toluene until the final volume was 150 mL. After cooling, 50 mL DCM was added to prevent precipitation of the PEG. The solution was cooled on ice for 15 min, then 2.68 mL TEA (3 equiv.) was added. Next, 0.75 mL mesyl chloride (1.5 equiv.) was added dropwise, and the solution was allowed to react for 24 h. Another 2.68 mL TEA (3 equiv.) was added, followed by 0.75 mL mesyl chloride (1.5 equiv. added dropwise), and the reaction was carried out overnight. The TEA salt was filtered out and the total volume was reduced to approx. 20 mL by rotary evaporation. PEG was precipitated by addition of ice-cold diethyl ether, recovered by filtration, and dried under vacuum: $^1$H NMR ($CDCl_3$) 3.61 ppm (PEG backbone), 6.04 ppm (d, 1H, =$CH_2$), 6.35 ppm (d, 1H, =$CH_2$), 6.79 ppm (q, 1H, —$SO_2CH$=).

PEG-diamine was synthesized as described by Elbert and Hubbell (Biomacromolecules 2001, 2: 430-441) from poly (ethylene glycol), mol. wt. 3400 (24 g, Sigma, St. Louis, Mo., USA): $^1$H NMR ($CDCl_3$) 2.85 ppm (t, 4H, —$CH_2$—$NH_2$), 3.65 ppm (PEG backbone).

Hydrogel Synthesis

Hydrogels were formed layer-by-layer by conjugate addition reactions between PEG-VS and PEG-diamine. First, the surface of the substrate was activated to create reactive amine groups. Clean glass coverslips were incubated in 2% 3-aminopropyltriethoxysilane in dry acetone solution for one hour with gentle shaking. The aminophase coverslips were then cured at 100° C. for a 3 h, and stored in a clean Petri dish until use. The activated substrates were incubated with a solution containing 1% eight-arm PEG-VS overnight at pH 8.5 and 37° C. The substrates were subsequently incubated with a solution of 1% PEG-diamine (mol. wt. 3400, Shearwater Polymers) for 1 h at 37° C. This two-step process was repeated to create multiple layers (one layer comprises PEG-VS+PEG-diamine). Between incubations with PEG-VS or PEG-diamine, the surfaces were washed six times with PBS. After the formation of five layers, the substrates were incubated with PEG-VS for 1 h at 37° C. A cell adhesion-promoting peptide, RGD peptide, was then added via a conjugation reaction between the free thiol group in the cysteine residue of the peptide and vinylsulfone groups in the PEG coating.

The RGD peptide acetyl-GCGYGRGDSPG [SEQ ID NO. 5] was synthesized on an Applied Biosystems ABI 433A peptide synthesizer. The peptide was purified by C18 chromatography and analyzed by MALDI-TOF mass spectrometry. The peptide was dissolved in phosphate buffered saline (pH 8.5) solution at a concentration of 0.1 mg/mL. PEG-coated coverslips were placed into wells of a 24 well plate and were incubated with the 1 mL of peptide solution for 10 min. at 37° C. and then rinsed with PBS extensively.

Cell Adhesion Assay

Human Umbilical Vein Endothelial Cells (HUVEC, Clonetics) were grown in endothelial cell growth medium (EGM, Clonetics) on tissue culture polystyrene at 37° C. and 5% $CO_2$. The cells were washed with 1 mL of 0.05% trypsin/0.02% EDTA solution (GIBCO BRL) and removed from culture flasks by adding 3 mL of the trypsin solution. Cells were seeded onto the coated substrates at $1\times10^4$ cells/cm$^2$ in 1 mL in the medium containing serum proteins. Cells on the surfaces were imaged by phase contrast microscopy and the number of cells was counted manually. As shown in FIG. 1, addition of the RGD peptide to the PEG hydrogel restored HUVEC adhesion, indicating that reduction of cell adhesion on the PEG hydrogel alone was not due to a toxic effect.

Example 2

Layer-by-Layer Synthesis of Hydrogels Comprising PEG Polymers and Albumin Crosslinkers Hydrogels were formed layer-by-layer by conjugate addition reactions between PEG-VS and the amino groups of the lysine residues of albumin. To activate the substrate, glass chips (Microvacuum, Inc., Budapest, Hungary) coated with a $Si/Ti/O_2$ waveguide layer were cleaned by immersion in a 3:1 sulfuric acid and hydrogen peroxide solution for 5 minutes and rinsed thoroughly in deionized water. The cleaned waveguide chips were silanized with 2% (v/v) 3-aminopropyltriethoxysilane in acetone for 15 minutes, dried at 80° C. for 1 hour, and stored in pH 7.4 phosphate buffered saline until use.

Four-arm or eight-arm PEG-VS was synthesized from 4-arm or 8-arm PEG as described in Example 1. A 3% solution of eight-arm PEG-VS in PBS at pH 8.5 was perfused over the surface of the waveguide chip for 24 hours at a rate of 0.05 ml/min and 37° C. while changes in thickness and density were monitored in real time with optical waveguide light-mode spectroscopy (OWLS). The solution was switched to PBS at pH 8.5 and the flow rate was increased to 0.35 ml/min to wash the surface for 1 hour and ensure the removal of any unreacted PEG. A 3% solution of bovine serum albumin in PBS at pH 8.5 was then perfused over the surface for 24 hours at a 0.05 ml/min and 37° C. The solution was switched to PBS at pH 8.5 and the flow rate was increased to 0.35 ml/min to wash the surface for 1 hour. The sequential perfusion of PEG-VS and albumin was repeated two more times, to create a total of three layers. The OWLS technique revealed that the first layer had a thickness of 1.97 nm and a density of 392 $ng/cm^2$. Following addition of the second layer, the coating thickness increased to 2.59 nm and the density increased to 507 $ng/cm^2$. Upon addition of the third layer, the coating thickness increased to 2.85 nm and the density increased to 536 $ng/cm^2$.

Example 3

Layer-by-Layer Synthesis of Hydrogels Comprising PEG Polymers and rHDL Particle Crosslinkers Formation of rHDL Particles Apolipoprotein A1 (ApoA1) is the major protein of HDL particles, which are complexes of apolipoproteins and phospholipids. The cDNA encoding human ApoAI was transferred from pDNR-LIB (ATCC, Manassas, Va.) into the expression vector pET-14b (Novagen, San Diego, Calif.) with NdeI and XhoI. A single cysteine residue was added to the N-terminus of ApoA1 by PCR cloning [SEQ ID NO. 3], as well as an N-terminal $His_6$ tag. (Another version of ApoA1 was produced with a cysteine residue added to the C-terminus as well as the N-terminus [SEQ ID NO. 4]). The vector with the correct sequence was used for protein expression. The vector was transfected into Rosetta2 *E. coli* cells (Novagen). The cells were grown to an $OD_{600}$ of 0.9-1.0 in LB medium with 100 μg/ml ampicillin. Protein expression was induced with 1 mM IPTG for 4 h. Cells were harvested by centrifugation for 20 min at 6000×g at 4° C. and resuspended in PBS. The cells were lysed using lysozyme and sonication, and the lysate was centrifuged at 50,000×g for 45 min at 4° C. The protein was purified via the $His_6$ tag and removed from the $Ni^+$ column with 350 mM imidazole. SDS-PAGE gel revealed the presence of the expressed recombinant protein at about 28 kDA, the expected mol. wt.

Phosphatidylcholine (PC) and sphingosine 1-phosphate (S1P, Biomol, Plymouth Meeting, Pa.) stock solutions are dissolved in chloroform/methanol (1:1) and combined to produce the following ratios of PC to S1P: 9:1, 3:1, 1:1, 1:3, and 1:9. The organic solvent is removed by rotary evaporation. Tris buffer (10 mM Tris-HCl, pH 8.0, 150 mM NaCl, 0.01% EDTA) is added to produce a final lipid concentration between 2 and 20 mg/mL. The mixture is sonicated on ice under nitrogen for 3 min, cooled on ice for 2 min, and then the cycle of sonicating and cooling is repeated five times. Purified recombinant ApoAI protein, containing the N-terminal His tag, is added to the lipid mixture and incubated at 37° C. for 1 h. The resulting sample is centrifuged at 15,000 rpm for 1 h at 15° C. and the rHDL particles in the supernatant are purified using metal affinity chromatography. The particles are eluted from the column, using thrombin at a ratio of 1:2000 (enzyme:protein) for 16 h at 20° C. This reaction is dialyzed in standard Tris buffer and particle size is determined using a 90 Plus Particle Size Analyzer (Brookhaven Instruments Corporation, Holtzville, N.Y.).

Hydrogels are formed layer-by-layer as described in Example 2, except that rHDL particles are substituted for albumin.

Example 4

Synthesis of Layer-by-Layer Coatings Using Nanoparticles

Nanoparticles were fabricated by incubating linear PEG molecules with a protein. PEG-diacrylate was synthesized as described by Elbert and Hubbell (Biomacromolecules 2001, 2: 430-441). PEG-diacrylate and albumin were mixed in PBS with a 1:1 molar ratio of PEG-diacrylate to albumin amines and incubated at 37° C. overnight. The resultant particles had mean diameters of 42.6±20.2 nm, as measured with a 90 Plus Particle Size Analyzer (Brookhaven Instruments Corporation, Holtzville, N.Y.). Nanoparticles are also formed by incubating PEG-diacrylate with rHDL particles (see Example 3) under the same conditions.

Glass OWLS chips are silanized with 2% (v/v) 3-aminopropyltriethoxysilane. The solution of albumin nanoparticles at pH 7.4 is perfused over the surface of the waveguide chip for 24 hours at a flow rate of 0.05 ml/min and 37° C. Changes in thickness and density are monitored in real time using OWLS. The flow solution is switched to PBS at pH 7.4 and the flow rate is increased to 0.35 ml/min to wash the surface for 1 hour. Additional layers of nanoparticles may be added by repeated these steps. Thickness and density of the layer(s) are measured. Coatings can also be made using solutions of rHDL nanoparticles.

Example 5

Synthesis and Characterization of Albumin Hydrogels

Synthesis of Hydrogels

Hydrogels were formed by a conjugate addition reaction between eight-arm PEG-octavinylsulfone (PEG-OVS) and the following crosslinkers: (1) albumin (fatty acid-free bovine serum albumin, FAF-BSA), (2) PEG-diamine, (3) fibrinogen, or (4) dithiothreitol (DTT). DTT was dissolved in phosphate buffered saline (PBS; 137 mM NaCl, 8 mM $Na_2HPO_4.7H_2O$, 0.7 mM $CaCl_2$, 2.7 mM KCl, 1.5 mM $KH_2PO_4$, 0.5 mM $MgCl_2$; pH 7.4) at 0.3 mg per 10 μL PBS. All other precursors were dissolved in PBS by adding 10 mg solid to 50 μL PBS at pH 8.0 (assuming a volume change due to the dissolved precursors to be 1 μL per mg of solid, the precursors were nominally dissolved at 10 mg/60 μL). PEG-OVS was then mixed with crosslinking proteins at a 1:1 ratio of vinyl sulfone to accessible amino groups on the protein. Surface amines on albumin were estimated by analyzing the 3D crystal structures of the proteins. For albumin, 36 of the 59 lysines were accessible, while for fibrinogen 65 of 106 were accessible. Optimal ratios of reactants were then determined empirically for each crosslinker by forming gels with different ratios of each component, seeking to minimize the amount of gel swelling in PBS after crosslinking. For PEG-OVS/albumin gels, the final mixture consisted of 40 μL PEG-OVS (~6.6 mg) and 60 μL albumin (~10.0 mg). For PEG-OVS/PEG-diamine gels, 50 μL PEG-OVS (~8.3 mg) was mixed with 68 μL PEG-diamine (~11.3 mg). For PEG-OVS/fibrinogen, the final ratio was 20 μL PEG-OVS (~3.3 mg) to 50 μL fibrinogen (~8.3 mg). After mixing the precursors, gels were formed in tissue culture plate wells or between glass microscope slides. For the latter method, the solution (50 μL) was pipetted onto the center of a glass microscope slide made hydrophobic with SigmaCote (Sigma, St. Louis, Mo.). Another hydrophobic slide was clamped on top, using 0.7 mm thick Teflon spacers at the edges of the slides. The solution contacted only hydrophobic glass and formed a circular disc. The solutions were crosslinked in a 37° C. humidified incubator for 24 h. The gels were then swollen in PBS overnight.

Hydrogel Swelling

The swelling properties of the hydrogels were determined for the different crosslinkers. The hydrogels were swollen in PBS for 96 h and each gel was weighed to determine the swollen volume. Densities used in the calculation of volume fractions were: PBS, 1.017 g/mL; PEG, 1.199 g/mL; albumin, 1.364 g/mL; fibrinogen, 1.379 g/mL; and DTT, 1.000 g/mL. Gels crosslinked with proteins swelled less than gels crosslinked with bifunctional crosslinkers, indicating that at least some of the protein molecules served as elastically-active crosslink sites (FIG. 2).

Hydrogel Mesh Size

The mesh size of PEG-OVS/albumin hydrogels was investigated using a modified SDS-PAGE gel to characterize the migration of albumin through the PEG hydrogels. A 15% acrylamide gel was formed at the bottom of the casting chamber, with a spacer to form a well on the left side of the gel. After the acrylamide solidified, the PEG-OVS/albumin precursor solution was pipetted into the formed well. The casting stand was placed in a humidified 37° C. incubator for 24 h to crosslink the PEG gel. A 7% acrylamide gel was formed over the polymerized gels, followed by a stacking gel. A solution of bovine serum albumin (BSA) was loaded into the wells of the gel, which was run under standard conditions. The gel was stained with Coomassie Blue.

Figure 2:
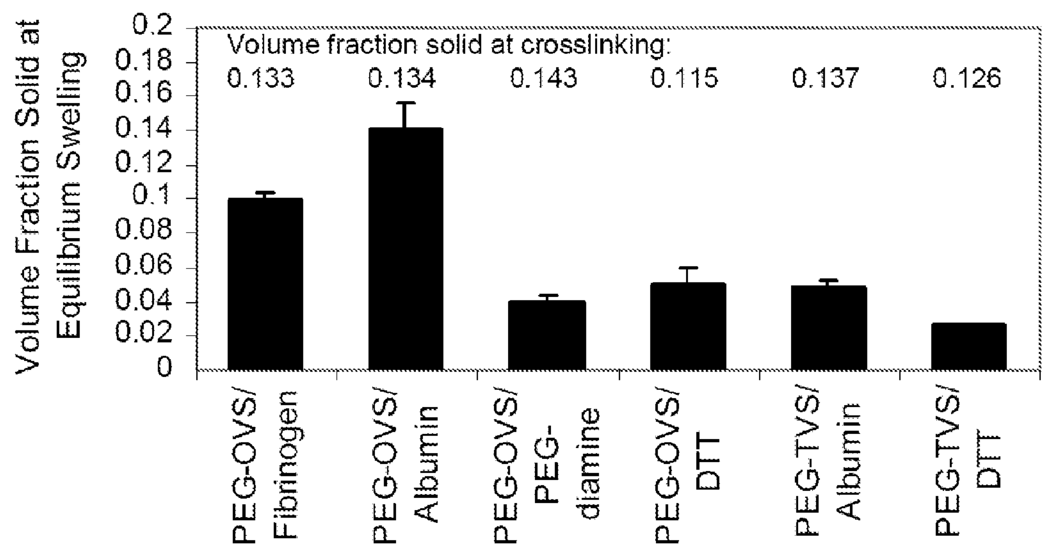
FIG. 2 depicts an image and a graph characterizing the hydrogel cross-link densities. A) PEG-octavinylsulfone (PEGOVS) or PEG-tetravinylsulfone (PEG-TVS) was crosslinked with albumin, fibrinogen, PEGdiamine (mol. wt. 3400), or DTT. The percent solid in each swollen gel was calculated after 4 days of swelling in PBS, pH 7.4. The hydrogels were crosslinked at the percent solids listed above each column. Data represent mean±standard deviation. B) A 15% SDS-PAGE gel was polymerized, with a spacer on the top left side of the chamber. After the spacer was removed, a thin layer of PEG-OVS/albumin precursor solution was pipetted into the formed well and crosslinked for 24 h. A 7% SDS-PAGE gel was then polymerized to fill the rest of the casting chamber. Bovine serum albumin (BSA; 20 μg in 20 μL) was loaded on the gel at the indicated locations. BSA did not pass through the PEG gel and accumulated above the hydrogel layer.
Figure 2:
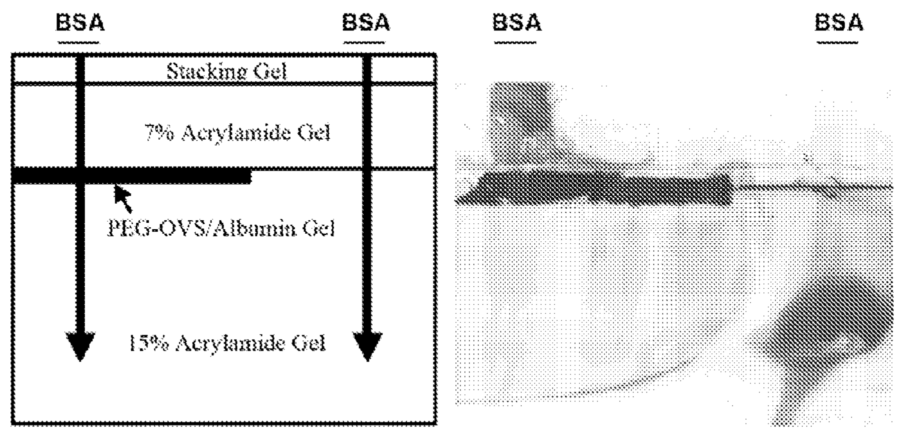

Albumin migration through the PEG hydrogel was hindered, resulting in an accumulation of albumin above the PEG layer (FIG. 2). Thus, the mesh size of the hydrogels, which is characterized by the radius of gyration of the polymer chains between elastically-active crosslinks, is less than or on the order of the radius of gyration of albumin (about 30 Å). The molecular weight markers aprotinin (6.5 kDa) and lysozyme (14.4 kDa) freely passed through the PEG hydrogel (data not shown).

S1P Loading of Hydrogels

Sphingosine 1-phosphate (S1P) is an angiogenic factor. During the early stages of angiogenesis, it promotes endothelial cell migration and proliferation, and during the later stages, it stimulates endothelial cell entubulation and stabilizes the newly formed vessels. PEG hydrogels were loaded with S1P using two methods: 'postloading' and 'preloading'. PEG hydrogels were 'postloaded' with S1P by passive diffusion, by incubating the previously formed gels with 500 μL of 10 μM S1P (5 nmol) in PBS containing 0.01% (w/v) FAF-BSA. The FAF-BSA in solution was necessary to solubilize the S1P, but the concentration of albumin in the loading solution was much lower than the concentration of albumin in the hydrogel (10% w/v). Following 24 h of incubation with S1P, the gels were washed in PBS twice for 1 h and then once for 24 h. For preloading, S1P was solubilized directly into the albumin solution used to crosslink the PEG-OVS. For this albumin was premixed with a solution of 5 nmol S1P. S1P-preloaded gels were washed in PBS twice for 1 h and then once for 24 h.

S1P Release from Postloaded Hydrogels

After washing in PBS, 150 μL S1P-loaded gels were placed into Eppendorf tubes containing 500 μL 0.4% FAF-BSA in PBS, which were vortexed for 24 h. An aliquot (5 μL) was removed from each tube and loaded on a silica TLC plate (Whatman, Inc., Clifton, N.J.). Aliquots (5 μL) of the first 1 h PBS wash and the 24 h PBS wash were also analyzed for each gel. The plates were developed in butanol:acetic acid:water (3:3:1). For visualization, the TLC plate was sprayed with ninhydrin reagent (0.2 g ninhydrin in 100 mL butanol) and heated.

Figure 3:
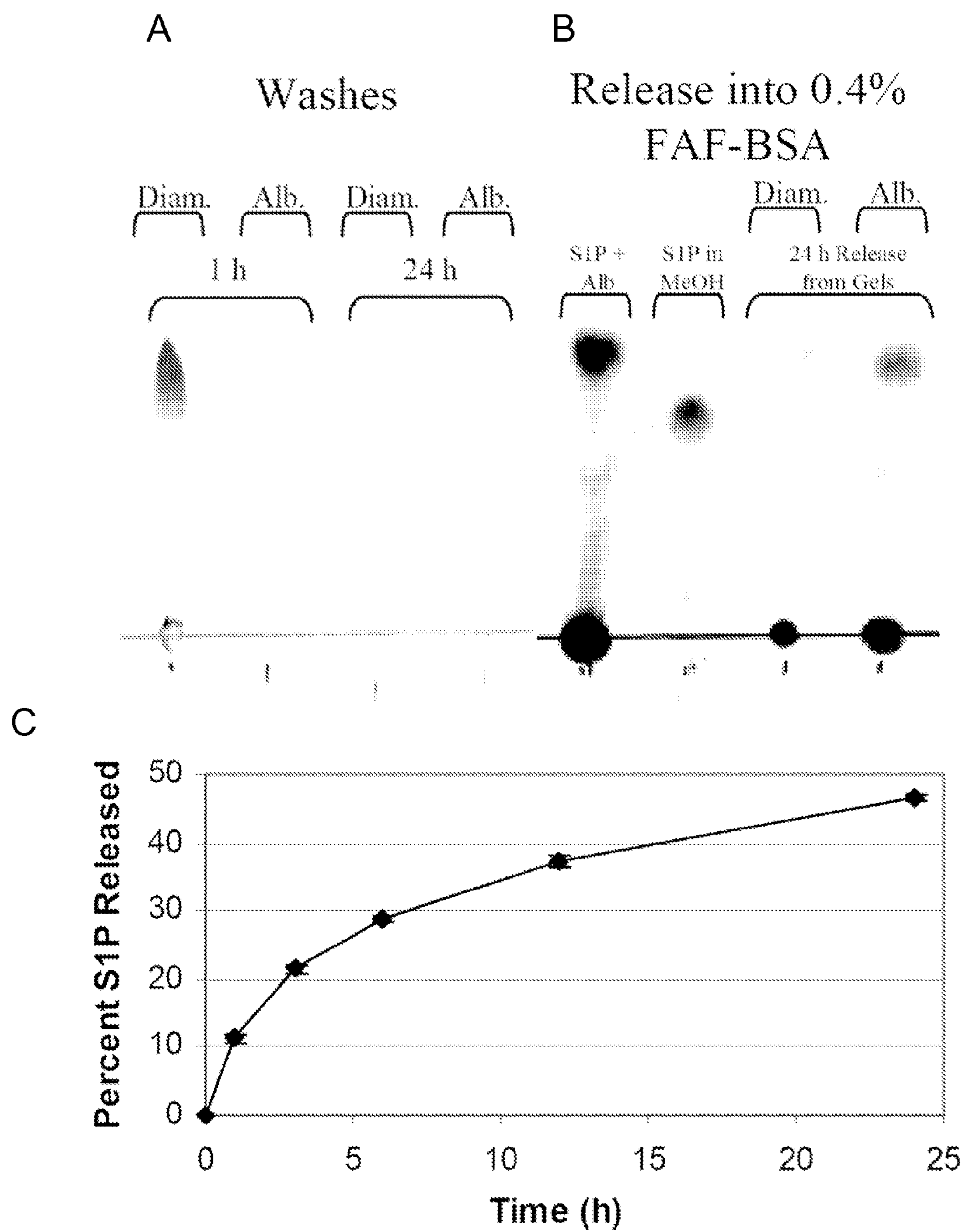
FIG. 3 depicts a series of images and a schematic of a graph illustrating the release of S1P from postloaded hydrogels. Panel (a) shows the release of S1P into the PBS washes, as analyzed by thin layer chromatography. Panel (b) presents the release of S1P into FAF-BSA solutions, as analyzed by thin layer chromatography. Panel (c) displays the mean release of $[^{32}P]$S1P from postloaded PEG-OVS/albumin gels over 24 h. Error bars represent standard deviations.

Most of the S1P was washed out of PEG-OVS/PEG-diamine hydrogels in the first 1 h wash with PBS, but PEG-OVS/albumin hydrogels retained the S1P during the PBS washes (FIG. 3*a*). When the hydrogels were placed into a solution containing 0.4% FAF-BSA, a large amount of S1P was released from the PEG-OVS/albumin hydrogels, but apparently little of the S1P remained in the PEG-OVS/PEG-diamine hydrogels to be released (FIG. 3*b*).

Radiolabeled S1P was produced to quantify loading and release of S1P from the postloaded PEG-OVS/albumin hydrogels. To label S1P with $^{32}$P, 10 μL of 10 mM sphingosine (BioMol, Plymouth Meeting, Pa.) in buffer A (25 mM Tris HCl, pH 7.4, 10% (v/v) glycerol, 0.05% Triton X-100, 1 mM DTT) containing 0.4% BSA was added to 80 μL sphingosine kinase (3.6 mg/mL in buffer A), and 90 μL buffer A. The reaction was started by adding 20 μL [$^{32}$P]ATP (100 μCi, 10 mM, MP Biomedicals, Irvine, Calif.) in 100 mM $MgCl_2$. The reaction was incubated overnight at 37° C. and stopped by the addition of 20 μL of 1 M HCl. Lipids were extracted with 800 μL chloroform/methanol/1 M HCl (100:200:1). After mixing, 240 μL chloroform and 240 μL 2 M KCl were added and the solution was centrifuged. The aqueous phase was removed, and the organic phase was extracted again by the addition of 400 μL 1:1 methanol/1 M HCl. The phases were separated by centrifugation. The organic phase was removed, dried under nitrogen flow, and dissolved in PBS containing FAF-BSA.

[$^{32}$P]S1P was dissolved in PBS containing 0.01% FAF-BSA and added to 50 μL PEG hydrogels in a 24-well plate for 24 h. The S1P-loaded hydrogels were washed twice in 1 mL PBS for 1 h (to remove unbound S1P) and a third time for 24 h. Next, 1.5 mL of platelet poor plasma (PPP) or PBS containing 0%, 0.4%, or 4% (w/v) FAF-BSA was added to the gels. The solutions were removed from the wells and replaced with fresh solutions at 1, 3, 6, 12, and 24 h and the release of [$^{32}$P]S1P was quantified by scintillation counting. The release at each time point is reported as a fraction of total S1P in each gel, which was determined by summing the amount of S1P in all wash and release solutions for each gel and the amount of S1P in each gel at the end of the experiment. PPP was obtained from human subjects with informed consent in accordance with Washington University Medical Center guidelines.

When PEG-OVS/albumin hydrogels were incubated with 1.5 mL of the 3.33 μM S1P solution, 59.1±3.1% of the [$^{32}$P]S1P was captured in the gel within 24 h. The gels were then washed thoroughly with PBS for 26 h, with 6.9±1.1% of the loaded [$^{32}$P]S1P was released into the wash solutions. PBS containing 0.4% FAF-BSA was added to the gels and controlled release of [$^{32}$P]S1P from the gels was observed, with 46.6±0.4% of the remaining S1P released over 24 h (FIG. 4*c*).

S1P Release from Postloaded Gels—In Vitro Scrape Wound Assay

An in vitro scrape wound assay was used to demonstrate that S1P released from the postloaded gels promoted endothelial cell migration. All cell culture reagents were purchased from Sigma (St. Louis, Mo.) unless otherwise noted. Human umbilical vein endothelial cells (HUVEC) were purchased from Clonetics, Inc (Walkersville, Md.) and cultured in MCDB 131 medium supplemented with 2% FBS, 10 ng/mL epidermal growth factor, 10 μg/mL heparin, 1.0 μg/mL hydrocortisone, 1% antibiotic-antimycotic (ABAM, 100×) solution (Invitrogen, Carlsbad, Calif.), and 6 mg/L bovine brain extract (Clonetics).

Cells from passage 5-7 were grown to confluence in a 6-well tissue culture plate and then switched to low serum medium (LSM; 0.1% FBS, 1% ABAM in MCDB 131 medium) with 10 ng/mL VEGF and 0.4% FAF-BSA 12 h prior to the start of the experiment (the VEGF was added to enhance cell survival in the low serum medium). A 1000 μL pipette tip was used to make a vertical and a horizontal scrape wound in each well, crossing near the middle of the well. Each well was washed 3× with PBS to remove non-adherent cells. At the start of the experiment, pictures were taken at 4× magnification on each arm of the scrape wound and 20 μL PEG gels were then added to the appropriate wells. The hydrogels were allowed to float freely in the medium. Pictures were taken again after 24 h, using calipers on the microscope to locate the same locations. Image-Pro Express software was used to define the initial scrape wound area and the number of cells within the wound area was counted manually.

Figure 4:
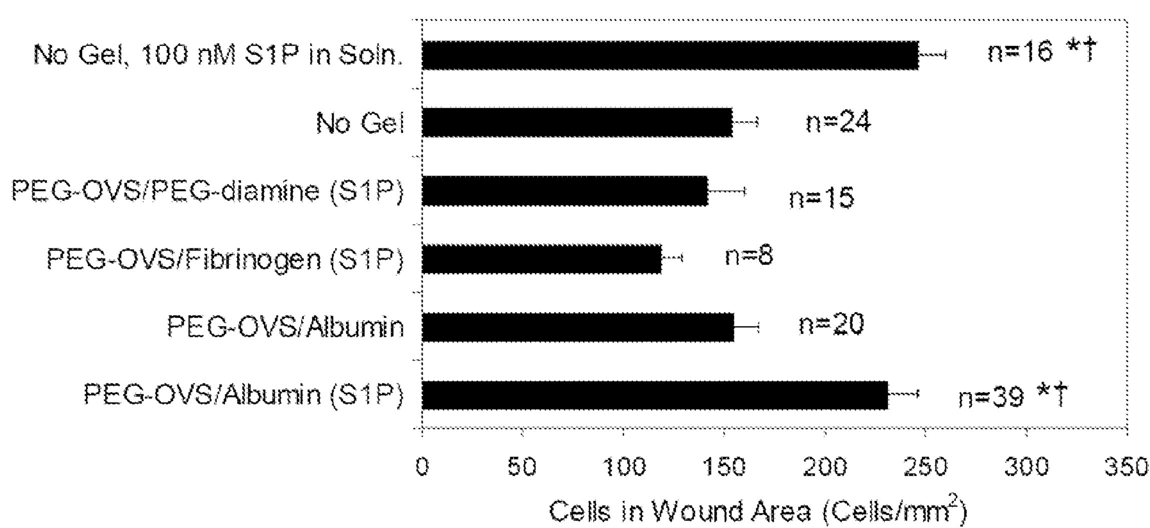
FIG. 4 depicts a schematic of a graph illustrating the migration of endothelial cells in response to released S1P as measured by the scrape wound assay. Postloaded PEG-OVS/albumin gels increased the amount of cell migration into the wound area to an extent similar to S1P in the medium. All other experimental conditions did not cause significant differences in cell migration into the wound area versus medium alone. In the column labels, '(S1P)' denotes S1P postloaded into the hydrogels. * Statistically significant difference vs. medium with no gel. † Statistically significant difference vs. PEG-OVS/albumin gels without S1P loading. Error bars represent SEM.

PEG-OVS/albumin gels postloaded with S1P significantly increased the number of endothelial cells that migrated into the scrape wound area by 24 h, compared to wells without gels, gels not loaded with S1P, or PEG-OVS/fibrinogen and PEG-OVS/PEG-diamine hydrogels postloaded with S1P (FIG. 4). Considering the results shown in FIG. 3*a*, the S1P loaded in the fibrinogen and diamine crosslinked hydrogels was likely removed during the PBS washing steps.

S1P Release from Postloaded Gels—Chorioallantoic Membrane (CAM) Assay

A chick CAM assay was used to demonstrate the ability of S1P-releasing hydrogels to induce angiogenesis in vivo. Embryonated chicken eggs were incubated blunt-end up in a 37° C. incubator. At embryonal day 6, the top of the egg was cracked and removed using tweezers to create a 1.5 cm diameter opening. The inner shell membrane was removed, exposing the CAM. A 20 μL PEG hydrogel was then placed onto the CAM. As controls, 50 ng bFGF or 50 ng S1P were spotted onto small pieces of Thermanox coverslips (Nunc), air dried and placed onto the CAM. The eggs were sealed with parafilm and returned to the incubator. After two days of incubation, the eggs were reopened and the degree of angiogenesis was visually assessed.

Figure 5:
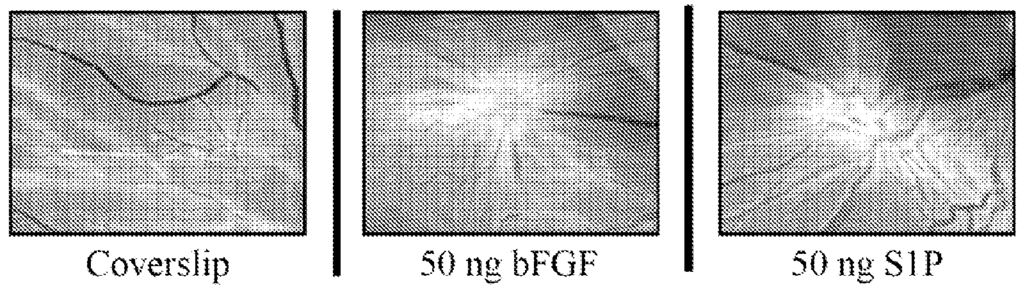
FIG. 5 depicts a series of images illustrating the angiogenic response to released S1P using the chorioallantoic membrane (CAM) assay. Panel (a) presents the control conditions. A strong angiogenic response was elicited by bFGF or S1P (characterized by the curvature of large vessels toward the point of stimulus). Panel (b) shows the angiogenic response in the presence of the different hydrogels.
Figure 5:
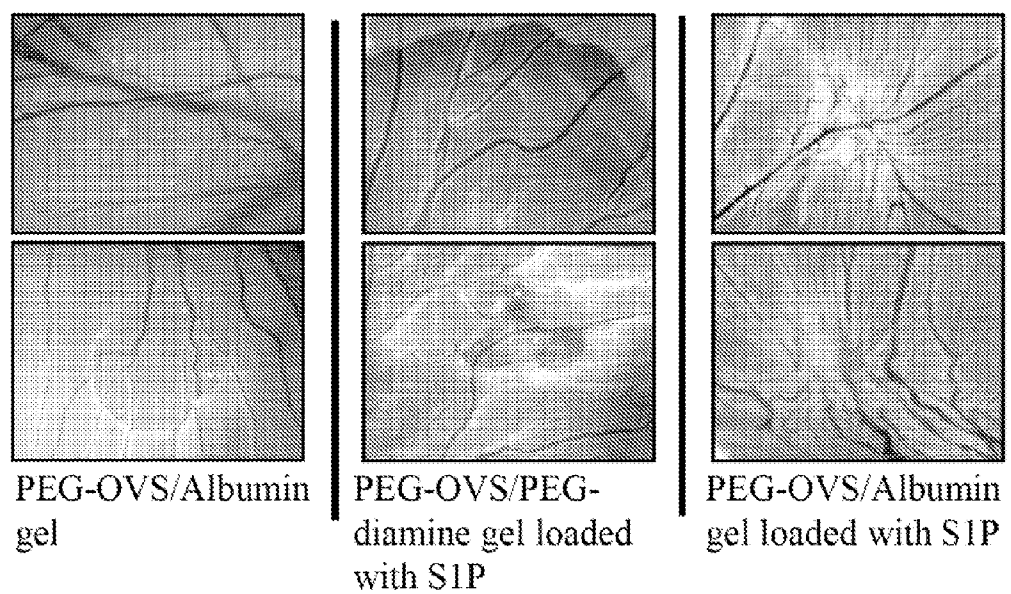

The control solutions, bFGF or S1P, elicited strong angiogenic responses (FIG. 5*a*). PEG-OVS/albumin gels not loaded with S1P did not induce an angiogenic response, while PEG-OVS/PEG-diamine gels postloaded with S1P and washed with PBS for 26 h exhibited at most a modest angiogenic response. However, PEG-OVS/albumin hydrogels postloaded with S1P induced a moderate to strong angiogenic response (FIG. 5*b*). Two independent replicates are shown for each condition.

S1P Release from Preloaded Gels

Figure 6:
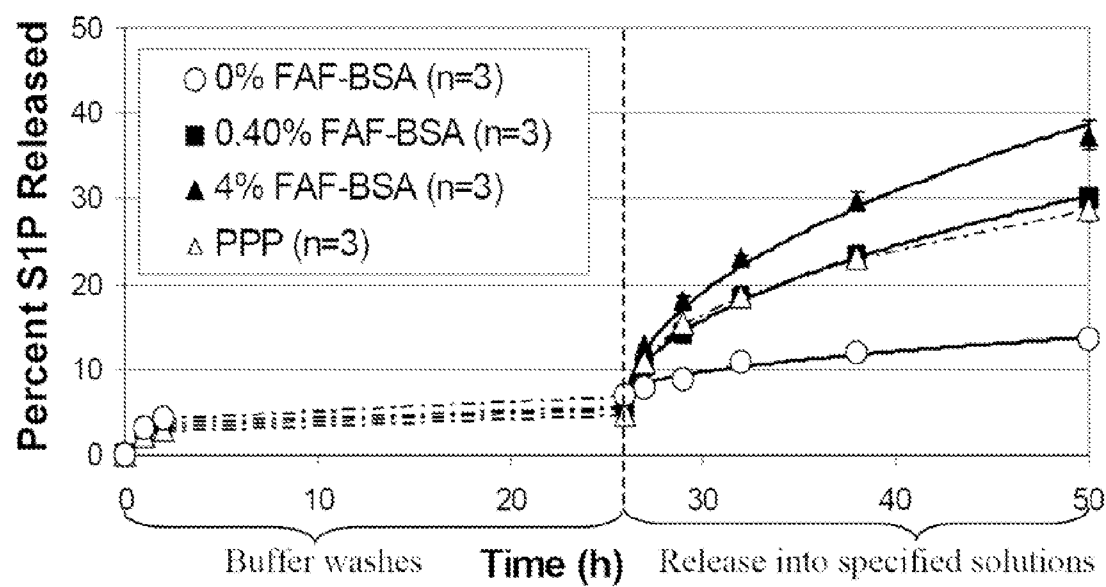
FIG. 6 depicts a schematic of a graph illustrating the percent of [$^{32}$P]S1P released from preloaded PGE-OVA/albumin hydrogels. Approximately 5% of the S1P in the hydrogel was released into the PBS washes over 26 h. The rate of S1P release increased with increasing concentrations of FAF-BSA in the release solution. Dashed lines connect data points, solid lines show least squares fits of the data.

Release of S1P from preloaded PEG-OVS/albumin hydrogels was quantified using [$^{32}$P]S1P. [$^{32}$P]S1P was dissolved in 570 μL PBS containing 95 mg FAF-BSA. Aliquots were mixed with PEG-OVS and incubated for 24 h to form S1P-containing hydrogels (50 μL total volume) on the bottoms of wells in a 24-well plate. The formed gels were washed with PBS over 26 h and then incubated with solutions containing different concentrations of albumin in PBS. S1P release into PBS alone was limited, while the rate of release increased with higher concentrations of albumin in solution over time (FIG. 6). Controlled release was observed; 33.8±1.5% of the S1P remaining in the washed gel was released into 4% FAF-BSA by 24 h and 26.0±0.5% of the S1P released into 0.4% FAF-BSA by 24 h. S1P release into human platelet poor plasma, which contains approximately 4% albumin, displayed release kinetics similar to 0.4% FAF-BSA in PBS. This may be due to competition of S1P released from the hydrogels with lipids already bound to albumin and lipoproteins in plasma.

Sulforhodamine B Release from Preloaded Hydrogels

Figure 7:
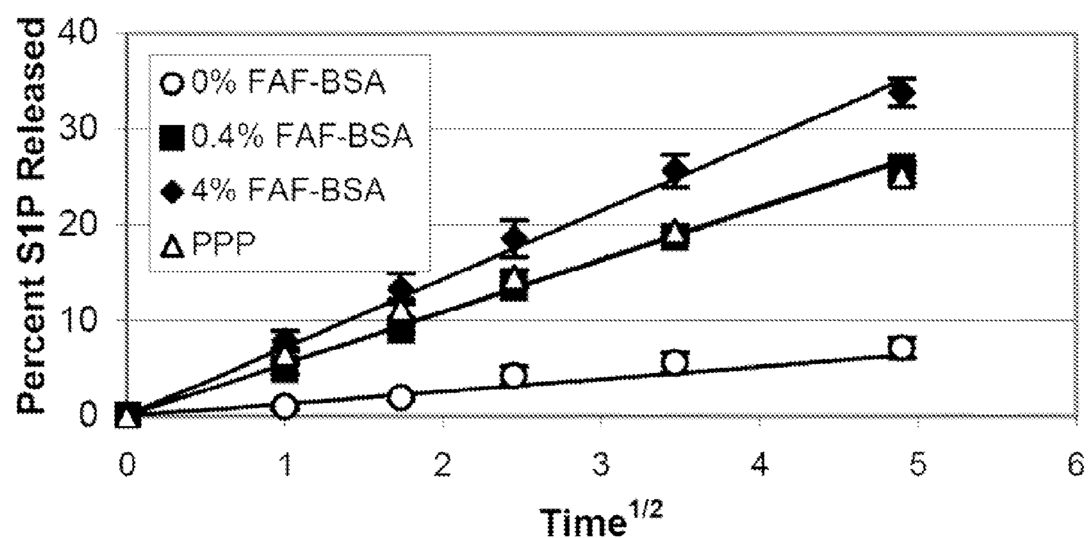
FIG. 7 depicts a schematic of a graph illustrating the release of sulforhodamine B preloaded into the different hydrogels. (A) The S1P release data was plotted as a function of $(time)^{1/2}$. (B) The effect of gel crosslink density on the release of small molecules was minor compared to the effect of specific binding to albumin. Release of sulforhodamine B, a water-soluble dye molecule 50% larger than S1P, was measured from 50 μL PEG-OVS/albumin gels. The dye (500 nmol) was incubated with albumin prior to crosslinking. Release of sulforhodamine B into PBS was nearly complete in 6 h.
Figure 7:
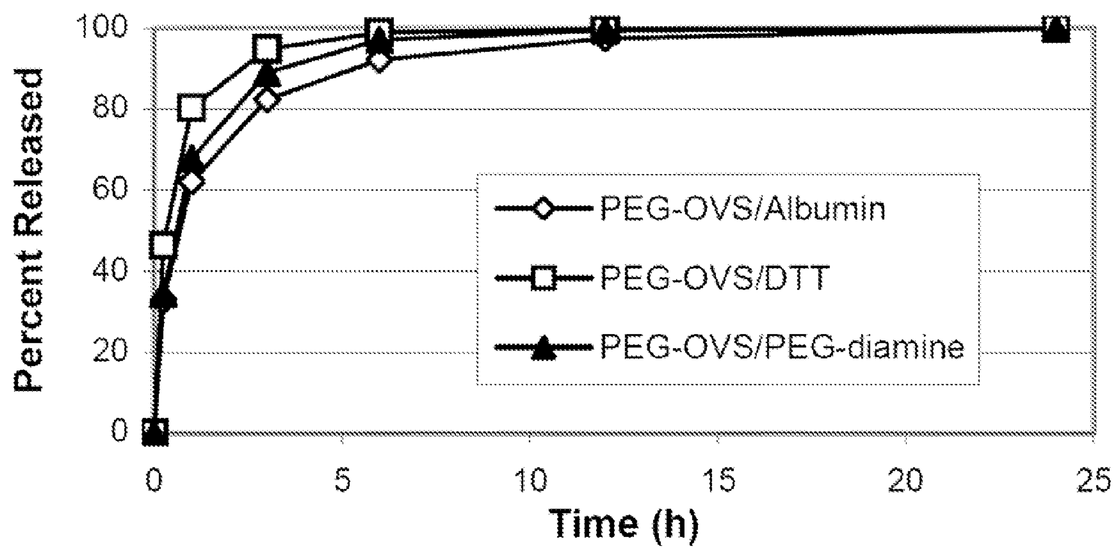

The effect of gel mesh size on the diffusion of small molecules was tested using a water-soluble dye molecule, sulforhodamine B. Sulforhodamine B (500 nmol) was preloaded into gels formed with PEG-OVS crosslinked with albumin, PEG-diamine, or DTT. The gels were incubated win PBS and the release of sulforhodamine B was detected by visible light spectroscopy at 554 nm over time. The molecular weight of sulforhodamine is 580.7, compared to 379.5 for S1P, and the diffusivity of the dye would be expected to be lower than that of S1P. Using the Wilke-Chang correlation, we calculated a diffusion coefficient of $3.42\times10^{-6}$ cm$^2$/sec for sulforhodamine and $4.15\times10^{-6}$ cm$^2$/sec for S1P, both at 37° C. Release of sulforhodamine B from the hydrogels was rapid, nearing completion in 6 h (FIG. 7), indicating that the mesh size of the PEG-OVS/albumin gels does not greatly affect the release of small molecules.

Endothelial Cell Migration

Time-lapse microscopy was used to quantify endothelial cell migration speeds on PEGOVS/albumin hydrogels containing RGD peptide and preloaded with S1P. RGD peptide was added to the PEG hydrogels to promote endothelial cell adhesion and spreading on the materials. PEG-OVS (3.4 mg in 20 μL) was reacted for 30 min with acetyl-GCGYG <u>RGD</u>SPG-NH$_2$ peptide [SEQ ID NO. 5], to attach the peptide to 1/20 of the vinyl sulfone groups (2.78 mM RGD peptide in the final hydrogel). The PEG hydrogels were crosslinked by reacting PEG-OVS with albumin (5.2 mg in 30 μL) premixed with S1P (5 nmol) to give a final concentration of 100 μM S1P within the crosslinked hydrogel. The resulting solution (50 μL) was pipetted into a 24-well plate and incubated at 37° C. for 24 h to allow crosslinking. HUVEC from passage 5-7 were seeded onto the gels at a concentration of 1000 cells/cm$^2$. After allowing the cells to spread for 6 h in complete growth medium, HEPES-buffered low serum medium (MCDB 131 with 0.1% FBS, 1% ABAM, 10 μM HEPES, pH 7.4) containing 0.4% FAF-BSA was added to the cells. The cells were tracked using time-lapse microscopy for 12 h, recording images every two minutes. Individual cell migration speeds were analyzed manually using ImageJ to trace the path of each cell over time. The time increment between analyses was increased to six minutes if cells maintained a straight path in the three consecutive images.

Figure 8:
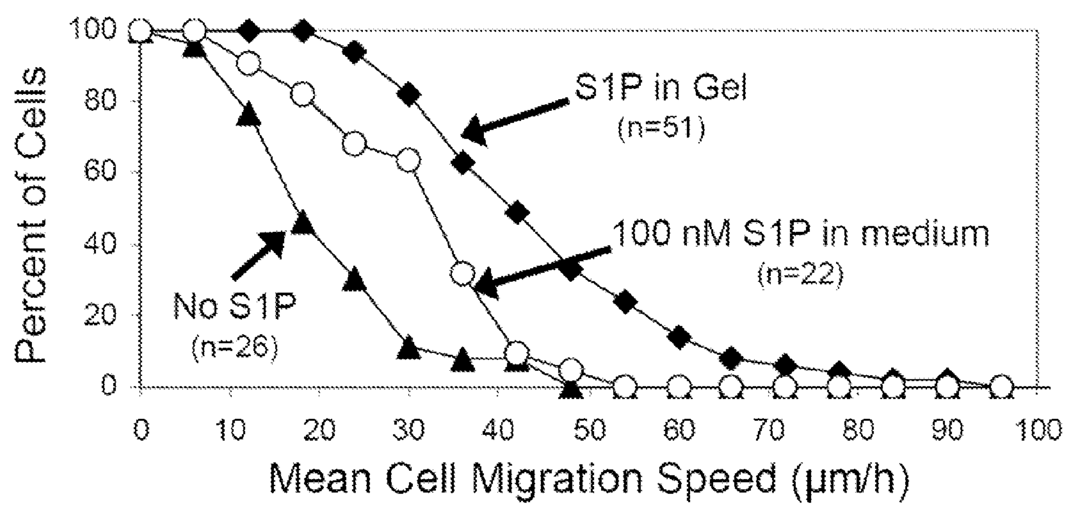
FIG. 8 depicts a schematic of a graph illustrating the mean migration speed of endothelial cells in response to S1P. S1P was provided in the medium or released from a preloaded PEG-OVS/albumin/RGD hydrogel.

Cell migration speeds were measured for HUVEC on 50 μL PEG/albumin/RGD hydrogels formed on the bottoms of wells of a 24-well tissue culture plate. Delivery of S1P from the hydrogels increased the mean migration speeds of HUVEC from 19.2±10.1 μm/h to 43.8±15.7 μm/h (FIG. 8). The addition of culture medium containing 100 nM S1P increased the mean migration speed to only 30.2±11.8 μm/h.

Based on release between 32 h and 44 h in FIG. 6, the S1P concentration in the low serum medium increased from less than 1 nM (low serum medium contained 0.1% FBS, and FBS contains 142 nM S1P28) to at least 303 nM by the end of the migration experiment.

Example 6

Hydrogels Formed with Sphingosine Kinase

Hydrogels were formed with the enzyme sphingosine kinase to produce S1P in the materials from a precursor (sphingosine) naturally present in the blood. Human sphingosine kinase was cloned by RT-PCR from human umbilical vein endothelial cell mRNA. The PCR insert with the correct sequence was transferred from the cloning vector to the expression vector, pGEX-6P-1, using the restriction enzymes EcoRI and XhoI, to create an N-terminal GST-tagged sphingosine kinase [SEQ ID NO. 1]. The plasmid with the correct sequence was transfected into BL21 *E. coli* and the cells were grown to $OD_{600}$ 0.6 in LB medium. Protein expression was induced with 1 mM IPTG. After 3 h, the cells were harvested by centrifugation for 20 min at 6000 g, 4° C. The cells were lysed with lysozyme and sonication. The lysate was centrifuged at 50,000 g for 45 min at 4° C. and the supernatant was filtered. The GST-containing protein was purified using GSTrap FF columns. Activity of the protein (10 μg/mL) was assessed by incubation with 50 μM D-erythro-sphingosine and 1 mM in 0.1% BSA in PBS for 0-30 min, followed by dilution 1:1 with methanol and acidification to pH 1 with HCl. Lipids were extracted into chloroform and analyzed by thin layer chromatography on silica plates with butanol-acetic acid-water 6:2:2, with detection by ninhydrin. There was complete conversion to sphingosine 1-phosphate within 30 min.

Figure 9:
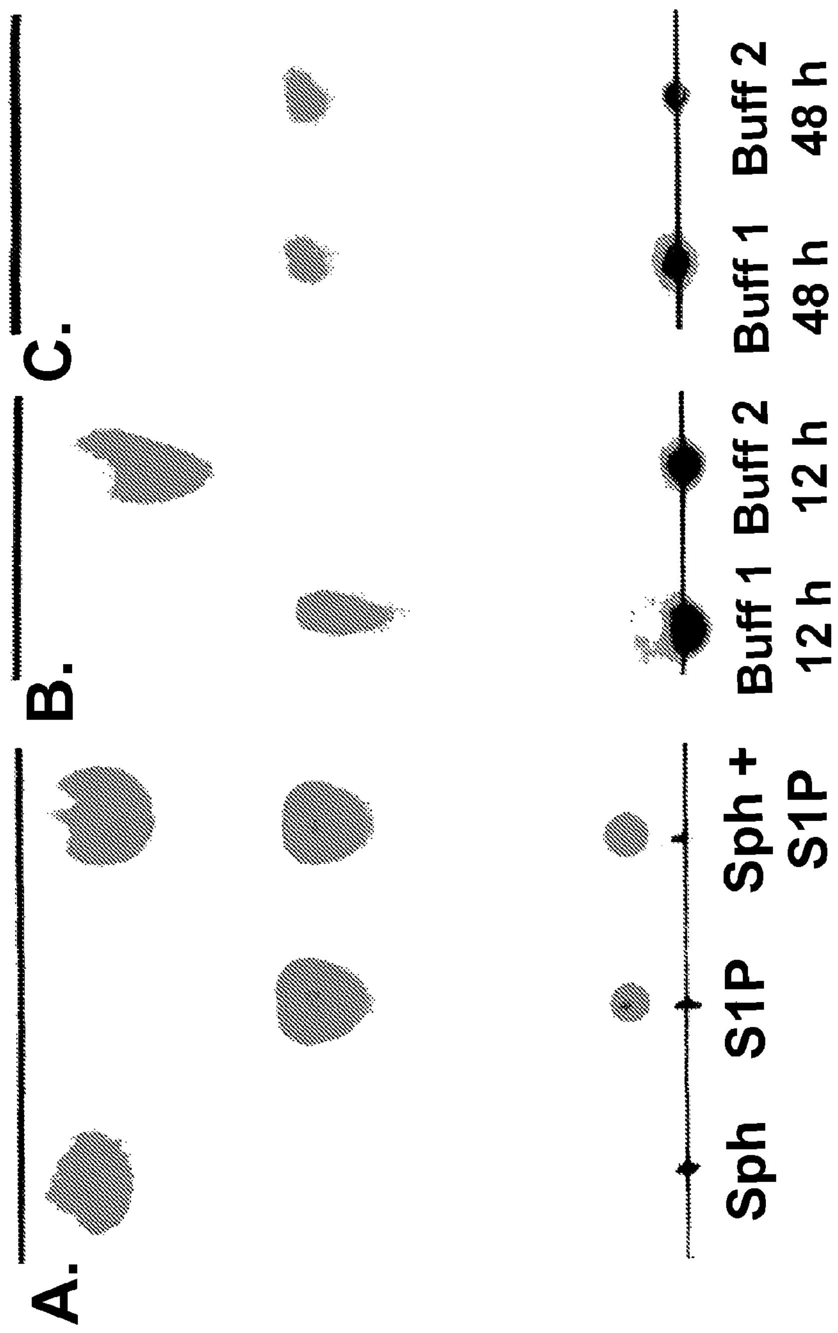
FIG. 9 depicts a series of images illustrating the conversion of sphingosine (Sph) into S1P by PEG-OVS/albumin/sphingosine kinase hydrogels. Panel A shows the migration of Sph and S1P standards on thin layer chromatography plates. Panels B and C show the conversion in the gels after 12 h and 48 hr, respectively.

Sphingosine kinase gels were produced by incubating 4 mg of PEG-OVS with 50 μL of 25 μM purified GST-tagged sphingosine kinase [SEQ ID NO. 1] in Buffer A (20 mM Tris-HCl, pH 7.4, 10% glycerol, 0.05% TritonX-100, 1 mM dithiothreitol) for 1 h. Then, 6 mg of albumin was added to crosslink the PEG at 37° C. for 24 h. Each gel was washed with PBS for 24 h. Reactions contained 500 μM sphingosine and 1 mM ATP in 500 μL in Buffer 1 (100 μL of Buffer A diluted in 400 μL of PBS) or Buffer 2 (PBS with 0.02% BSA). At different times, the supernatants were removed and gels were washed for 24 h with PBS containing 0.4% BSA. Lipids were extracted from these solutions using chloroform/methanol and analyzed by thin layer chromatography on silica plates, as described above. At 12 h, most of the sphingosine was converted to S1P in the presence of Buffer 1, whereas by 48 h the conversion was complete under both conditions (FIG. 9).

Example 7

Endothelial Cell Migration Induced by Local S1P

Figure 10:
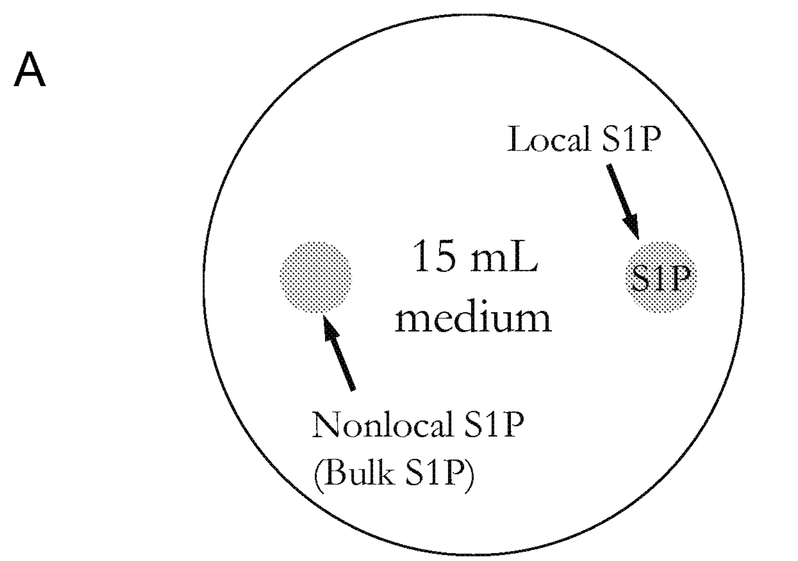
FIG. 10 depicts images that show that the local delivery of S1P increases endothelial cell migration. (a) Two thin PEG-OVS/albumin gels were crosslinked on the bottom of a tissue culture dish on opposite sides. Both gels contained 1.38 mM linear RGD, but only one gel contained S1P. The S1P releasing gel was deemed 'local S1P', while the other gel was deemed 'nonlocal S1P'. Low serum medium (15 mL) with 0.4% FAF-BSA was added to the tissue culture dish. (b) HAEC migration speed on the local and nonlocal S1P gels were compared to that on a gel where no S1P was in the medium. No change in migration speed was seen with nonlocal S1P release, while an increase in migration speed was seen with local S1P release. * $p<0.05$ vs. no S1P and nonlocal S1P. Data are means±standard deviation. Analysis by ANOVA Scheffe post hoc.
Figure 10:
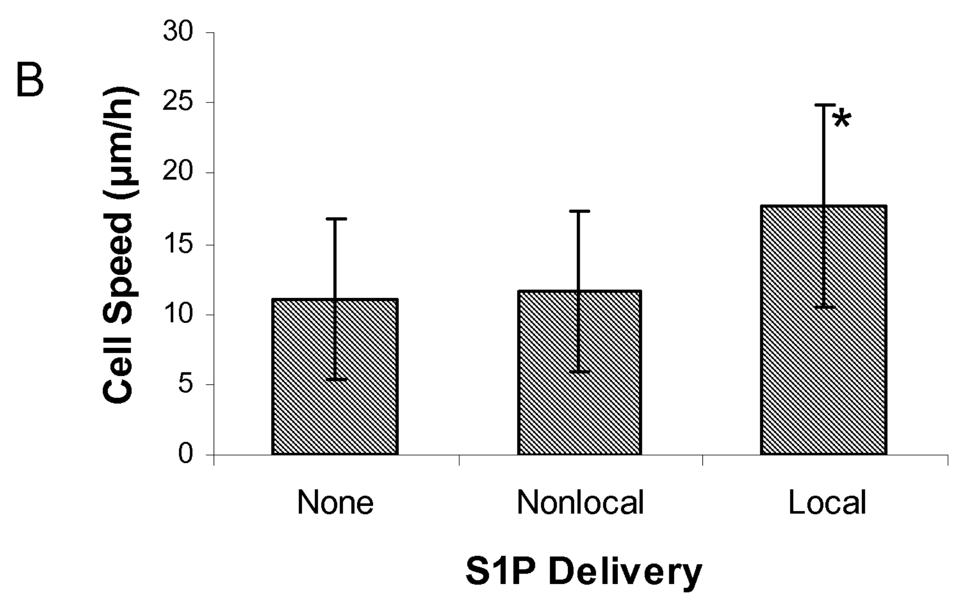

Endothelial cell migration is essential to both vascular wound healing and angiogenesis. The interaction of the cells with the substrate is critical to the motility of the cells. PEG-OVS/albumin gels containing RGD were crosslinked on the bottom of a tissue culture dish on opposite sides, one which was preloaded with S1P (local S1P gel), and one that was not preloaded with S1P (nonlocal S1P gel) (FIG. 10A). The gels were seeded with HAEC and endothelial cell migration was tracked. The gel delivering S1P was expected to produce a local increase in S1P concentration as it was released from the hydrogel. The S1P would then diffuse into the 15 mL of LSM with 0.4% FAF-BSA diluting it so that the gel on the opposite side would see only the bulk concentration of S1P in the medium. Using this method migration induced by local S1P delivery and migration induced by changes in the bulk S1P concentration could be differentiated. As a control, cells were tracked on a RGD PEG-OVS/albumin hydrogel with no S1P in the dish. The cells on the nonlocal S1P gel had no change in endothelial cell migration speed compared to the control without S1P (FIG. 10B). However, the cells on the S1P releasing hydrogel had a significant increase in cell migration speed. These results show that S1P delivery from the PEG-OVS/albumin hydrogels can increase cell migration through a local S1P increase even when the bulk S1P concentration does not have an effect by itself. The S1P concentration in the low serum medium increased to about 30 nM by the end of the experiment.

Example 8

Cell Migration on RGD Containing Hydrogels

RGD concentration should be optimized for maximal endothelial cell migration and adhesion on RGD containing hydrogels. S1P may allow fast cell migration at high RGD concentrations, and thus high adhesion strengths, that otherwise would restrict cell migration. This would allow for rapid wound healing on a substrate that promotes a very stable attachment of the migrating cells and of the final endothelial cell monolayer. Both a linear and a cyclic RGD peptide were tested at various concentrations. It was determined that cell adhesion strength increased with RGD concentration and was stronger on the cyclic RGD peptide. Single cell tracking was used to demonstrate that maximal endothelial cell migration speed was obtained with S1P on the cyclic RGD peptide in the presence of arterial levels of fluid shear stress. With S1P on linear RGD, a greater increase in migration was observed at the highest RGD concentrations, and migration and cell adhesion strength continued to increase with increasing concentrations of cyclid RGD in the gels.

Synthesis of RGD Peptides

The linear RGD (Ac-GCGYGRGDSPG) [SEQ ID NO:5] was prepared as described above. The cyclic RGD (Ac-GCNAC*RGDGWC*G) [SEQ ID NO:6] was synthesized on a 433A Peptide Synthesizer (Applied Biosystems). The protecting groups of the 2nd and 3rd cysteines were p-methoxytrityl (Mmt), while the first cysteine was protected by a trityl (Trt) group. The Mmt protecting groups were selectively removed with 1% TFA while the peptide remained attached to the resin. The peptide was mixed with 94:1:5 DCM/TFA/TIS by bubbling nitrogen through the solution for 5 minutes. The solvent was removed and the selective cleavage was repeated two more times. The resin was removed by filtration with a PTFE membrane in a sintered glass funnel. The peptide was cyclized by on-resin disulphide formation by various methods. Among the methods tried were catalysis with eosin Y, triethanolamine, and green light, dimethyl sulfoxide-mediated oxidation, and air oxidation in 0.1% ammonium bicarbonate solution (Annis, Hargittai and Barany 1997). We achieved the most consistent success using air oxidation in NMP with 0.1 M TEA. For this method, air was bubbled through the NMP/TEA solution, keeping the resin suspended in the solution. After 3 days of reaction, the solvent was removed by filtration. The peptide was cleaved for 2 h under nitrogen in 5 mL cleavage cocktail (95% trifluoroacetic acid, 2.5% triisopropylsilane, 2.5% water) with mixing every 30 minutes. The resin was removed from solution by filtration through glass wool packed in a glass pipette, and the peptide precipitated in 200 mL ice cold ether. The peptide was collected by vacuum filtration through a PTFE membrane and dried under vacuum.

RGD Peptide Purification

Purification of the linear RGD peptide was described above. The cyclic peptide was dissolved in 0.1% TFA in water and purified by HPLC on a C18 column using a gradient of acetonitrile from 5% to 30% over 30 min. The molecular weights of the HPLC fractions were measured by MALDI to identify the correct fraction and determine the purity of the peptide. The pure peptide was collected by lyophilization.

Cell adhesion strengths to the RGD containing hydrogel surfaces were assessed using a centrifugation assay to apply controlled detachment forces. PEG hydrogels (75 μL) of various concentrations of RGD were formed on the bottom of a 48-well non-treated culture plate. Following crosslinking for 24 h, HAEC were seeded onto the gels at 10,000 cells/$cm^2$ in 500 μL EGM. After 6 h to allow the cells to attach and spread, the gels were washed with DPBS. The wells were filled with DPBS to the top of the wells and then covered with adhesive sealing tape. Images were obtained at 4× to quantify the number of cells initially attached to the hydrogel. The sealed plates were inverted in the centrifuge and spun at a specified rotational speed for 5 min to remove the cells from the hydrogels. The wells were washed with DPBS to remove the floating cells, and then images were acquired at the same locations as before the centrifugation. The percent of cells remaining on the hydrogel was quantified. The percent of cells remaining was plotted as a function of detachment force allowing the force required to remove 50% of cells to be interpolated from the data.

Flow Chamber Setup for Tracking Under Shear Stress

Human aortic endothelial cells seeded onto RGD/PEG-OVS/albumin hydrogels at 1000-2000 cells/$cm^2$ were tracked under 20 dynes/$cm^2$ fluid shear stress in HEPES-buffered low serum medium (HEPES-LSM; MCDB 131 with 0.1% FBS, 1% ABAM, 10 μM HEPES, pH 7.4) containing 0.4% FAF-BSA for 12 h.

Calculation of Motility Parameters

Time lapse microscopy images were obtained every 2 min for 12 h of endothelial cell migration on the surface of RGD containing PEG hydrogels. The percent of cells remaining on the gels during the course of the experiment was recorded for each RGD concentration. The projected cell areas of all cells were determined by manually outlining the cells after 3 h under 20 dyne/$cm^2$ shear stress. Single endothelial cells were manually tracked for 12 h to obtain XY-coordinate data for the center of each cell. Coordinate data from every six minutes ($\Delta t$=6 min) for all cells in each experiment were saved as variables for analysis in MATLAB (The MathWorks, Natick, Mass.). At each time point i, $t_i = i\Delta t$, the mean squared displacement was calculated using the overlapping interval method. The speed of each individual was calculated by dividing the root mean-square displacement for a single time interval by the tracking interval (6 min). Each cell's persistence time was determined by fitting the persistent random walk model given by Equation 1:

$$\langle d^2(t)\rangle = 2S^2P[t-P(1-e^{-t/P})] \qquad [1]$$

using the calculated speed by nonlinear least squares regression analysis as previously described (Dunn 1983; Othmer, Dunbar and Alt 1988; Harms et al. 2005). Speed simply represents the total path length of a cell over time. Persistence time represents the time period between changes in the direction of movement of more than 60°. Path length is calculated as the product of speed and persistence time. Cell dispersion is the product of speed squared and persistence time. Cell areas were obtained by manually tracing cells. All data was analyzed by ANOVA Scheffe post hoc.

Endothelial Response to Linear RGD Concentration—Cell Attachment Strength

Figure 11:
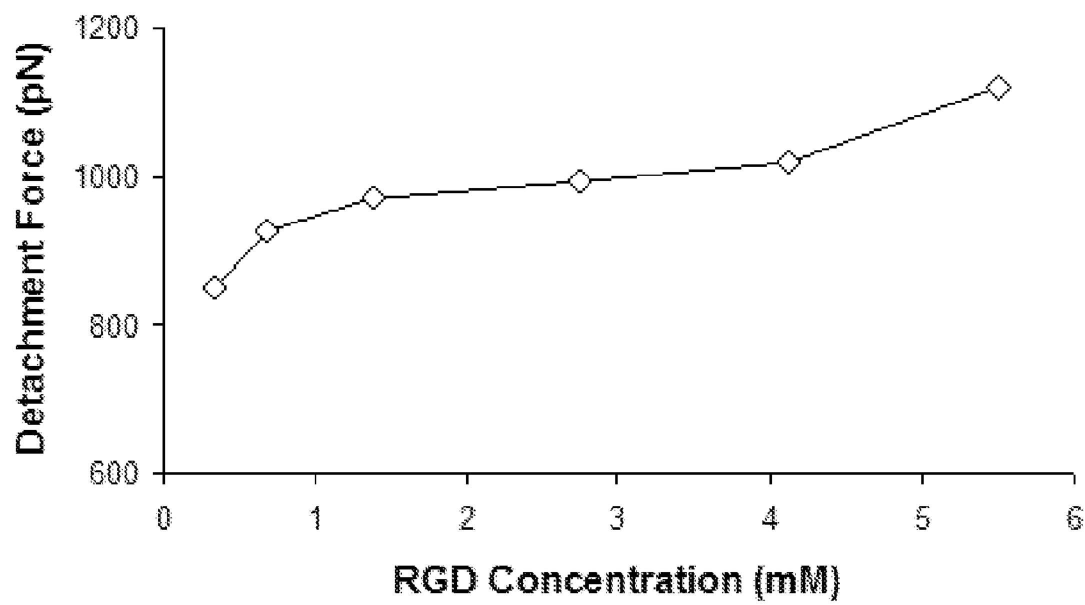
FIG. 11 depicts a graph showing cell attachment strength with a linear RGD polypeptide. The detachment forces for removal of 50% of the cells ($F_{50}$) off of each PEG gel are plotted. The $F_{50}$ increases as RGD concentration increases.

The effects of changing the linear RGD concentration on the initial adhesion strength of endothelial cells to PEG-OVS/albumin hydrogels were examined. HAEC were seeded onto the hydrogels, followed by 6 hours to allow for endothelial cell adhesion and spreading to the surface in EGM. Cell adhesion strengths were assessed by centrifugation of inverted, sealed plates containing hydrogels polymerized in the bottoms of wells. The percent of cells remaining adhered to the hydrogels after centrifugation for 5 min was measured for various forces of detachment on each concentration of linear RGD. The detachment force required to remove 50% of the cells ($F_{50}$) on each RGD concentration was interpolated from the data and plotted versus the concentration of linear RGD (FIG. 11). The $F_{50}$ increased from 850-1120 pN as the concentration of linear RGD was increased.

Cell Tracking Under Flow

Figure 12:
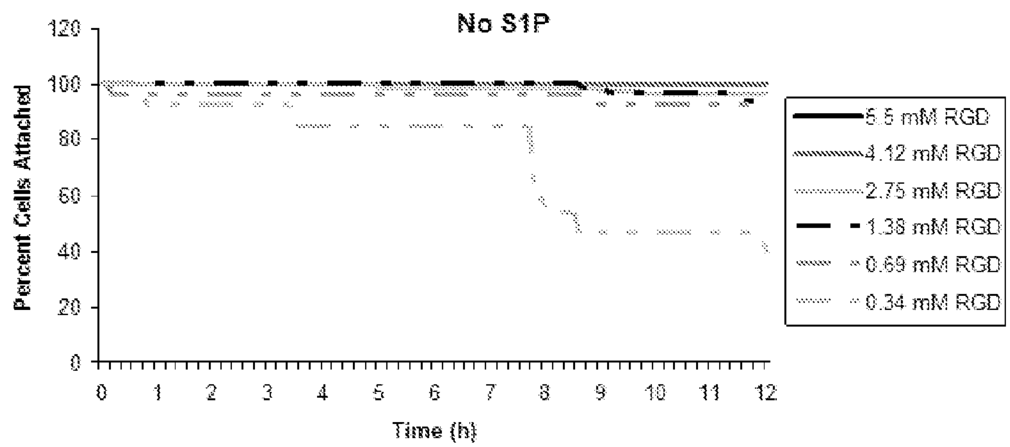
FIG. 12 depicts graphs illustrating the cell adherence to linear RGD PEG under shear stress. The percent of cells remaining on the gels during the experiment is shown. A significant loss of cells was only present for the lowest (0.34 mM) RGD concentration. (A) no S1P. (B) 100 nm S1P.
Figure 12:
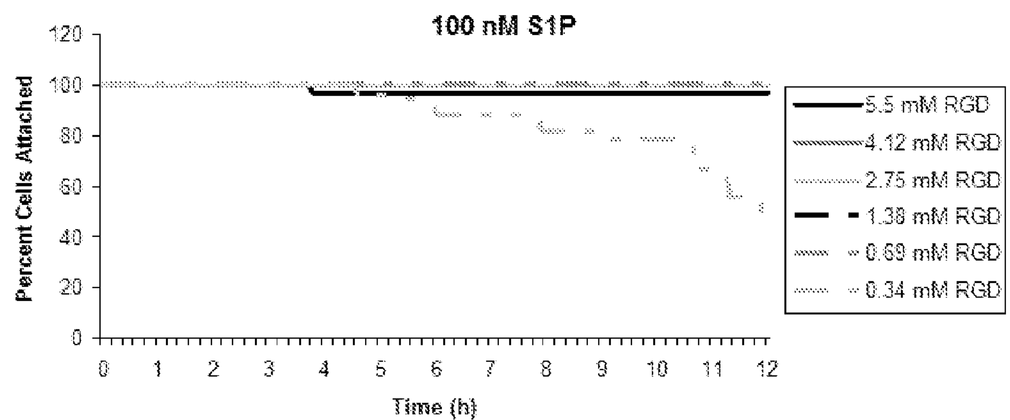
Figure 13A:
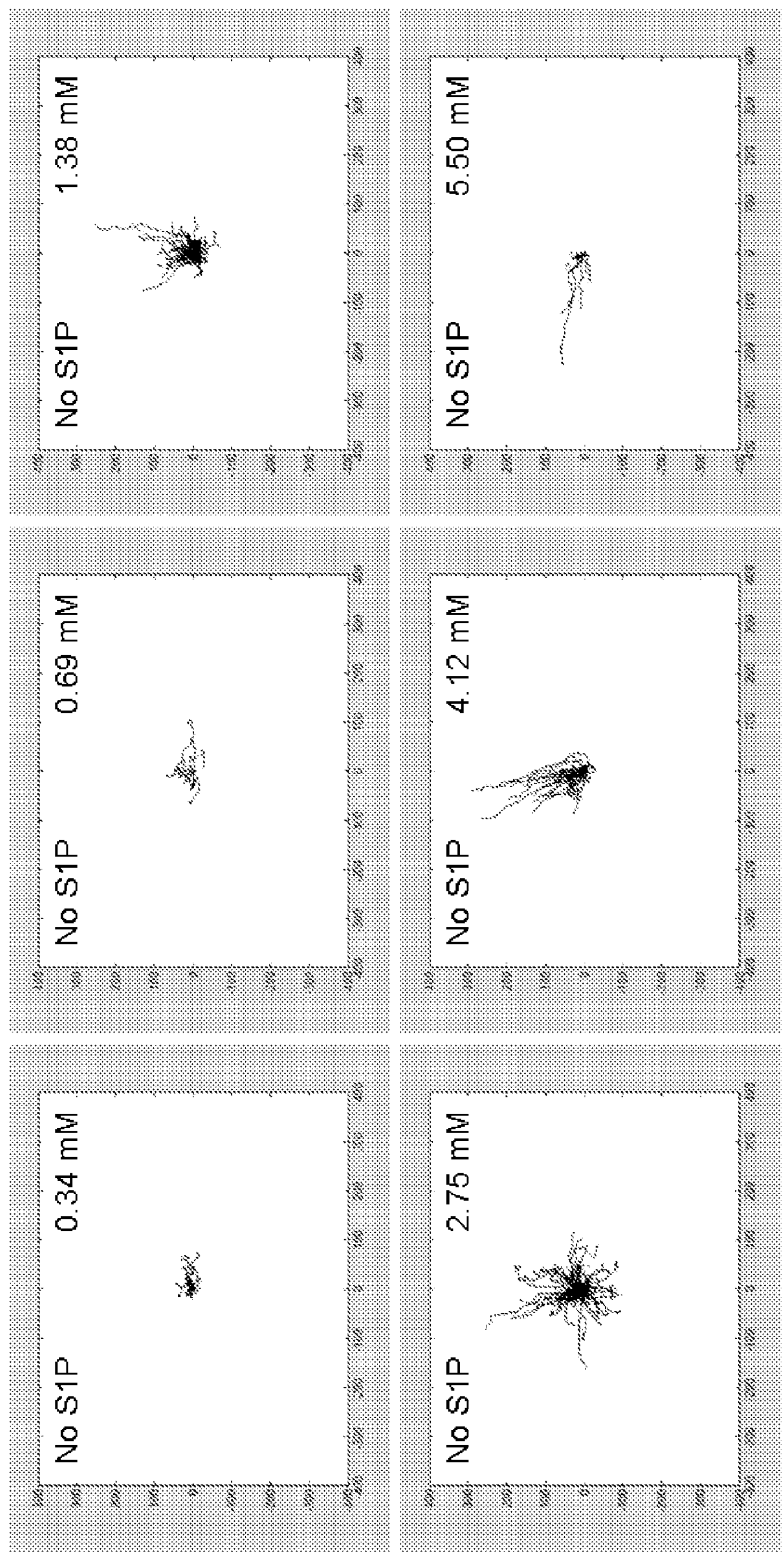
FIG. 13 depicts a series of wind-rose plots of endothelial cells on linear RGD. These plots show the paths of all cells on the PEG hydrogels with the initial location of each cell set to the origin. Cells were tracked for 12 h. The migration of the endothelial cells is affected by S1P and the linear RGD concentration. (A) no S1P. (B) 100 nm S1P.
Figure 13B:
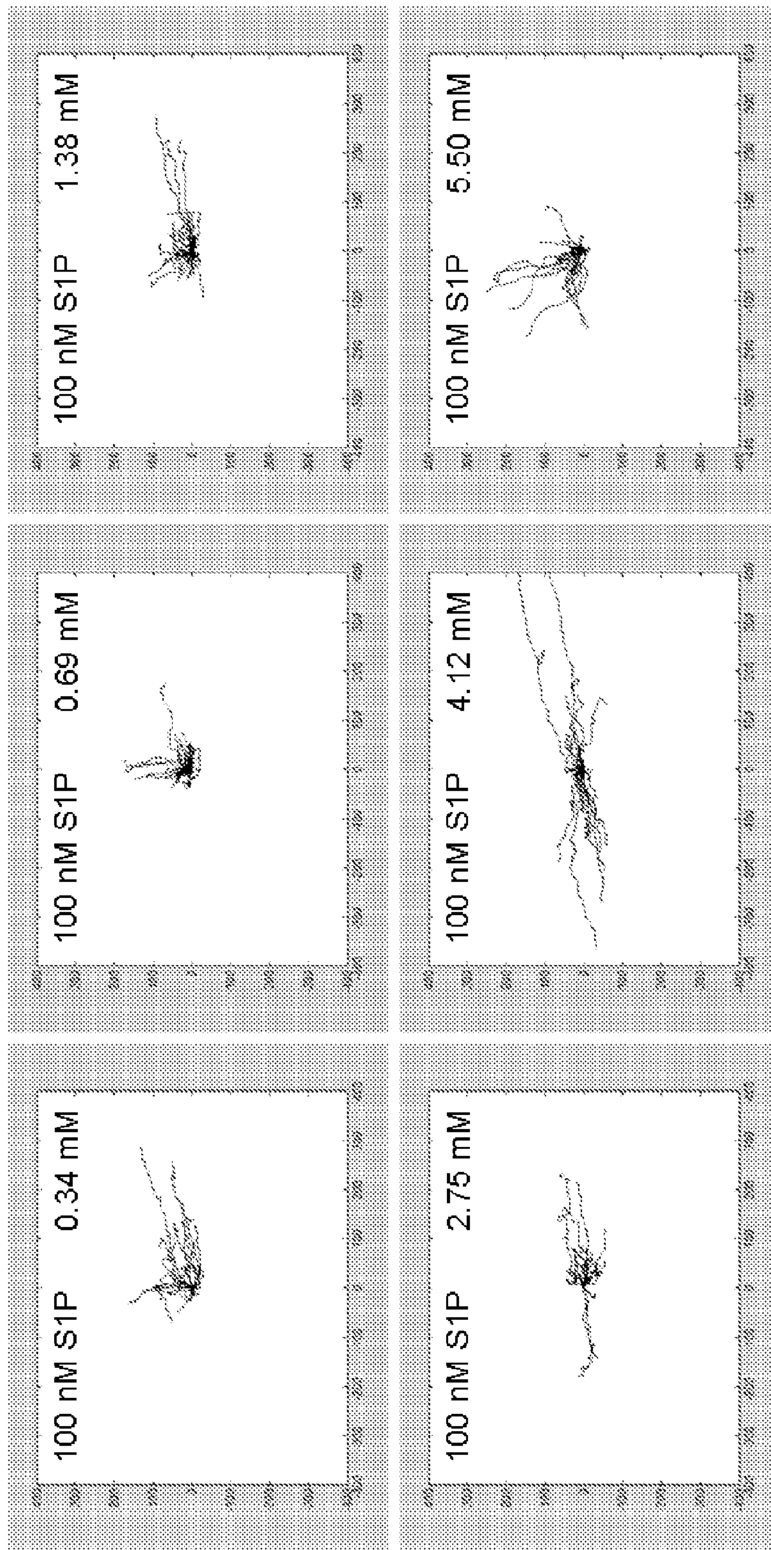

Individual endothelial cell migration was tracked under flow for 12 h in low serum medium. During the course of the experiment, some cells were removed from the hydrogel due to the fluid shear stress (20 dyne/$cm^2$). The percentage of cells remaining attached was calculated for all linear RGD concentrations at all time points (FIG. 12). Significant loss of cells from the hydrogel surface was only seen on the lowest linear RGD concentrations. The paths of all of the cells on linear RGD containing hydrogels are shown as Wind-rose plots where the starting point of each cell is transposed to the origin (FIGS. 13A & B).

Cell Migration Speed

Human aortic endothelial cell migration was tracked by time-lapse microscopy on PEG-OVS/albumin hydrogels containing various concentrations of linear RGD peptide under 20 dynes/$cm^2$ of fluid shear stress in a gravity driven flow chamber. Without S1P delivery, the migration speed of cells on the hydrogels had a biphasic dependency on the linear RGD concentration, with a statistically significant maximum cell speed at 4.12 mM linear RGD. This biphasic dependence was expected from past research by DiMilla et al (DiMilla et al. 1993). When 100 nM S1P was added to the medium, a significant increase in cell speed was seen with increasing RGD concentration, but a drop in migration speed was no longer observed at high linear RGD concentrations, up to 5.5 mM linear RGD in the gel (FIG. 13*a*). At the highest linear RGD concentrations, endothelial cell migration speed was more than doubled by the addition of 100 nM S1P. At the lowest linear RGD concentrations, higher speeds were also found with 100 nM S1P, likely due to weaker adhesion of the cells to the hydrogel, resulting in continuous migration in the direction of the flow.

Cell Persistence Time, Path Length, and Dispersion

Figure 14:
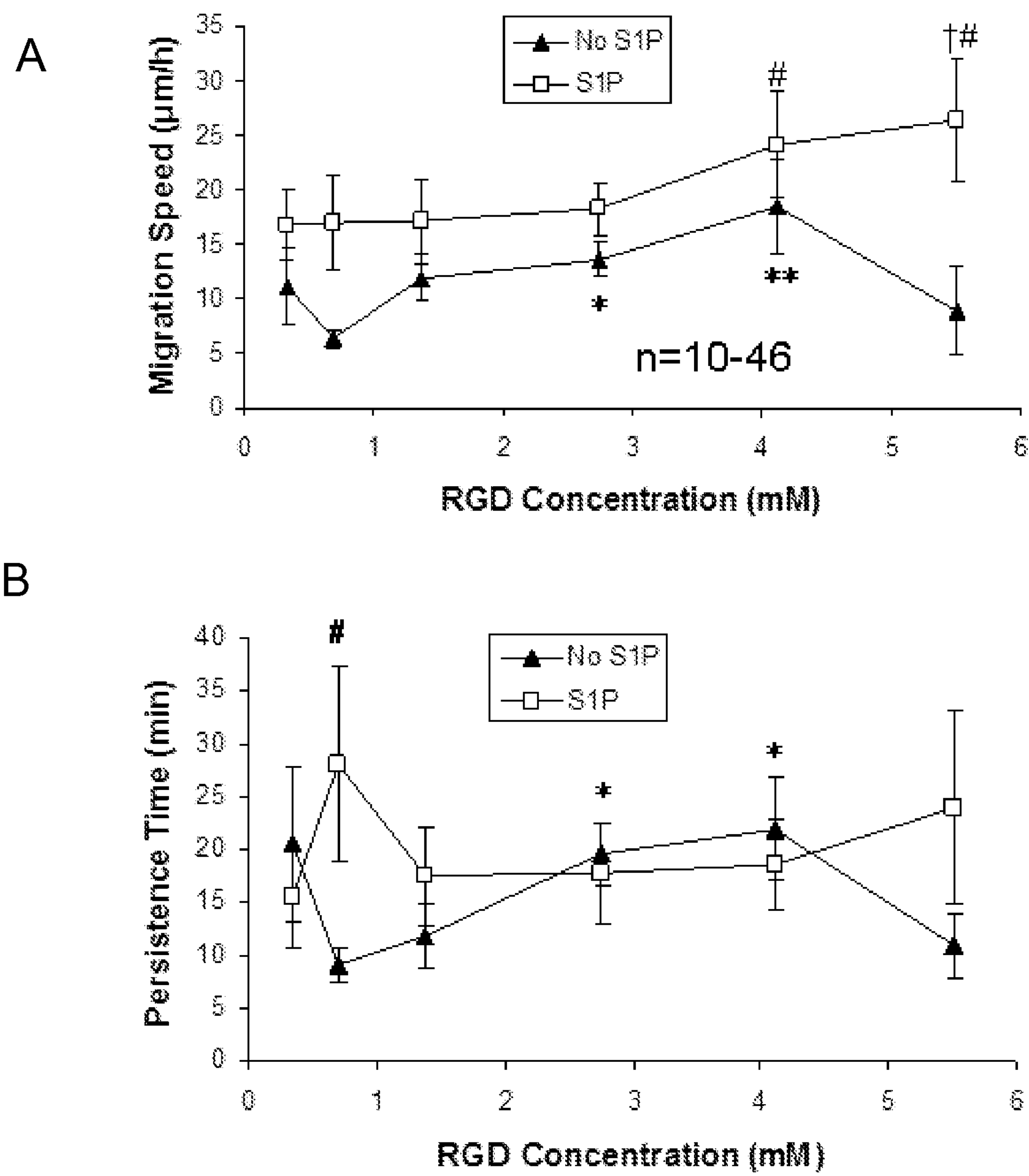
FIG. 14 depicts graphs illustrating cell speed and persistence time on linear RGD. (a) Individual cell speeds presented were found by dividing the path length during a time interval by the time interval. While S1P increases cell speed on all cyclic RGD concentrations, a maximum cell speed was found for 0.69 mM. * $p<0.05$ vs. 0.69 mM RGD without S1P. ** $p<0.05$ vs. 0.69, 1.38, and 5.5 mM RGD without S1P. † $p<0.05$ vs. 0.69 and 1.38 mM RGD with S1P. # $p<0.05$ vs. 0.69, 1.38 mM, 2.75, and 5.5 mM RGD without S1P. (b) Persistence time is not clearly affected on linear RGD by the addition of S1P. * $p<0.05$ vs. 0.69 and 1.38 mM RGD without S1P. # $p<0.05$ vs. 0.69 mM RGD without S1P. Data are means±95% confidence interval based on SEM. Analysis by ANOVA Scheffe post hoc.

The persistence time, representing how frequently a cell makes a major change in direction, was determined for each cell by fitting the calculated speed to the persistent random walk equation. The persistence time of the cells also seemed to have a biphasic relationship with linear RGD concentration in the absence of S1P (FIG. 14*b*). With 100 nM S1P, the biphasic relationship of persistence time was removed. RGD concentration did not significantly change persistence time in the presence of S1P. Persistence time showed some higher values at low RGD concentrations, possibly caused by migration with the flow.

Figure 15:
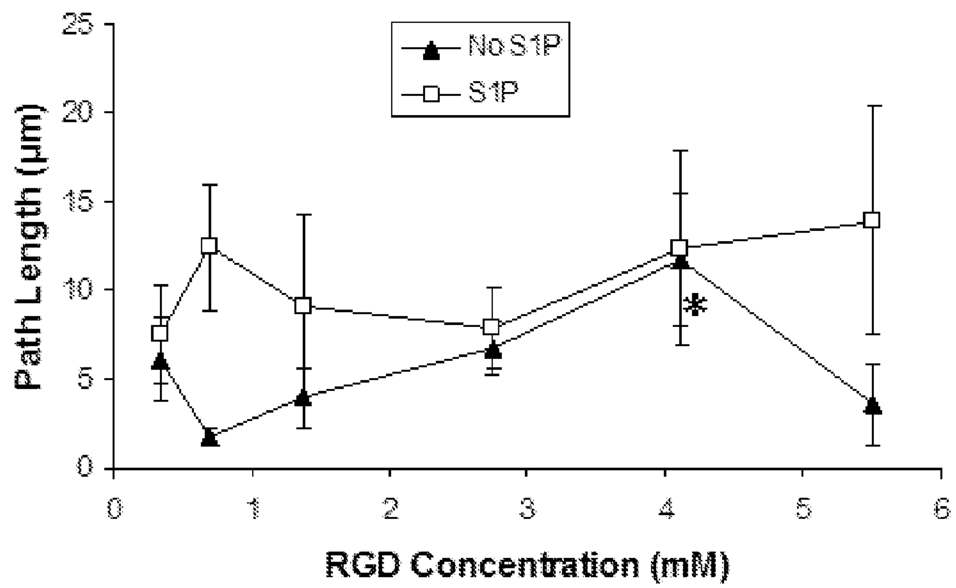
FIG. 15 depicts graphs of path length and dispersion on linear RGD. Path length (speed*persistence) and cell dispersion ($speed^2$*persistence) were calculated for endothelial cells on each PEG hydrogel. (a) Path length has a maximum at 4.12 mM linear RGD without S1P. S1P does not cause a significant increase in path length. * $p<0.05$ vs. 0.69, 1.38, 2.75, and 5.5 mM RGD without S1P. (b) Dispersion has a maximum at 4.12 mM linear RGD without S1P. S1P does not cause a significant increase in dispersion. * $p<0.05$ vs. 0.69, 1.38, 2.75, and 5.5 mM RGD without S1P. Data are means±95% confidence interval based on SEM. Analysis by ANOVA Scheffe post hoc.
Figure 15:
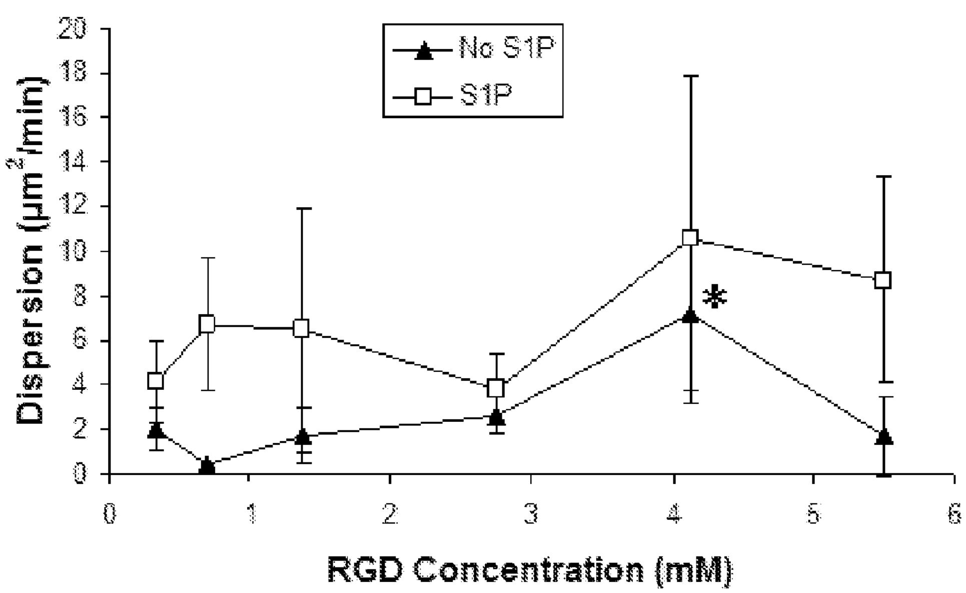

Combined, cell speeds and persistence times determine the motility characteristics of the cells. The distance cells move between direction changes or path length (speed*persistence), and the distribution of the cells, or cell dispersion (speed$^2$*persistence) both had a biphasic relationship with linear RGD concentration (FIG. 15). Increases in path length and dispersion caused by S1P addition were not significant.

Spread Cell Area

Figure 16:
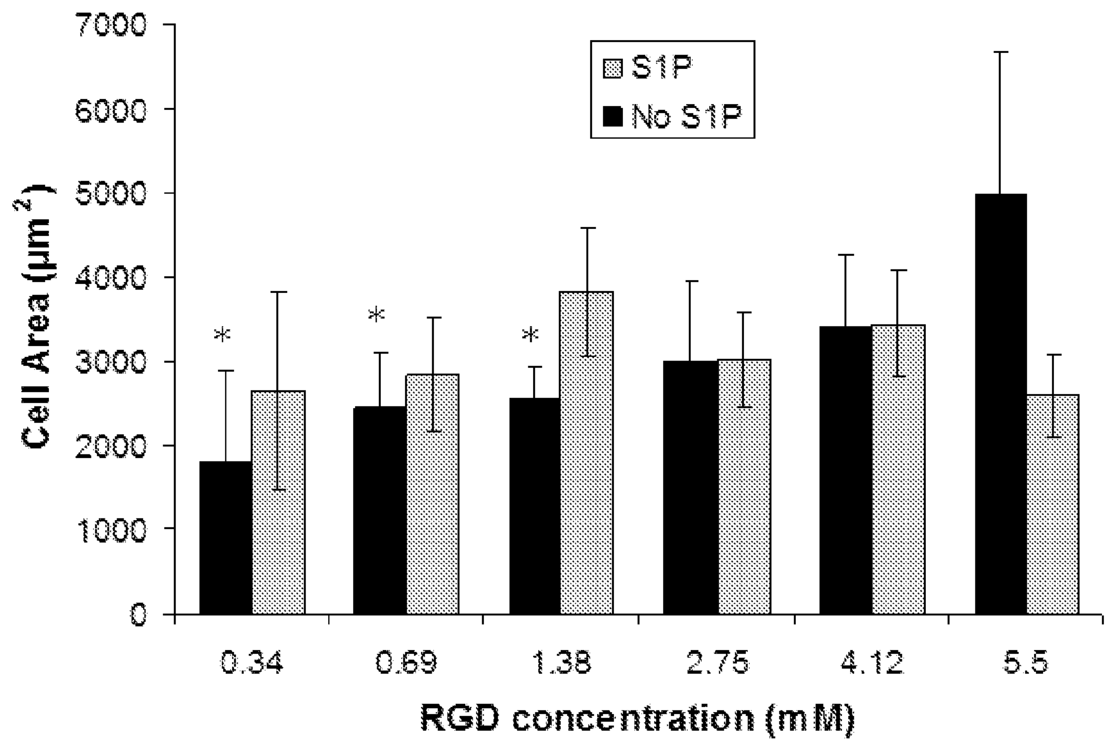
FIG. 16 depicts a graph showing the cell area on various linear RGD concentrations. Cell area was determined by tracing cells on all RGD concentrations. * $p<0.05$ vs. no S1P, 5.5 mM RGD. Data are means±95% confidence interval based on SEM. Analysis by ANOVA Scheffe post hoc.

The projected cell area of each spread cell was measured after 3 h under 20 dyne/cm2 of shear stress. As seen in FIG. 16, without S1P the mean cell area increased as linear RGD concentration increased. With addition of 100 nM S1P, the cell area was not significantly changed by RGD concentration. For a clearer view of how the cell area distribution was affected, we split the cell areas into quartiles. Cell area quartiles were determined using cells on all linear RGD concentrations without S1P to achieve the widest range of cell areas. The fraction of cells in the quartiles was determined for each linear RGD concentration with and without S1P. This allowed us to observe the shift in cell areas caused by S1P at the low and high RGD concentrations. On the four lowest RGD concentrations, an increase in the fraction of cells in the largest area quartiles was seen with S1P, while on the highest RGD concentration, the fraction of cells in the smallest quartile was increased by the addition of S1P.

Cell Area Versus Speed

Figure 17:
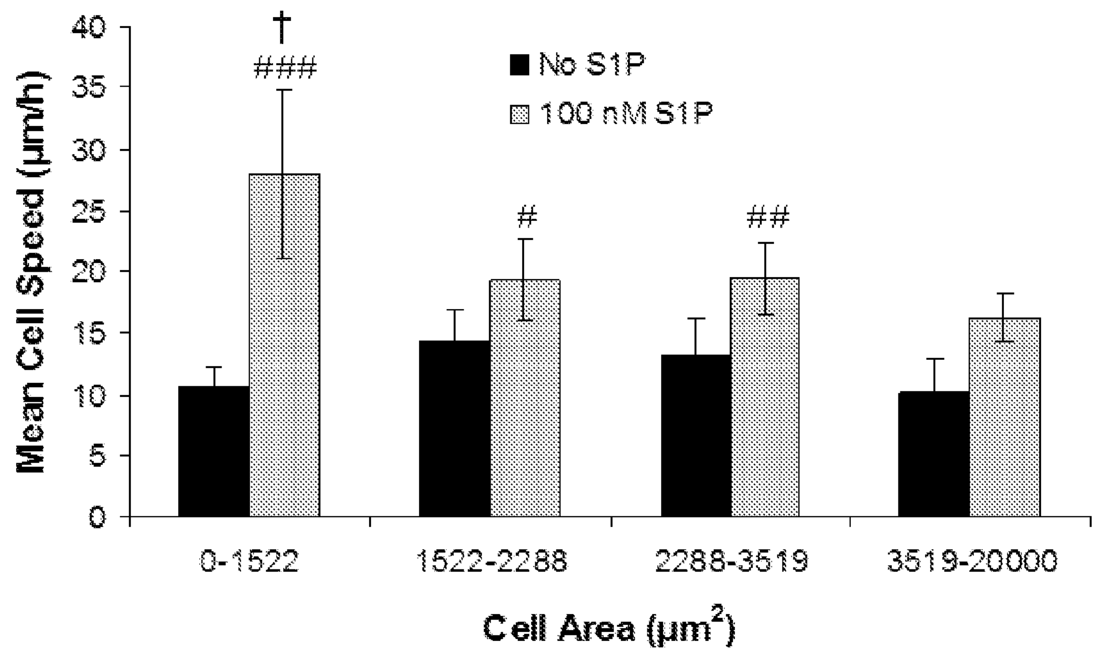
FIG. 17 depicts graphs showing cell speed as a function of cell area on linear RGD. Mean cell speed by cell area quartiles of all linear RGD concentrations $p<0.05$ vs. with 100 nM S1P or no S1P. † $p<0.05$ vs. all cell area quartiles without S1P. ### $p<0.05$ vs. all other cell area quartiles with S1P. # $p<0.05$ vs. 3519-20000 $\mu m^2$ without S1P. ## $p<0.05$ vs. 0-1522 and 3519-20000 $\mu m^2$ without S1P. Data are means±95% confidence interval based on SEM. Analysis by ANOVA Scheffe post hoc.

The relationship between cell speed and cell area on the varying linear RGD concentrations with or without S1P were examined. The cells were also split into the cell area quartiles described above. In the absence of S1P, cell area increases with linear RGD concentration and the cell speeds was not significantly different for cells of different cell area (FIG. 17*b*). When the cells are supplied 100 nM S1P, cell areas are not a monotonic function of linear RGD concentration. However, cell speed appears to increase with linear RGD concentration. The smallest cells had a significantly greater speed in the presence of 100 nM S1P, but not in the absence of S1P. The cell speed was also significantly increased by S1P addition for the smallest cells.

Endothelial Response to Cyclic RGD Concentration

A cyclic RGD peptide (Ac-GCNAC*RGDWGC*G)[SEQ ID NO:6], which has a higher affinity for endothelial cells, and a specificity for the $\alpha5\beta1$ integrin (Koivunen, Wang and Ruoslahti 1995) was also assessed for a range of concentrations in the PEG-OVS/albumin hydrogels.

Cell Attachment Strength

Figure 18:
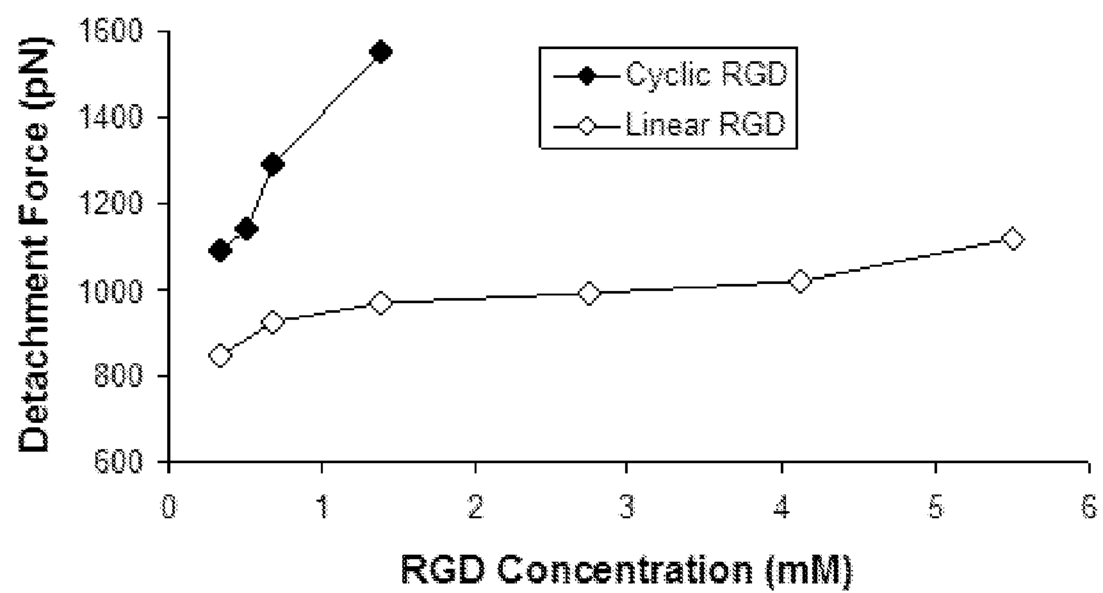
FIG. 18 depicts a graph showing cell attachment strength. The detachment forces for removal of 50% of the cells ($F_{50}$) off of each PEG gel are plotted. The $F_{50}$ increases as cyclic RGD concentration increases. The attachment strength to cyclic RGD is greater than to linear RGD at similar concentrations.

The initial adhesion strength of endothelial cells to the PEG hydrogels containing cyclic RGD peptide was measured after 6 hours to allow for endothelial cell adhesion. The centrifugation assay described for the linear RGD was used to determine the percent of cells remaining adhered to the hydrogels for various forces of detachment on each concentration of cyclic RGD. The $F_{50}$ for each RGD concentration was interpolated from the data giving a range of concentration of cyclic RGD. The $F_{50}$ ranged from 1090 to 1550 pN as the concentration of cyclic RGD was increased (FIG. 18).

Cell Tracking Under Flow

Figure 19:
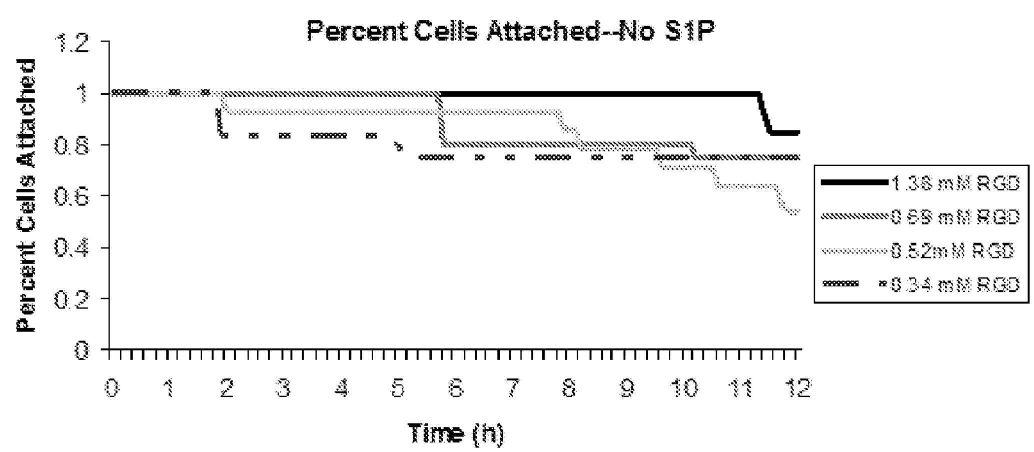
FIG. 19 depicts graphs showing cell adherence to cyclic RGD PEG under shear stress. The percent of cells still adhered to the PEG hydrogels containing cyclic RGD through the course of the 12 h tracking experiment is displayed. (A) no S1P. (B) 100 nm S1P.
Figure 19:
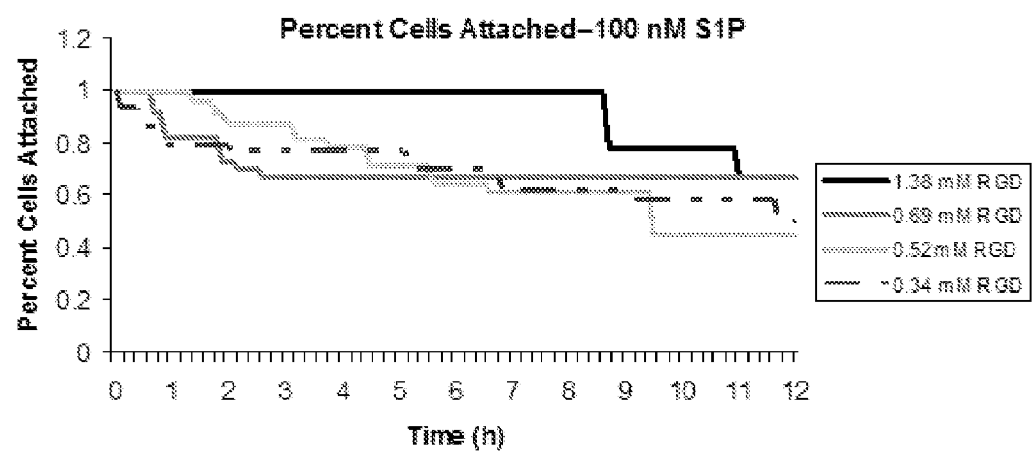
Figure 20A:
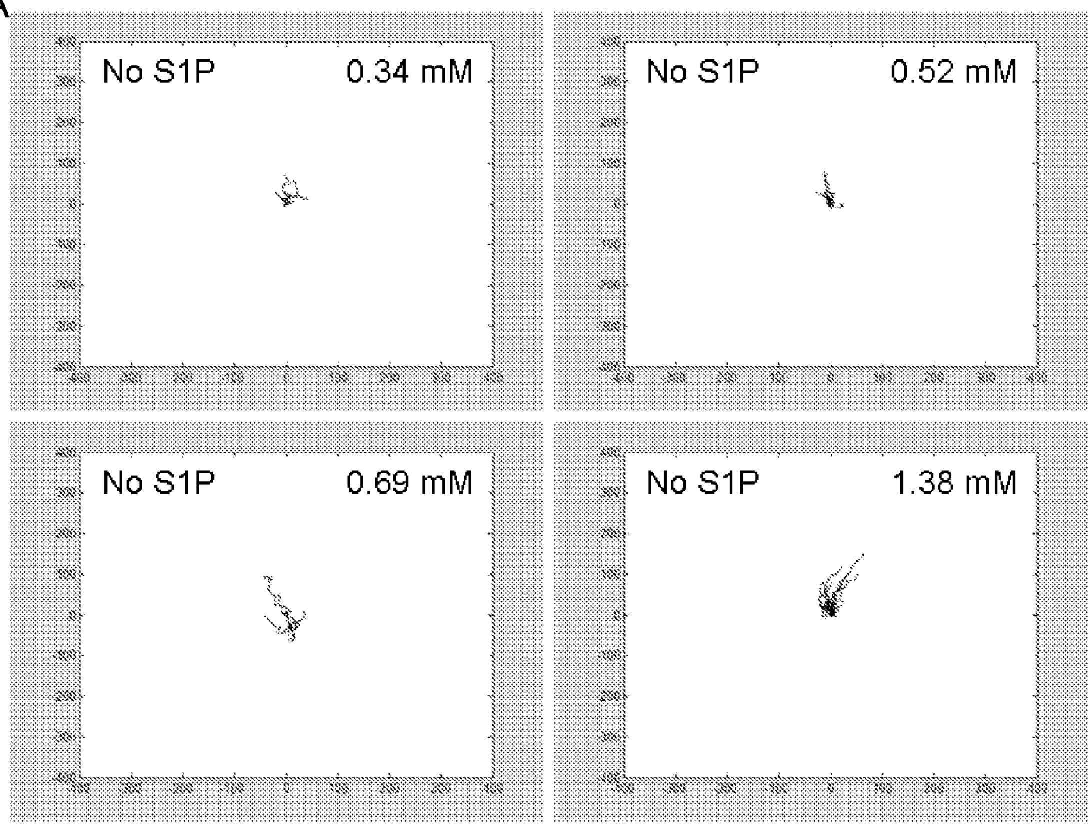
FIG. 20 depicts a series of wind-rose plots of endothelial cell migration on cyclic RGD. These plots show the paths of all cells on the PEG hydrogels with the initial location of each cell set to the origin. The migration of the endothelial cells is affected by S1P and the cyclic RGD concentration. (A) no S1P. (B) 100 nm S1P.
Figure 20B:
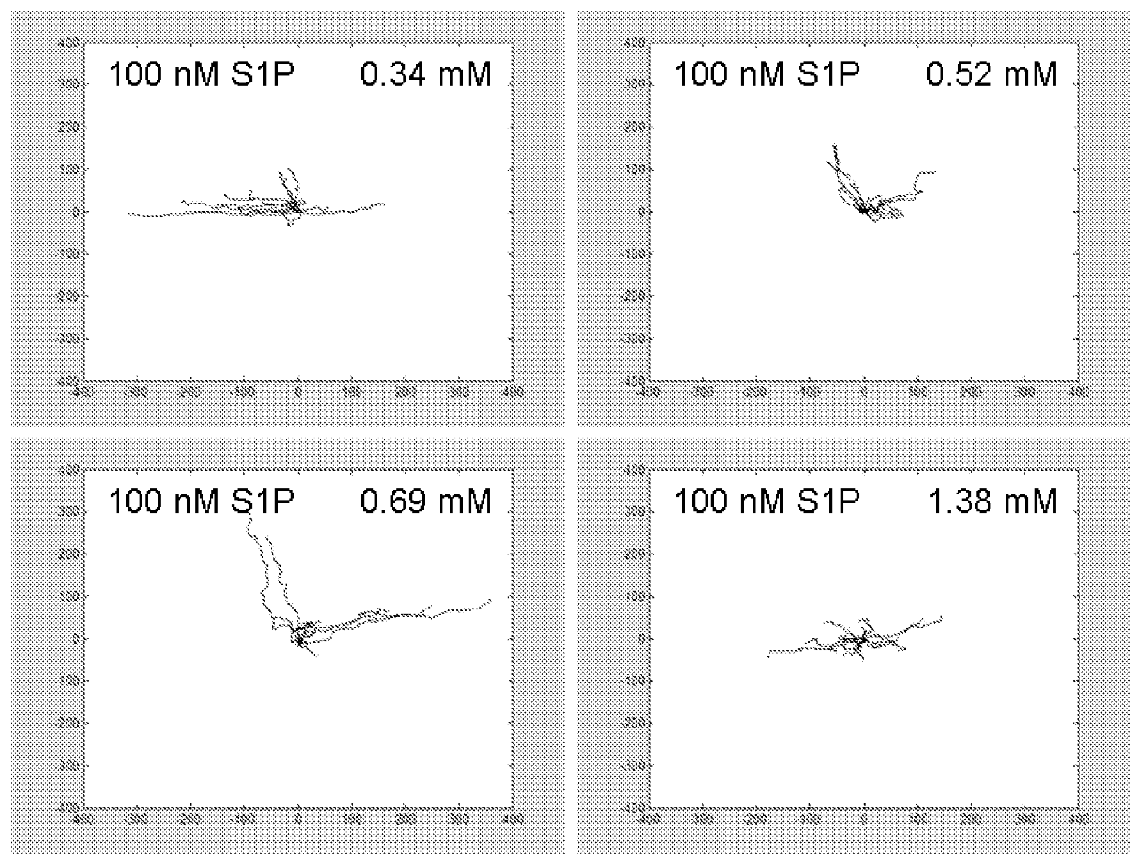

Individual endothelial cell migration was tracked under flow for 12 h. During the course of the experiment, some cells were removed from the hydrogel due to the 20 dyne/cm$^2$ fluid shear stress. The percentage of cells remaining attached was calculated for all the linear RGD concentrations at all time points. Surprisingly a significant loss of cells from the hydrogel surface was observed on all cyclic RGD concentrations (FIG. 19). Even on the highest cyclic RGD concentration a loss of about 20% of the cells was seen over 12 h, while less than 5% of the cells were lost at the same concentration of linear RGD. The paths of all of the cells on cyclic RGD containing hydrogels are shown as Wind-rose plots where the starting point of each cell is transposed to the origin (FIGS. 20A & B).

Cell Migration Speed

Figure 21:
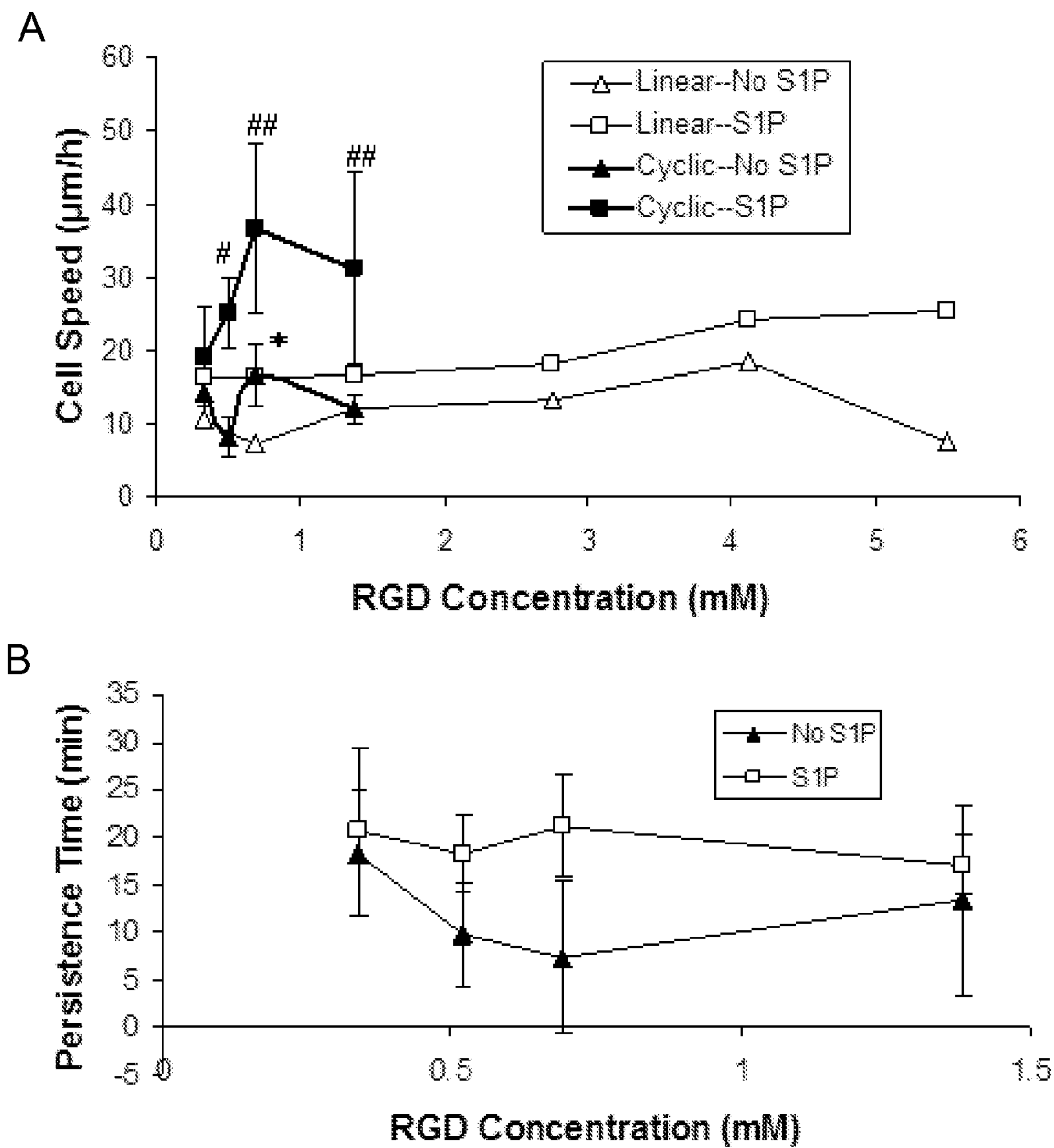
FIG. 21 depicts graphs of cell speed and persistence time on cyclic RGD. (a) Individual cell speeds presented were found by dividing the displacement at the shortest time interval by the time interval (6 min). Migration speed on cyclic RGD is greater than on linear RGD. While S1P increases cell speed on all cyclic RGD concentrations, a maximum cell speed was found for 0.69 mM. ## $p<0.05$ vs. no S1P, 0.52 and 1.38 mM RGD. # $p<0.05$ vs. no S1P, 0.52 mM RGD. * $p<0.05$ vs. no S1P, 0.52 mM RGD. (b) Persistence time was not significantly increased on cyclic RGD by the addition of S1P. Data are means±95% confidence interval based on SEM. Analysis by ANOVA Scheffe post hoc.

HAEC migration was tracked on the PEG-OVS/albumin hydrogels containing cyclic RGD peptide under 20 dyne/cm$^2$ of fluid shear stress. Without S1P delivery, the migration speed on the hydrogels did not have a clear statistically significant dependence on the cyclic RGD concentration (FIG. 21*a*). The high migration speed at the lowest cyclic RGD concentration may have been due to weak adhesion on the hydrogel resulting in migration in the direction of the flow. The addition of 100 nM S1P caused a significant increase in endothelial cell migration speed, particularly at the higher cyclic RGD concentrations. Migration speed with S1P peaked at 0.69 mM cyclic RGD. At this cyclic RGD concentration, the cell migration speed was more than twice the speed of cells without RGD, and 44% greater than the highest migration speed seen on the linear RGD with 100 nM S1P.

Cell Persistence Time, Path Length, and Dispersion

Figure 22:
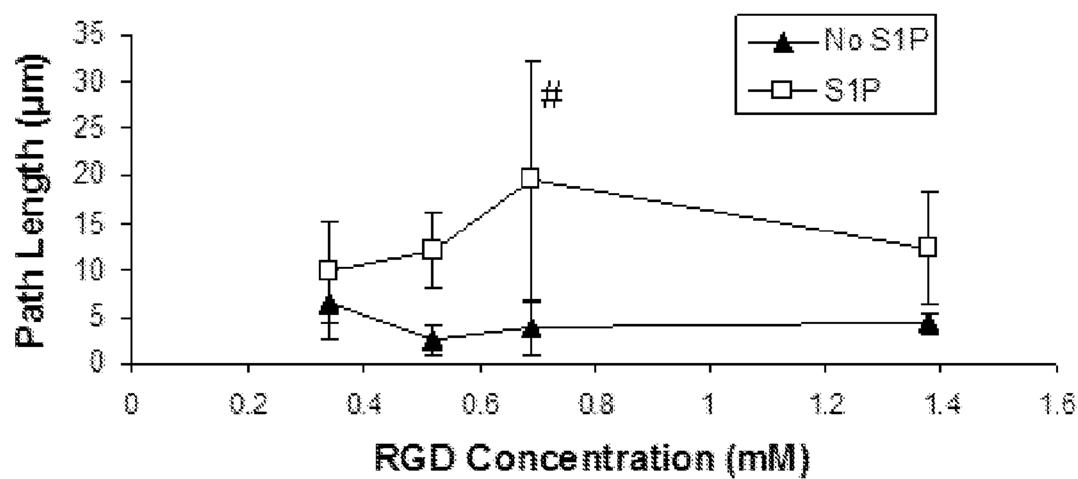
FIG. 22 depicts graphs showing path length and dispersion on cyclic RGD. (a) S1P caused a increase in path length. # $p<0.05$ vs. no S1P, 0.52 and 1.38 mM RGD. (b) S1P caused a increase in dispersion. # $p<0.05$ vs. no S1P, 0.52 and 1.38 mM RGD. Data are means±95% confidence interval based on SEM. Analysis by ANOVA Scheffe post hoc.
Figure 22:
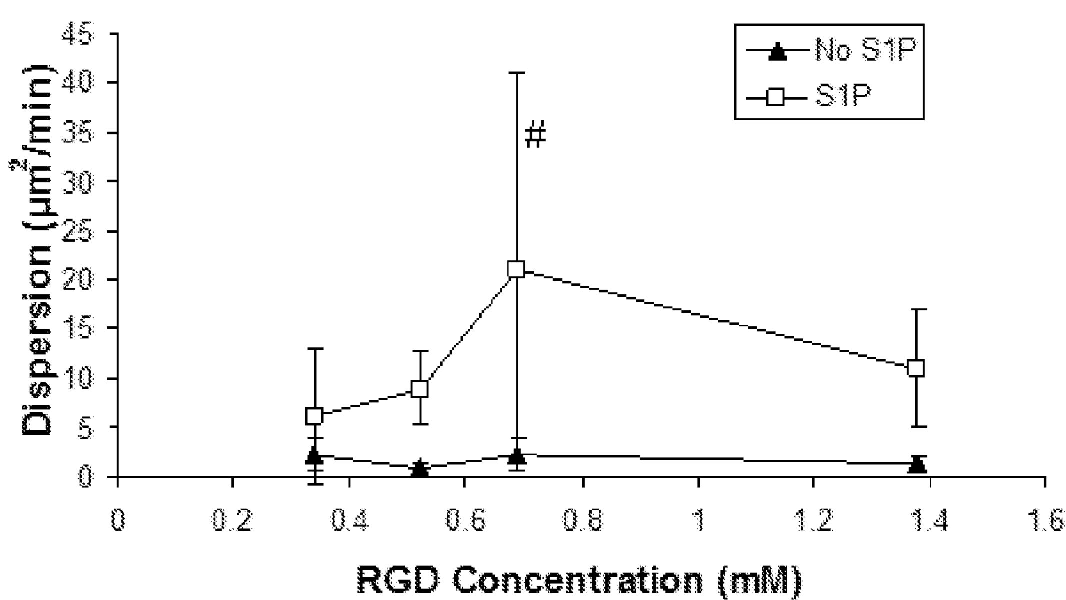

On the cyclic RGD-containing hydrogels in the absence of S1P, the persistence time did not change significantly with RGD concentration (FIG. 21*b*). With 100 nM S1P, persistence time was not significantly changed compared to no S1P. Path length and cell dispersion appeared to be unchanged by RGD concentration (FIG. 22). With 100 nM S1P, persistence time was increased, but the dependence on RGD concentration was absent. With S1P, path length and dispersion were statistically greater at 0.69 mM cyclic RGD than 0.52 and 1.38 mM cyclic RGD without S1P.

Spread Cell Area

Figure 23:
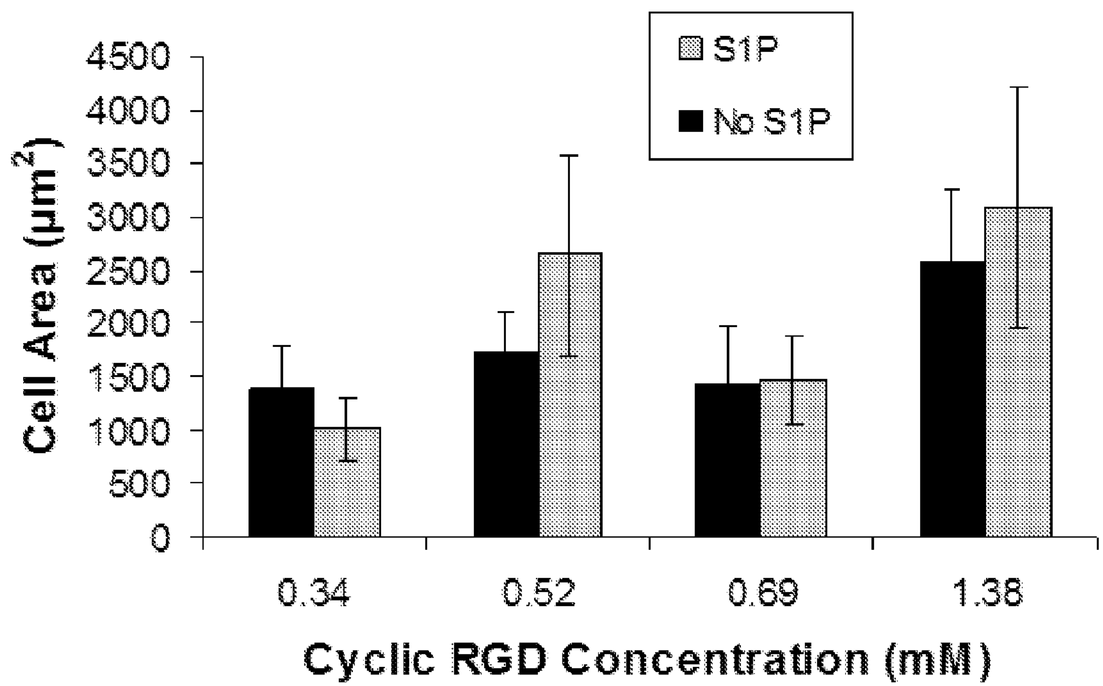
FIG. 23 depicts a graph showing cell area on various cyclic RGD concentrations. Cell area was determined by tracing cells on all RGD concentrations. No significant differences in cell area were found. Data are means±95% confidence interval based on SEM. Analysis by ANOVA Scheffe post hoc.

The projected cell area of each spread cell was measured after 3 h under 20 dyne/cm$^2$ of shear stress. A trend toward larger projected cell areas on higher cyclic RGD concentrations was observed, although the difference was not significant (FIG. 23). S1P did not seem to change this trend. As was done for the linear RGD, we split the cell areas into bins using the same quartile ranges as for the linear RGD gels. This allowed us to see if the cyclic RGD concentration caused a shift in cell area distribution. On the lower cyclic RGD concentrations, the cell area distribution shifted towards smaller cell areas compared to linear RGD, while on the highest cyclic RGD concentration, the cell area was evenly spread across the bins, indicating cell areas similar to intermediate linear RGD concentrations. No clear effect of S1P addition on cell area was apparent.

Cell Area Versus Speed

Figure 24:
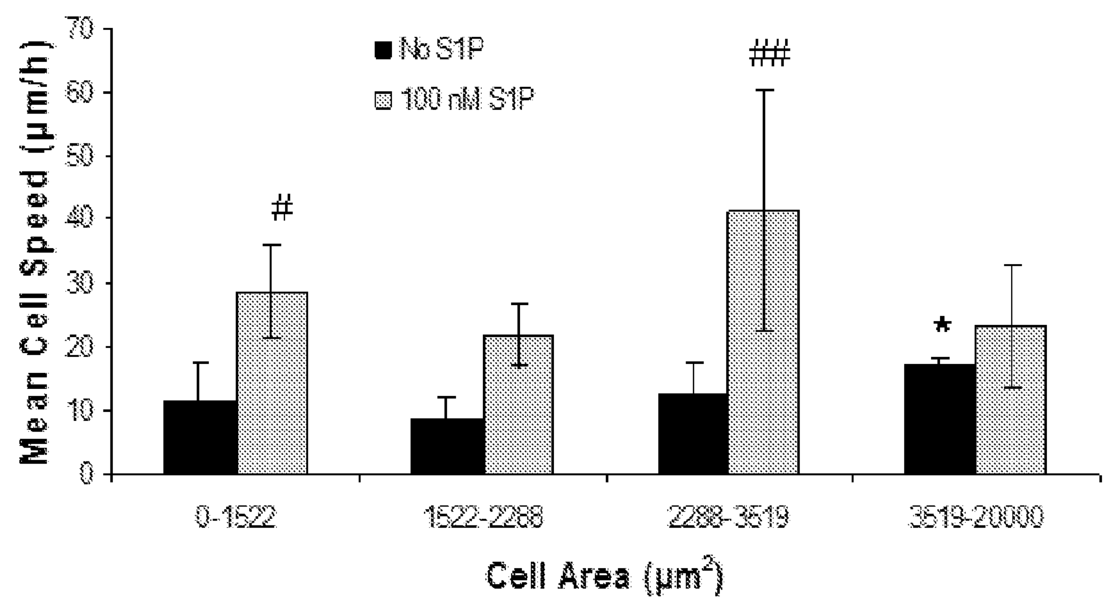
FIG. 24 depicts graphs showing the dependence of cell speed on cell area. Mean cell speed by cell area quartiles of all cyclic RGD concentrations with 100 nM S1P or no S1P. # $p<0.05$ vs. No S1P, 0-1522 and 1522-2288 $\mu m^2$. ## $p<0.05$ vs. No S1P, 0-1522, 1522-2288, and 2288-3519 $\mu m^2$. * $p<0.05$ vs. No S1P, 1522-2288 $\mu m^2$. Data are means±95% confidence interval based on SEM. Analysis by ANOVA Scheffe post hoc.
Figure 25:
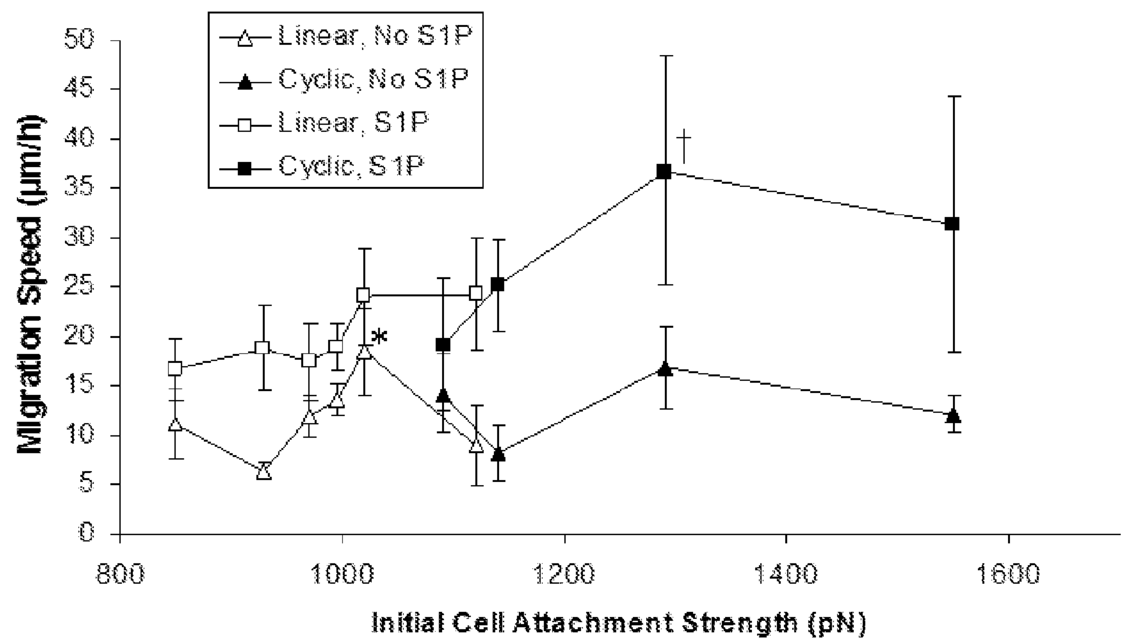
FIG. 25 depicts a graph showing cell speed versus attachment strength on linear and cyclic RGD. Cell speed data on linear and cyclic RGD containing hydrogels is shown as a function of the cell attachment strength on each gel. The linear and cyclic RGD data overlap forming a continuous curve. Without S1P, two peaks in migration speed are observed at 1020 and 1290 pN attachment strength. With 100 nM S1P addition, migration speed continues to increase with attachment strength from the linear RGD into the cyclic RGD attachment strength ranges. † $p<0.05$ vs. linear RGD with S1P, 928 and 970 pN. * $p<0.05$ vs. linear RGD without S1P, 928 and 1120 pN. Data are means±95% confidence interval based on SEM. Analysis by ANOVA Scheffe post hoc.

The relationship between cell speed and cell area on the cyclic RGD gels, with or without S1P, was examined. In the absence of S1P, the fastest cell speeds were seen at the highest cell areas (FIG. 24). When 100 nM S1P was added to the cells, the cell speed was significantly increased versus no S1P for cells with areas 0-1522 and 2288-3519 $\mu m^2$.

Example 9

Sphingosine 1-phosphate Enhances Endothelial Cell Migration in Platelet Poor Plasma Sphingosine 1-phosphate (S1P) is a biologically active lipid that participates in diverse cellular responses ranging from angiogenesis to immune cell trafficking (English et al., FASEB J. (2000) 14:2255-65; Lee et al., Biochem Biophys Res Commmun. (1999) 264:743-50; Mandala et al., Science (2002) 296:346-49). Stimulation of vascular endothelial cells with S1P promotes proliferation, migration, and survival in vitro, and barrier stabilization in vivo (English et al., FASEB J. (2000) 14:2255-65; Hisano et al., Blood (1999) 93:4293-99; English et al., J Hematother Stem Cell Res. (1999) 8:627-34; McVerry et al., Cell Signal (2005) 17:131-39). S1P exerts it effects through a family of G protein-coupled receptors, two of which, S1P, and $S1P_3$, are highly expressed in endothelial cells (Lee et al., Science (1998) 279:1552-55; Okamoto et al., Biochem Biophys Res Commun. (1999) 260:203-8). S1P is abundantly stored in platelets and is released upon platelet activation (English et al., FASEB J. (2000) 14:2255-65).

The concentration of S1P in human plasma is about 300 nM. S1P concentration in serum is substantially higher, between 500 and 1000 nM, consistent with the release of S1P from activated platelets (Murata et al., Biochem J. (2000) 352(3):809-15; Deutschman et al., Am Heart J. (2003) 146: 62-68). In vivo, the concentration of S1P in the circulation is much higher than the reported KD for the interaction of S1P with the receptor $S1P_1$, which is about 8 nM (Lee et al., Science (1998) 279:1552-55). This apparent discrepancy is explained by the binding of S1P to lipid transporters in the bloodstream, such as high density lipoprotein and albumin (Murata et al., Biochem J. (2000) 352(3):809-15). However, it is unclear if S1P signaling is saturated in flowing blood, or if the local release of S1P in the vicinity of the endothelium leads to endothelial cell migration. This is a significant question in understanding healing at sites of vascular injury, where the attachment and activation of platelets would be associated with the release of S1P.

Endothelial wound healing is promoted by the presence of various platelet-derived factors, including S1P and vascular endothelial growth factor (VEGF), and the mechanical stresses imparted by flowing blood (Lee et al., Am J Physiol Cell Physiol (2000) 278:C612-18; Koch et al., J. Immunol. (1994) 152:4149-56; Sprague et al., J Vasc Interv Radiol. (1997) 8:83-92; Braddon et al., Tissue Eng. (2002) 8:695-708). In vitro studies employing a wide range of serum concentrations (0.1-20%) have identified VEGF and fluid shear stress as migration-promoting stimulants for endothelial cells, (Koch et al., J. Immunol. (1994) 152:4149-56; Sprague et al., J Vasc Interv Radiol. (1997) 8:83-92; Hsu et al., Biochem Biophys Res Commun. (2001) 285:751-59; Albuquerque et al., Am J Physiol Heart Circ Physiol (2000) 279:H293-302; Rousseau et al., Oncogene (1997) 15:2169-77), but S1P is responsible for a large measure of the chemotactic activity of serum (English et al., FASEB J. (2000) 14:2255-65). Furthermore, studies conducted in low serum medium suggest that the combination of S1P and VEGF or fluid flow results in a synergistic increase in endothelial cell migration into a wound area (Hughes et al., Ann Biomed Eng. (2005) 33:1003-1014). While experiments conducted in low serum medium are useful for elucidating the effects of individual cell stimulants, it is difficult to extrapolate these results to the more complex in vivo environment. To begin to address these issues using human cells and human plasma, we have investigated the role of S1P in promoting endothelial cell migration in flow. Platelet poor plasma provides a physiologically-meaningful environment to study the effects of migration-promoting factors. It contains all of the noncellular components of blood, many of which may potentially activate signaling pathways that lead to cell migration.

We demonstrate that S1P added to platelet poor plasma promotes endothelial migration in both static and flow conditions. Higher concentrations of S1P are required in platelet poor plasma as compared to low serum medium, but the exogenous S1P concentration required to evoke the highest observed migration response is lower than the endogenous S1P concentration in serum. Additionally, platelet poor plasma alone significantly increases the mRNA level of $S1P_1$, versus low serum medium. Despite the activation of multiple signaling cascades that promote endothelial cell migration by flowing platelet poor plasma, increasing the plasma concentration of S1P further stimulates cell migration. Thus, through the local release of S1P, activated platelets may contribute to the endothelialization of injured blood vessels and implanted biomaterials.

Methods for Example 9

Endothelial Cell Culture—Human umbilical vein (HUVEC) or human aortic (HAEC) endothelial cells from Cambrex, Inc (Walkersville, Md.) were maintained in growth medium (MCDB 131 medium supplemented with 10 ng/mL epidermal growth factor, 10 μg/mL heparin, 1.0 μg/mL hydrocortisone, 1.0 mL/L antibiotic-antimycotic (100×) solution (Invitrogen, Carlsbad, Calif.), 2% fetal bovine serum (FBS), and 6 mg/L of bovine brain extract (Clonetics). S1P was purchased from Biomol (Plymouth Meeting, Pa.). Recombinant human VEGF-165 was purchased from Chemicon (Temecula, Calif.). HUVEC and HAEC were used for experiments between passages 3-7. Low serum medium (LSM) is MCDB 131 with 0.1% FBS and 1% antibiotic-antimycotic. D-PBS is 137 mM NaCl, 8 mM $Na_2HPO_4.7H_2O$, 0.7 mM $CaCl_2$, 2.7 mM KCl, 1.5 mM $KH_2PO_4$, 0.5 mM $MgCl_2$.

Platelet Poor Plasma Preparation—Whole blood anticoagulated with 3.5 U/mL heparin was collected from human donors via venipuncture according to Washington University HSC protocol 04-0977. Platelet poor plasma ('plasma') was produced by centrifuging at 300 g for 20 min at room temperature, to produce platelet rich plasma, which was further centrifuged at 1500 g for 15 min to produce platelet poor plasma. The plasma was passed through a 0.22 μm PVDF syringe filter. Plasma was aliquoted and stored at −20° C. VEGF concentration was measured with a sandwich ELISA kit (Quantikine Human VEGF kit, R&D Systems, Minneapolis, Minn.). The concentration of VEGF was measured in plasma samples from three different donors.

Migration Assay—HUVEC were serum-starved in low serum medium (LSM) for 12 h. A scrape wound was made using a 1000 μL plastic pipette tip in a cross pattern through a monolayer of HUVEC (average diameter=423±30 μm). After rinsing with D-PBS, LSM or plasma containing the appropriate stimulants were added to the cells. Images were taken with a 4× objective using an Olympus X71 (Olympus, Melville, N.Y.) inverted microscope at 0, 24 and 48 h. Cells were manually counted using ImagePro Express software (Media Cybernetics, Silver Spring, Md.). The density of cells in the original scrape wound area at 24 and 48 h is reported.

Application of Shear Stress—Shear stress was applied using a spinning disk system, as described previously (English et al., FASEB J. (2000) 14:2255-65). After a 12 h serum starvation, the lid of the 6-well plate was replaced with a lid fitted with three 12V DC motors, as described previously (Hughes, S. K. et al., *Ann Biomed Eng,* 2005. 33(8): 1003-1014). A 2.54 cm diameter Teflon disk was mounted onto the spindle of each motor so that the bottom of the disk was 0.5 cm above the cell monolayer. A total volume of 6 mL of medium was added per well. The motors were driven using a 1.5 V power source resulting in a rotation rate of 150±5 rad/s. The wall shear stress, as experienced by the cell monolayer, was calculated by computational fluid dynamics to be 2.57±0.12 dyne/cm2 in a region spanning 0.8-1.2 cm from the center of the well. Cell densities were counted at four locations, each between 0.8 and 1.2 cm away from the center of the well.

Quantitative Real Time Reverse Transcription PCR—In experiments with fluid flow, cell lysates were harvested only in the region of relevant shear stress (0.8-1.2 cm from the center of the well). For conditions without fluid flow, cell lysates were collected from the entire well. Total cell RNA was isolated using an RNeasy kit (Qiagen). Amplification of an 81-bp fragment of S1P1 using primers (5'-CTGTCAGC-CTCCGTGTTCAGT [SEQ ID NO:7] and 5'-TCGC-CATCGCCATTGAGCGCTATA [SEQ ID NO:8], IDT Inc, Coralville, Iowa) and probe ($S1P_1$ Probe: 5'FAM-TCG CCA TCG CCA TTG AGC GCT ATA-TAMRA 3' [SEQ ID NO:9], IDT Inc) was performed using the Quantitect qRT-PCR kit (Qiagen). The amount of $S1P_1$ or β-Actin RNA was quantified by comparing data to a standard curve generated using the Taqman human endogenous β-actin control kit (Applied Biosystems). The β-actin control kit contains 333 copies of β-actin DNA per ng of total RNA.

Knockdown of $S1P_1$ with siRNA—Passage 3 HUVEC at 30-50% confluence were transfected with 100 nM siRNA targeting $S1P_1$ (Silencer validated siRNA against $S1P_1$, Ambion, Austin, Tex.) in antibiotic-free growth medium using Lipofectamine-2000 (Invitrogen). After 6 h, the cells were rinsed with D-PBS and fresh growth medium was added. At 48 h, cells were incubated with LSM for 12 h. A negative control (Ambion, Silencer Negative Control #2) was used to test for non-specific effects on gene expression or cell survival. Quantitative real-time RT-PCR was used to determine the extent of $S1P_1$ receptor mRNA knockdown 48 h after transfection.

Individual Cell Migration of HAEC—Passage 6 HAEC were subcultured and incubated in growth medium for 3 days and then were serum-starved for 12 h. HAEC cell densities were less than 100 cell/mm$^2$ so that cell-cell contacts were unlikely during the duration of the experiment. Any cell that contacted another cell was excluded from data analysis. Plasma was buffered with 20 mM HEPES, pH 7.4, and added to the well. Time-lapse microscopy was used to track the cells every 4 min for 12 h with a 10× objective. The migration speed of individual cells was analyzed using ImageJ software (NIH).

Statistical Analysis—Data is presented as mean±standard deviation. Significant differences were determined by ANOVA and post-processing with the Scheffe test ($p<0.05$).

Figure 26A:
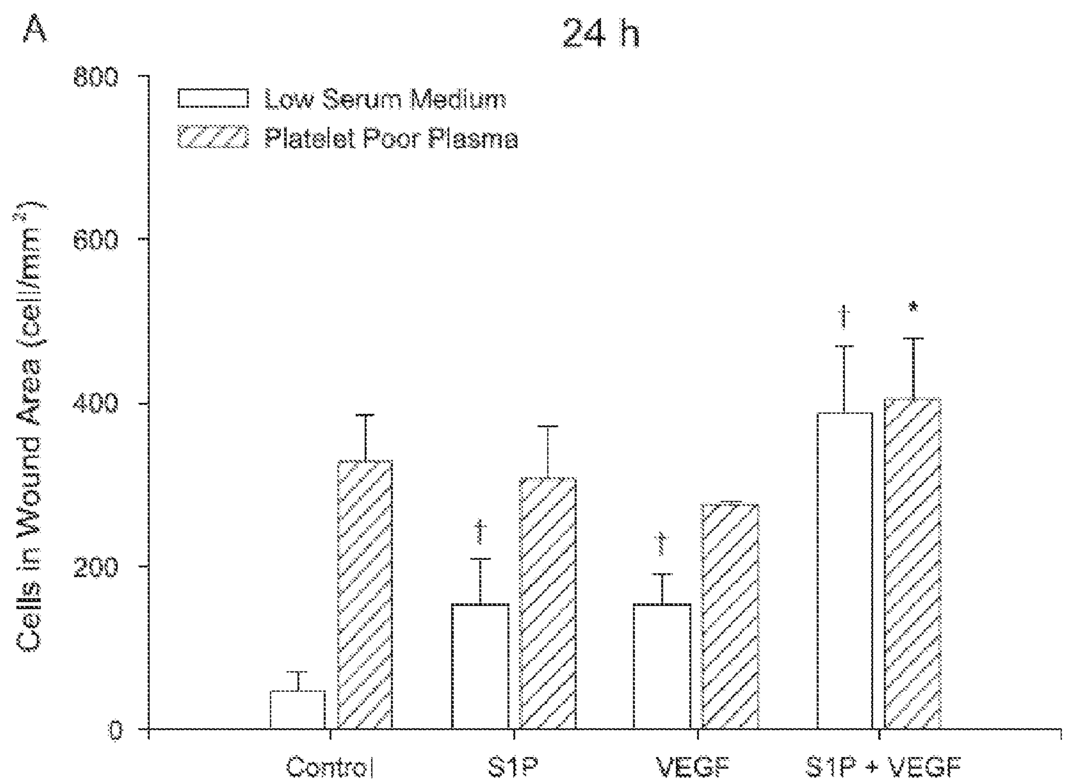
FIG. 26 depicts graphs showing that plasma promoted an increase in the number of cells in a scrape wound versus low serum medium in the absence of flow. A. (24 h), B. (48 h), HUVEC were cultured in LSM (white bars) or plasma (hatched bars) and 100 nM S1P, 10 ng/mL VEGF or both. †$P<0.05$ versus LSM alone (only LSM conditions marked). *$P<0.05$ versus plasma alone (only plasma conditions marked).
Figure 26B:
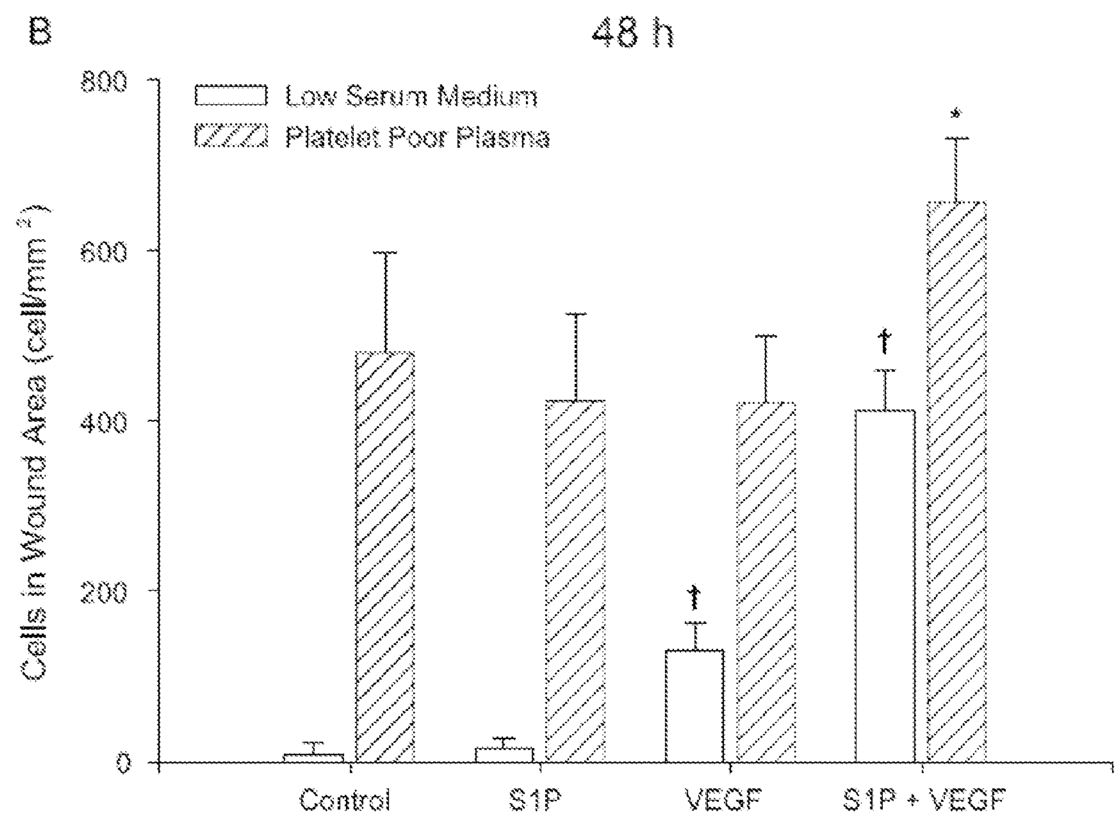

In Vitro Response of HUVEC to S1P+VEGF is Similar in Platelet Poor Plasma and LSM Addition of human platelet poor plasma (subsequently referred to as 'plasma') to serum starved HUVEC resulted in a significant increase in the number of cells in a scrape wound at 24 and 48 h, versus low serum medium (LSM) (FIG. 26). When exogenous S1P (100 nM) or VEGF (10 ng/mL) were added to plasma, there were no differences in the numbers of cells in the scrape wound versus plasma alone. This differs from the response observed in LSM. The addition of 100 nM S1P to LSM increased the number of endothelial cells in a scrape wound versus LSM alone at 24 h. By 48 h, LSM leads to substantial cell death, which is not prevented by 100 nM S1P (Lee et al., (2000) Am J Physiol Cell Physiol 278:C612-18; Hughes et al., Ann Biomed Eng (2005) 33:1003-14), and our current results are consistent with this finding. In LSM, there is a synergistic effect when both S1P (100 nM) and VEGF (10 ng/ml) are added to HUVEC, versus addition of VEGF or S1P alone (Hughes et al., Ann Biomed Eng (2005) 33:1003-14). Upon the addition of 100 nM S1P and 10 ng/mL VEGF to plasma (n=3) there was a statistically significant increase in the number of cells in the scrape wound area, versus plasma alone (n=6) (FIG. 26).

HUVEC migration into a scrape wound is increased upon the addition of 200 nM S1P to plasma HUVEC were incubated in plasma with exogenous S1P concentrations of 100, 200, 500, and 1000 nM S1P. In cultures without fluid flow, the highest number of cells within the scrape wound was observed with 200 nM exogenous S1P (FIG. 27, hatched bars). At 24 h, only plasma with 200 nM and 500 nM exogenous S1P were statistically different from plasma alone. At 48 h, only plasma with 200 nM exogenous S1P was significantly higher than plasma alone.

Exogenous S1P Increases Cell Migration in the Presence of Fluid Flow

Figure 27A:
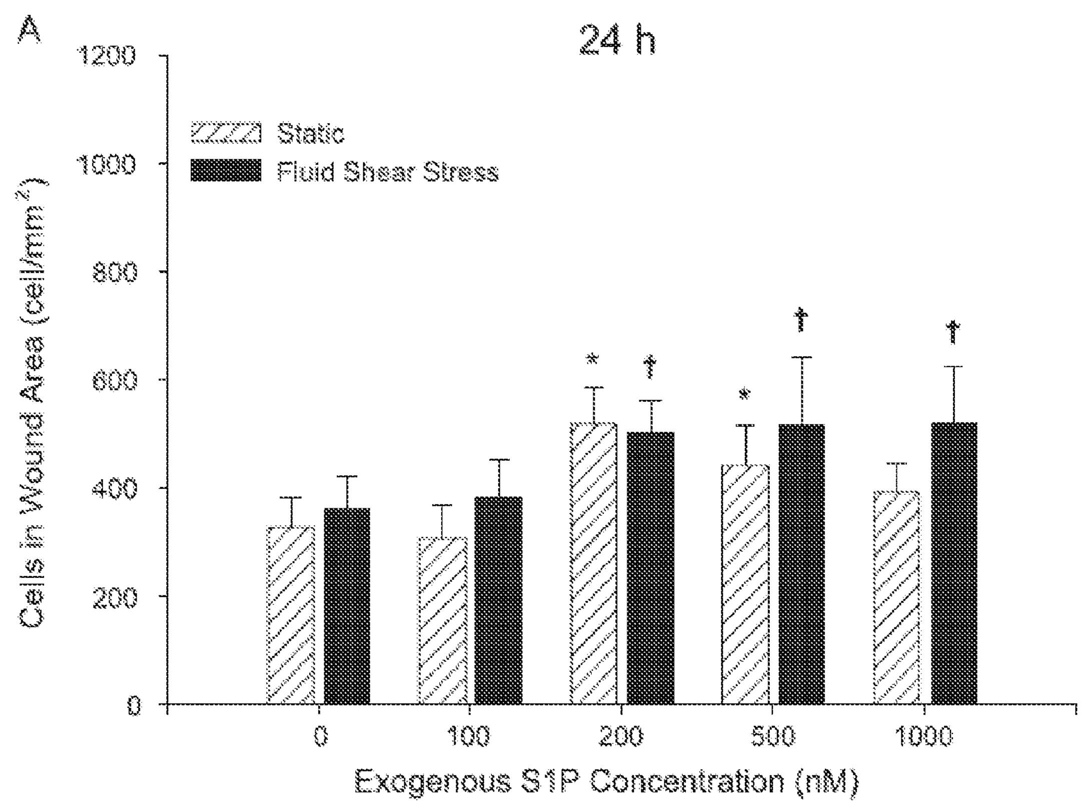
FIG. 27 depicts graphs illustrating that the addition of S1P to plasma increased the migration of endothelial cells at 24 h (A.), and 48 h (B.). Scrape-wounded HUVEC in plasma were cultured in the absence (hatched bars) or presence (black bars) of fluid flow with exogenous S1P. *$P<0.05$ versus plasma alone without flow. †$P<0.05$ versus plasma alone in the presence of flow. C. Individual cell speeds were measured for HAEC in plasma in the absence of flow with exogenous S1P. *$P<0.05$ versus plasma alone. †$P<0.05$ versus 200 nM S1P. D. Summary of data from FIGS. 1 and 2, comparing results at 24 h and 48 h for combinations of S1P, VEGF and flow. *$P<0.05$ versus plasma alone at the same time point.
Figure 27B:
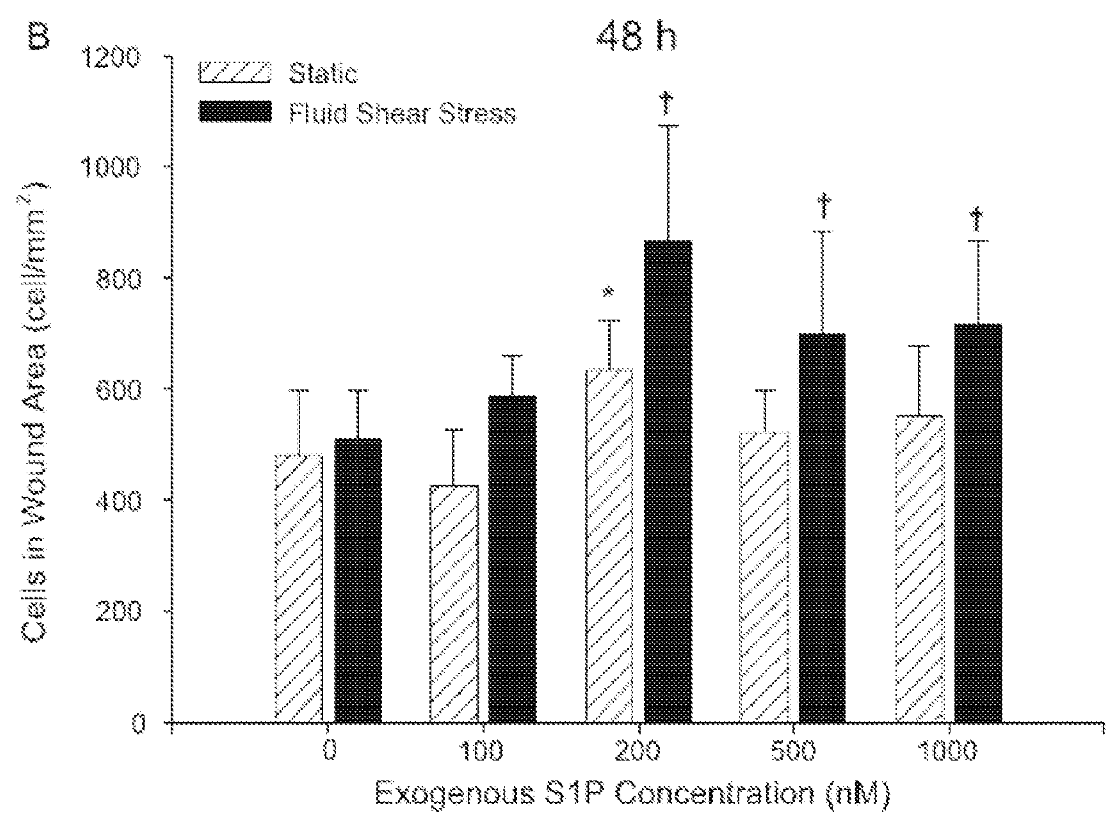

In LSM, the application of fluid flow to HUVEC results in a significant increase in cell migration into a scrape wound (Hughes et al., Ann Biomed Eng (2005) 33:1003-14). There was no significant increase in the number of cells within the scrape wound when fluid shear stress was applied to HUVEC in plasma (FIG. 27B, solid bars). The addition of 100 nM S1P to plasma in the presence of fluid flow did not significantly increase the number of cells in the scrape wound (summarized in FIG. 27C). Increasing the plasma concentration of S1P by 200, 500, or 1000 nM led to significant increases in the number of cells in the wound area at 24 h, versus plasma alone. At 48 h, migration into the wound area with 200 nM exogenous S1P was significantly different from plasma alone. There was no significant difference in the cell density in the wound area between 200, 500, and 1000 nM S1P at either 24 or 48 h in the presence of fluid flow.

Exogenous S1P Increases the Migration Speeds of HAEC in Plasma Culture

Figure 27C:
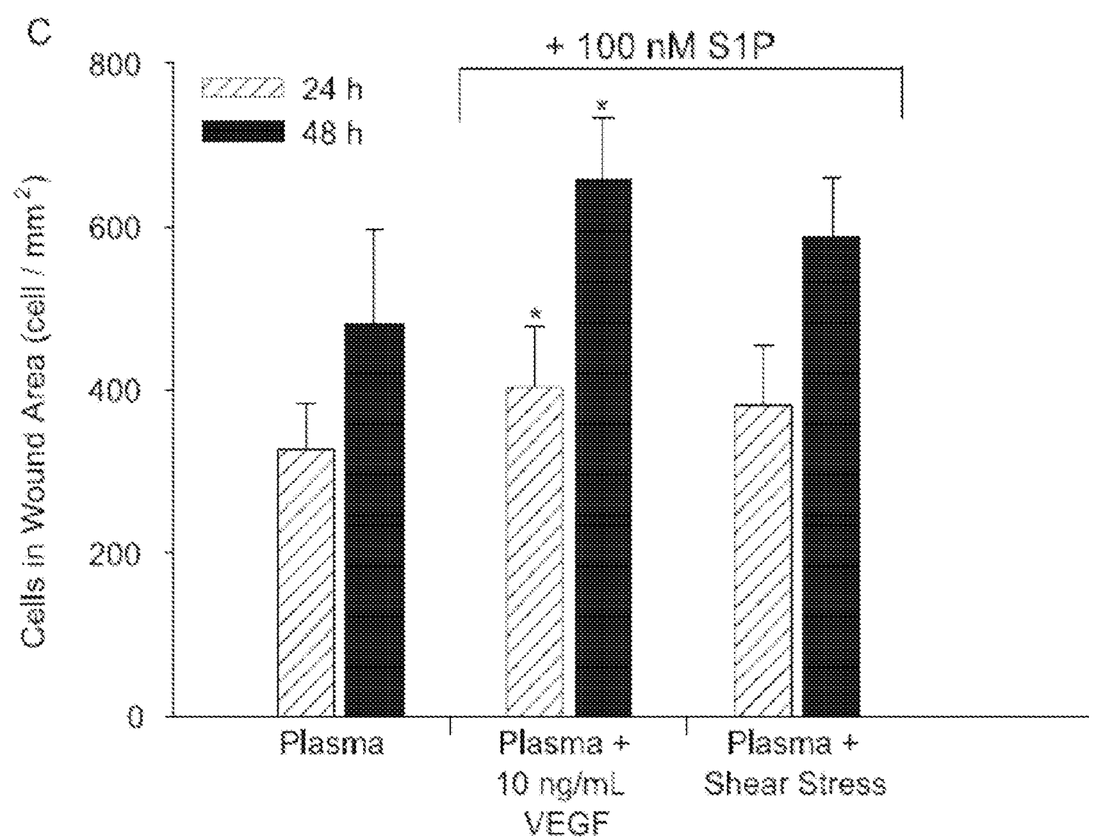
Figure 27D:
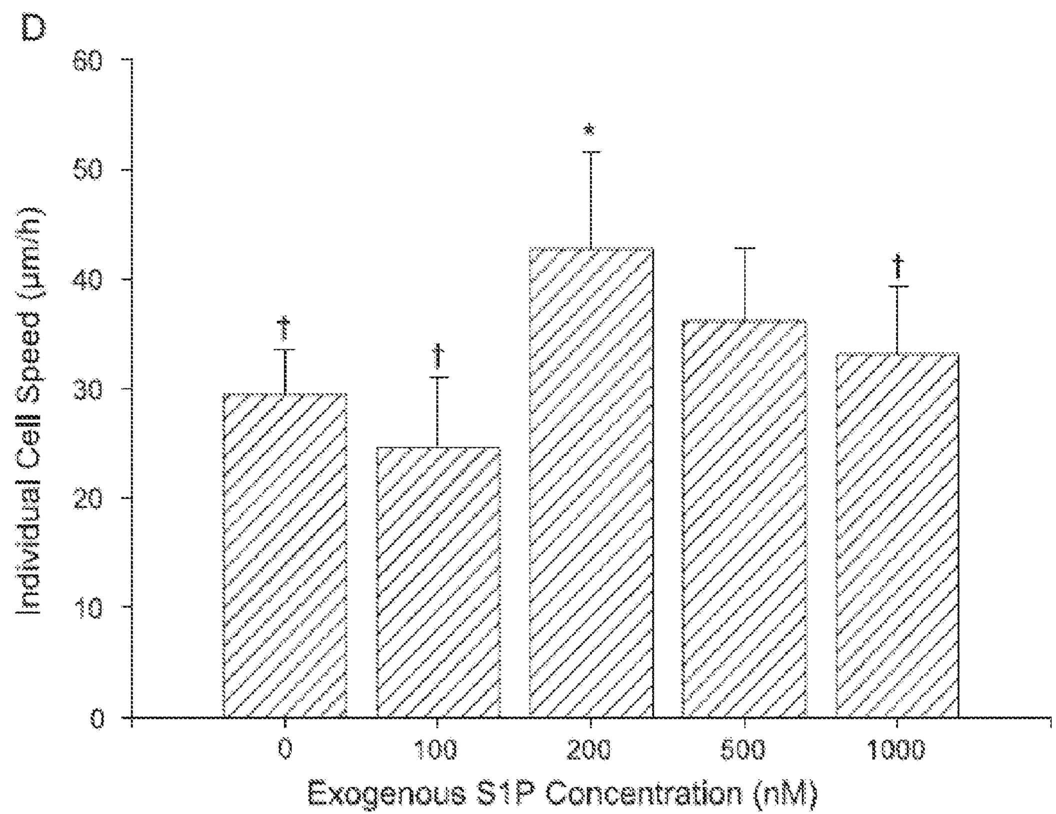

To determine if the addition of S1P to plasma affects arterial cells similarly, individual cell migration speeds were measured for HAEC in static plasma using time-lapse microscopy. Similar to the results obtained with HUVEC, there was no difference between the mean cell speeds (μm/h) when 100 nM S1P was added to the plasma, versus plasma alone (FIG. 27D). When the concentration of S1P in plasma was increased by 200 nM, the mean cell speed was significantly increased, versus plasma alone ($p=0.023$). Increasing the exogenous S1P concentration further (500 and 1000 nM) did not lead to a significant increase in mean cell speed versus plasma alone.

Exogenous S1P Does Not Increase Total Cell Density Outside the Wound Area

Figure 28:
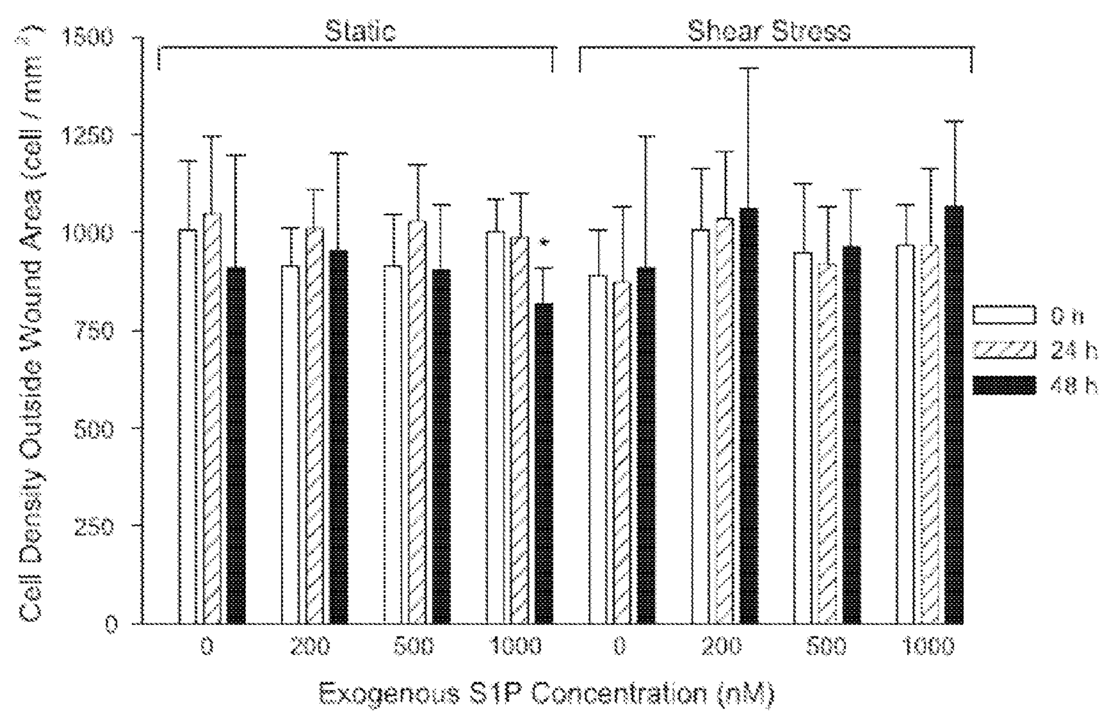
FIG. 28 depicts a graph showing that the cell density outside of the wound area did not change with increasing concentrations of exogenous S1P in plasma, except at 1000 nM S1P. *$P<0.05$ versus 1000 nM S1P at t=0 h.

Cell survival effects impact the cell density outside of the scrape wound area (Hughes et al., Ann Biomed Eng (2005) 33:1003-14). There were no significant differences in cell densities outside the scrape wound area between the different exogenous S1P levels (0, 200, 500, and 1000 nM) at each time point (FIG. 28). However, 1000 nM exogenous S1P in static culture resulted in a significantly lower cell density outside the scrape wound at 48 h versus 0 and 24 h ($p=0.003$ and 0.007).

Figure 29A:
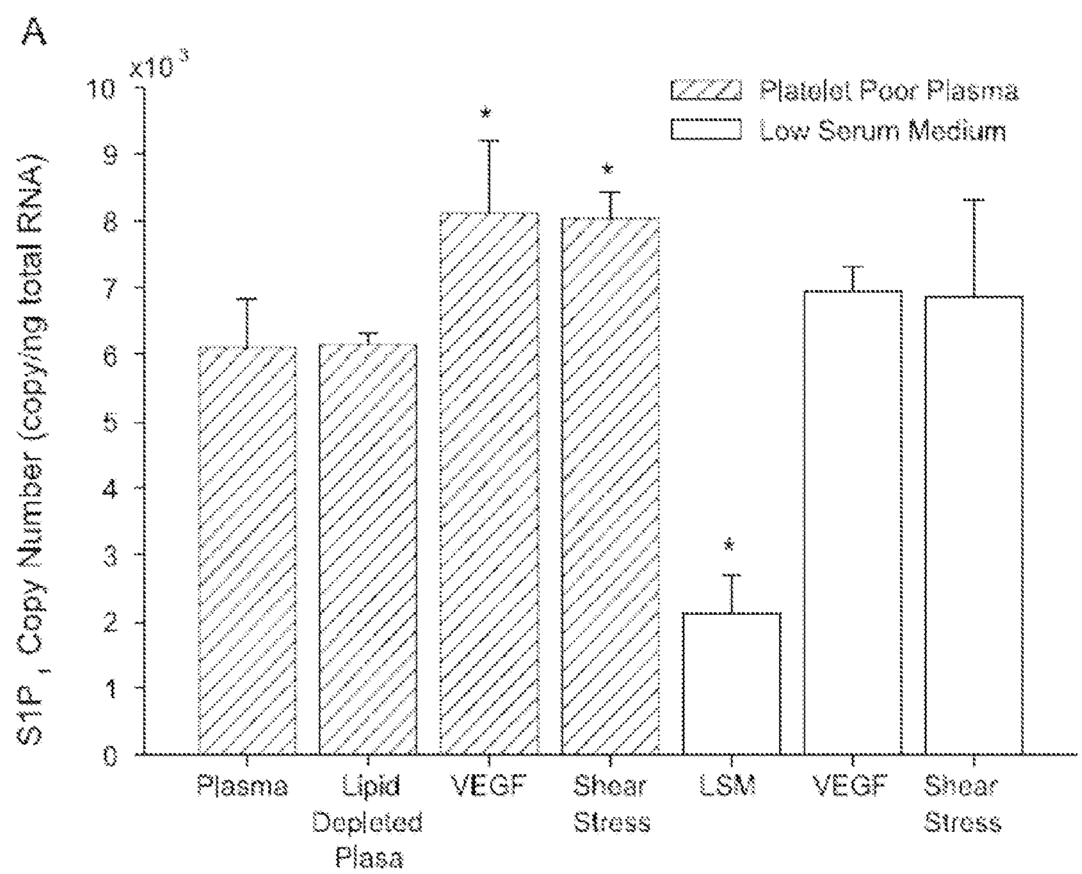
FIG. 29 depicts graphs showing that $S1P_1$ mRNA concentration was increased in plasma versus low serum medium. A further increase was seen upon the addition of 10 ng/mL VEGF or 2.57 dyne/$cm^2$ fluid shear stress. A. S1P1 copy number was measured using quantitative real-time RT-PCR. *$P<0.05$ versus plasma alone. B. VEGF concentration in plasma was not elevated during blood collection and processing.

Elevated S1P1 mRNA Concentration in Plasma is Not Due to Platelet-Released VEGF or S1P In LSM, the expression of S1P1 is dramatically increased in HUVEC exposed to fluid shear stress or 10 ng/mL VEGF (Hughes et al., Ann Biomed Eng (2005) 33:1003-14; Takada et al, Biochem Biophys Res Commun. (1997) 240:737-41; Igarashi et al, PNAS (2003) 100:10664-69). The S1P1 mRNA expression level in HUVEC exposed to plasma was measured using quantitative real-time RT-PCR. The $S1P_1$ mRNA amounts were elevated after 24 h of culture in plasma, versus HUVEC cultured in LSM (FIG. 29A). The increase in $S1P_1$ mRNA levels was similar to that seen when HUVEC were exposed to either 10 ng/mL VEGF in LSM or fluid shear stress with LSM (FIG. 29A) (Hughes et al., Ann Biomed Eng (2005) 33:1003-14). Furthermore, the addition of fluid shear stress or 10 ng/mL VEGF to HUVEC cultured in plasma resulted in a statistically significant increase in the $S1P_1$ mRNA concentration, versus plasma alone at 24 h (FIG. 29A).

Figure 29B:
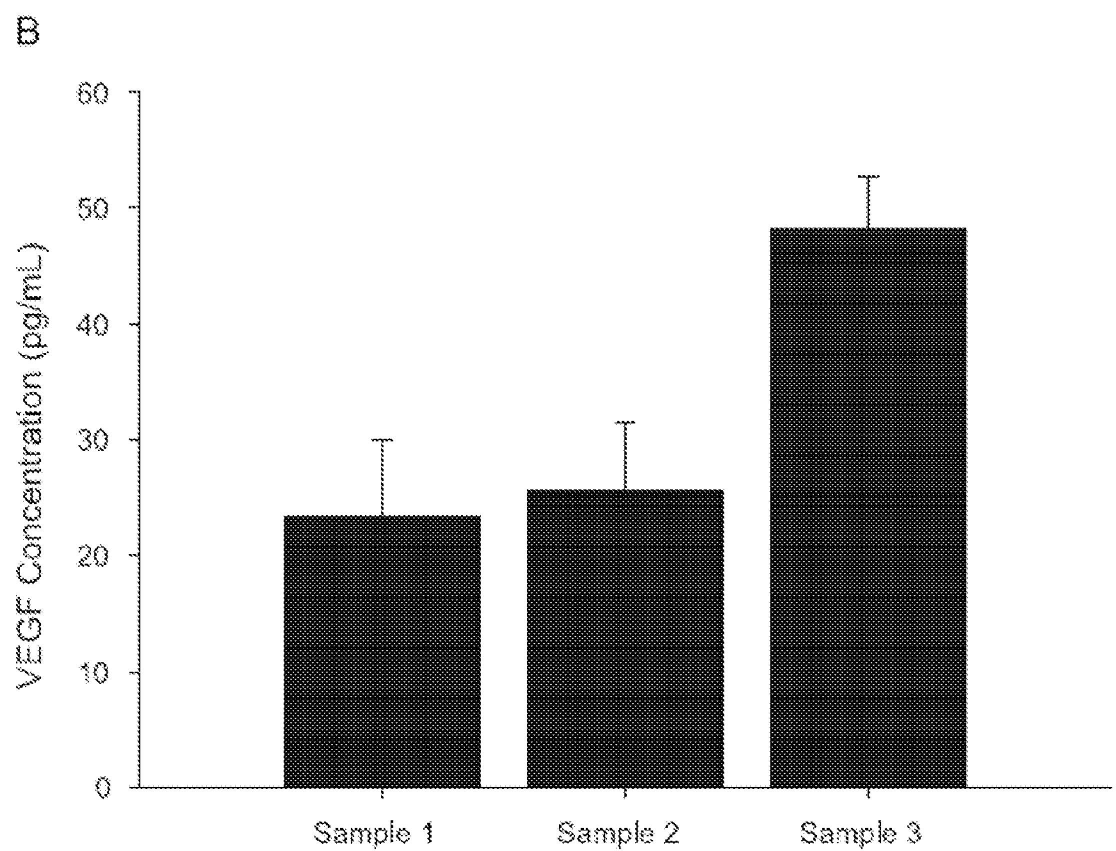

In LSM, VEGF concentrations between 5 and 10 ng/mL are required to achieve an increase in $S1P_1$ mRNA concentration similar to that measured for HUVEC cultured in plasma (Hughes et al., Ann Biomed Eng (2005) 33:1003-14). To determine if the increase in $S1P_1$ mRNA in plasma was due to VEGF, VEGF concentrations were measured in plasma samples from three separate donors using our blood collection protocol. The average VEGF concentration in the three samples was 32.4±12.2 μg/mL (FIG. 29B).

Lipid-depletion of plasma with activated charcoal did not affect the $S1P_1$ mRNA concentration, indicating that the lipids in plasma are not responsible for the increased $S1P_1$ mRNA expression in plasma versus LSM (FIG. 29A).

Knockdown of $S1P_1$ Decreases Scrape Wound Cell Density in Plasma

Figure 30A:
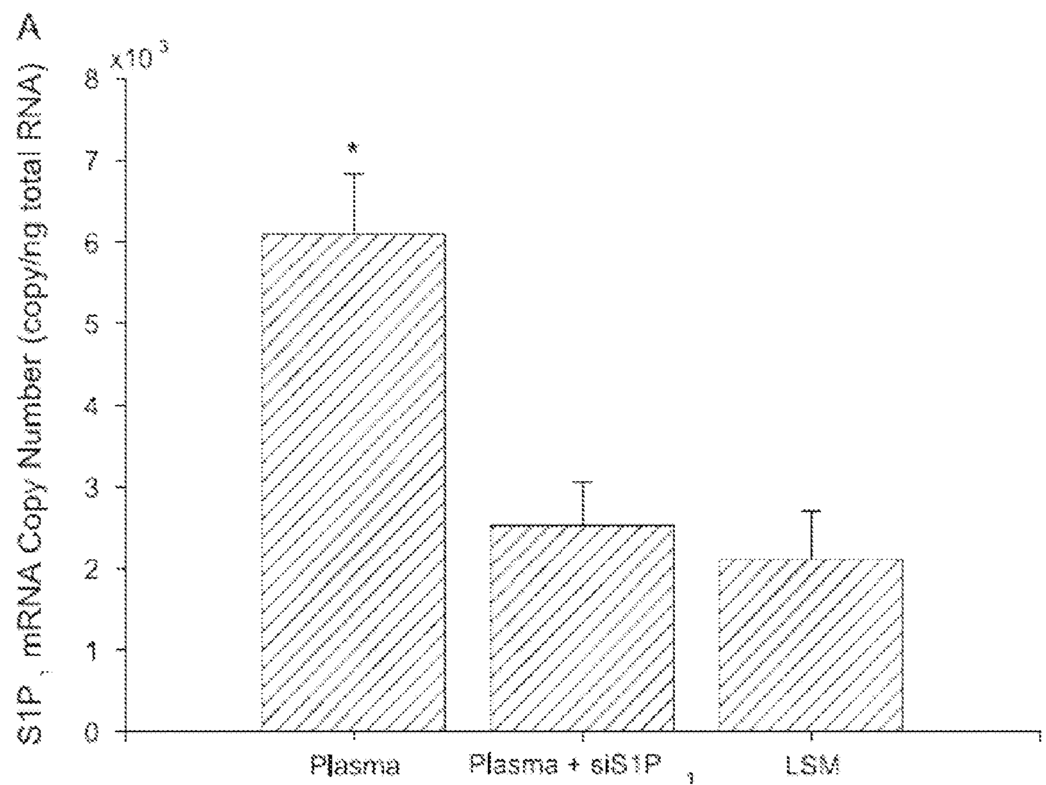
FIG. 30 depicts graphs showing that cell migration was reduced in plasma following transfection of siRNA directed towards $S1P_1$, and was similar to migration in lipid-depleted plasma. A. Transfection of 100 nM $S1P_1$ siRNA resulted in a 58±9% decrease in $S1P_1$ mRNA concentration in HUVEC cultured in plasma. *$P<0.05$ versus HUVEC+$S1P_1$ siRNA. B. Knock-down of $S1P_1$ reduced the number of cells in the scrape wound to levels seen with HUVEC in lipid-depleted plasma. *$P<0.05$ versus plasma, 24 h. **$P<0.05$ versus lipid-depleted plasma, 24 h. †$P<0.05$ versus plasma, 48 h. ‡$P<0.05$ versus lipid-depleted plasma, 48 h.
Figure 30B:
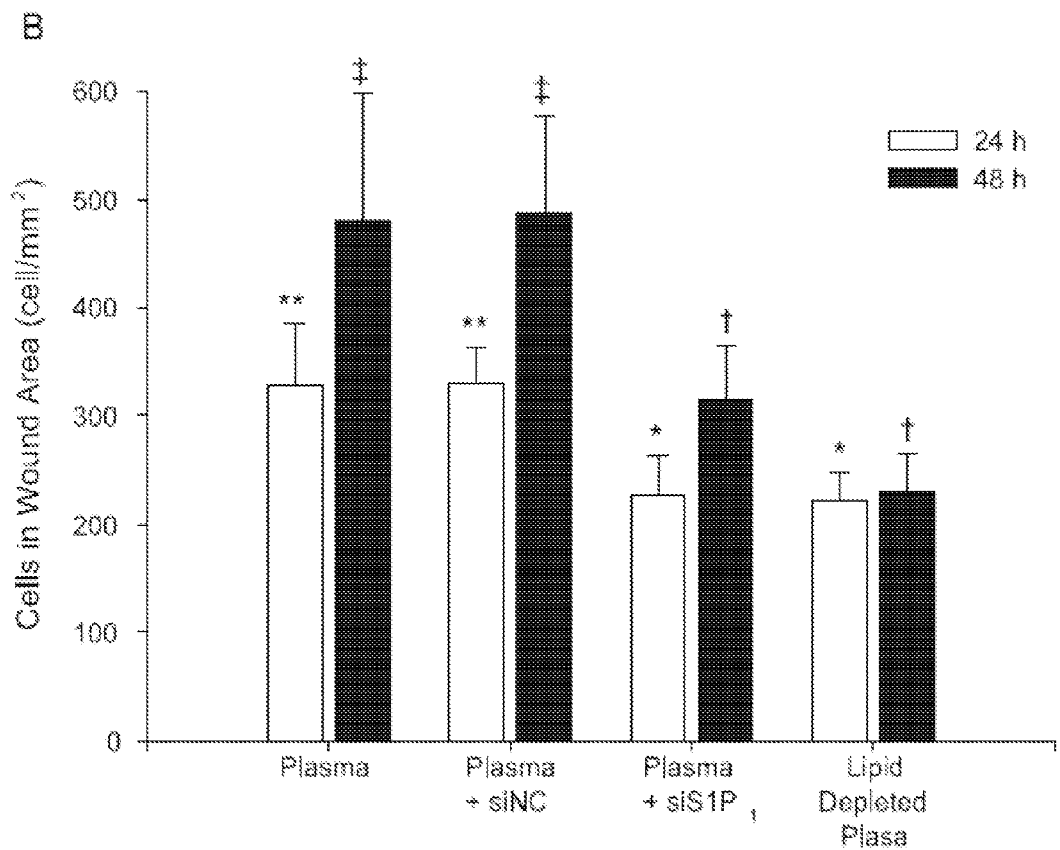

HUVEC were transfected with 100 nM siRNA directed against $S1P_1$ (FIG. 30A) and assayed for migration into a scrape wound in the absence of fluid flow (FIG. 30B). The number of cells in the scrape wound was significantly lower with plasma-stimulated HUVEC transfected with $S1P_1$ siRNA, compared to transfection with a negative control siRNA or no transfection.

Similarly, the number of cells in the scrape wound at 24 and 48 h was significantly lower in HUVEC stimulated with lipid-depleted plasma, versus plasma alone. At 24 h, the density of cells in the scrape wound was not different between S1P1-knockdown cells stimulated with plasma and HUVEC stimulated with lipid-depleted plasma.

Discussion

The effects of platelet factors on in vivo endothelial cell migration are difficult to predict from in vitro experiments, particularly with studies conducted in LSM in the absence of flow (Hughes et al., Ann Biomed Eng (2005) 33:1003-14). Platelets store S1P at high concentrations (about 150 μM) due to the presence of sphingosine kinase and the absence of S1P lyase (Yatomi et al., J Biochem (Tokyo) (2004) 136:495-502). Platelet activation in vitro results in the release of about 60% of the stored S1P (Yatomi et al., J Biochem (Tokyo) (2004) 136:495-502). Release of S1P from activated platelets in vivo should lead to a transient but substantial increase in the concentration of S1P in the milieu of the endothelial cell.

Human platelet poor plasma was used to study human endothelial cell responses to exogenous S1P. Important differences were observed in the migration response to plasma versus low serum medium. Plasma alone induced an increase in the mRNA concentration of $S1P_1$, resulting in a copy number that was approximately three times higher than LSM (Hughes et al., Ann Biomed Eng (2005) 33:1003-14).

The mRNA copy number measured after exposure to plasma was similar to that measured in HUVEC cultured in LSM supplemented with 10 ng/mL VEGF, or HUVEC in LSM exposed to 2.57 dyne/$cm^2$ fluid shear stress (Hughes et al., Ann Biomed Eng (2005) 33:1003-14). It has been previously demonstrated that an increase in $S1P_1$ mRNA concentration is correlated with an increase in $S1P_1$ protein expression, and an increase in the amount of $S1P_1$ receptor leads to greater sensitivity towards S1P (Igarashi et al., PNAS (2003) 100:10664-69).

While increasing the S1P concentration in plasma to 200 nM led to a large, significant increase in cell migration, increasing S1P concentration in plasma by 100 nM had only a small effect. This may be explained by changes in the free S1P concentration, which is a function of the concentration of lipid binding proteins. In blood, S1P binds to plasma lipoproteins, with HDL binding about 55% of circulating S1P and other lipoproteins binding about 10% (FIG. 6C)(Murata et al., Biochem J (2000) 352(3):809-15; Aoki et al., J. Biochem (2005) 138:47-55). S1P also binds to albumin, but changing the concentration of albumin in cell culture medium does not affect S1P-induced cell responses (Yatomi et al., Blood (2000) 96:3431-38). In contrast, the addition of increasing amounts of serum to S1P-containing medium retards S1P signaling. This inhibition is likely due to the lipoprotein component of serum (Murata et al., Biochem J (2000) 352(3):809-15; Aoki et al., J. Biochem (2005) 138:47-55). A KD for binding of S1P to HDL particles has not been reported, and accurate measurement of equilibrium binding constants for lipids is challenging (Hamilton, J Lipid Res (1998) 39:467-81). It has been found that S1P in plasma (about 300 nM) stimulates cell migration to the same extent as 7.3 nM S1P in low serum medium (Murata et al., Biochem J (2000) 352(3): 809-15). It is likely that this is due to the low concentration of free S1P in plasma, which may be at or below the KD for S1P/$S1P_1$ binding (8 nM) (Lee et al., Science (1998) 279: 1552-55; Murata et al., Biochem J (2000) 352(3):809-15). Due to the high concentration of HDL in blood relative to S1P, addition of S1P to plasma should lead to relatively small increases in the free or 'active' concentration of S1P compared to the total amount added (Clark et al., Int J Epidemiol (2003) 32:125-30).

Addition of VEGF or fluid flow to plasma did not significantly increase the number of cells in the scrape wound, versus plasma alone. However, $S1P_1$ mRNA concentrations were significantly increased beyond the already elevated levels found in plasma (FIG. 29A). The absence of a significant increase in migration, despite an increase in $S1P_1$, may be attributed to the small magnitude of the increase in $S1P_1$, the low concentration of free S1P in plasma, and the high variance associated with the scrape wound model. The combination of increasing the plasma concentration of S1P by 100 nM and the addition of VEGF or fluid flow did cause an increase in the number of cells in the scrape wound (FIG. 27C). In contrast, increasing the S1P concentration in plasma by 200-1000 nM led to levels of endothelial cell migration in the presence of fluid flow that indicated a saturation in migration signaling due to S1P (FIGS. 27A & B). This may be a reflection of the characteristics of the binding curve of S1P to $S1P_1$ combined with an inhibition of cell migration at the higher concentrations.

The reduction in the migration response at higher S1P concentrations (500 and 1000 nM exogenous S1P) in the absence of flow is consistent with results obtained in LSM using Boyden chambers, in which a peak in the level of cell migration was observed at 100 nM (Yatomi et al., Blood (2000) 96:3431-38; Okamoto et al., Mol Cell Biol. (2000) 20:9247-61). In smooth muscle cells, S1P inhibits cell migration at physiological concentrations, but enhances migration at higher concentrations due to signaling through low abundance S1P receptors (Boguslawski et al., Exp Cell Res. (2002) 274:264-74). The existence of less abundant or lower affinity S1P receptors may cause a similar action in vascular endothelial cells, as orphan G protein-coupled receptors have been shown to respond to S1P stimulation (Uhlenbrock et al., Cell Physiol Biochem (2003) 13:75-84; Yamaguchi et al., Biochem J (2003) 374:715-22). Alternatively, lipid phosphate phosphatases present in the plasma membrane of endothelial cells convert S1P to sphingosine (Aoki et al., J. Biochem (2005) 138:47-55; Brindley et al., Biochim Biophys Acta (2002) 1582:33-44). Sphingosine can be transported across the plasma membrane of endothelial cells (Aoki et al., J. Biochem (2005) 138:47-55). The sphingosine transported into the cytoplasm may be converted to ceramide by the action of ceramide synthase, perturbing the balance that is maintained between intracellular S1P and ceramide that may result in apoptosis (Le Stunff et al., J. Cell Biol. (2002) 158:1039-49). If cell survival were affected by the addition of S1P to plasma, the cell density outside of the wound area would decrease over time. At 48 h, our experiments showed a significant difference in the cell density outside the wound area with 1000 nM exogenous S1P in the absence of flow, versus 0 and 24 h. This was not observed in the presence of flow. Fluid shear stress has been shown to reduce apoptosis, even in the presence of apoptotic factors (Dimmeler et al., FEBS Lett (1996) 399:71-74). The cell density outside of the scrape wound also did not significantly increase when different concentrations of S1P were added to plasma. This suggests that cell migration, not proliferation, was responsible for the increase in the number of cells in the scrape wound at higher S1P concentrations. An increase in migration rates was also demonstrated by measuring individual cell speeds of HAEC in plasma, showing a significant increase with the addition of 200 nM S1P.

The increase in the expression of $S1P_1$ mRNA was not due to S1P or VEGF in the plasma used in these experiments. With HUVEC, a VEGF concentration greater than 5 ng/mL in LSM is required to achieve the $S1P_1$ mRNA copy number that we measured with plasma (Hughes et al., Ann Biomed Eng (2005) 33:1003-14). It is possible that plasma collection and processing led to substantial platelet activation and an increase in the concentration of VEGF, even in the presence of 3.5 U/ml heparin. However, the VEGF concentration measured in plasma (32.4±12.2 μg/mL) was substantially lower than the concentration required for S1P1 mRNA elevation in LSM (FIG. 29B). The VEGF concentration measured was within reported human plasma levels of VEGF (9-150 μg/ml) (Rodriguez et al., J. Immunol. Methods (1998) 219:45-55). The anticoagulant used in these experiments, heparin, has been shown to decrease the effects of VEGF on endothelial cells, also indicating that VEGF is not responsible for the upregulation of $S1P_1$ (Takahashi et al., Br J Pharmacol (2005) 146:333-43). Previous reports indicate that the addition of S1P to LSM does not increase the $S1P_1$ mRNA concentration, but the S1P concentrations tested in those studies were below the level of S1P found in human plasma (Hughes et al., Ann Biomed Eng (2005) 33:1003-14; Igarashi et al., PNAS (2003) 100:10664-69). Lipid-depletion of the plasma through charcoal extraction did not lower the concentration of $S1P_1$ mRNA, indicating that the lipids in plasma do not influence the expression of $S1P_1$ mRNA. In conclusion, we have shown that an increase in S1P concentration in plasma leads to an increase in both endothelial scrape wound healing and cell migration speeds.

What is claimed is:

1. A substrate comprising a plurality of cross-linked, distinctly-formed layers, the plurality of cross-linked, distinctly-formed layers comprising at least three layers wherein the at least three layers comprise a first water soluble polymer layer, a second protein layer, and a third water soluble polymer layer, wherein the first water soluble polymer layer comprises a water soluble polymer that comprises a reactive group selected from the group consisting of sulfones, sulfoxides, sulfonates, sulfonamides, phosphonates and phosphonamides;

the second protein layer comprises at least one protein that comprises at least one lipid binding site and at least one functional group selected from the group consisting of an amino group and a sulfhydryl group; and the third water soluble polymer layer comprises a water soluble polymer that comprises a reactive group selected from the group consisting of sulfones, sulfoxides, sulfonates, sulfonamides, phosphonates and phosphonamides; and whereby the second protein layer is disposed between the first water soluble polymer layer and the third water soluble polymer layer to cross-link the first water soluble polymer layer and the third water soluble polymer layer together to form the plurality of cross-linked, distinctly-formed layers.

2. The substrate of claim 1, wherein the substrate has a porous matrix with an average pore diameter from about 1 nm to 100 μm.

3. The substrate of claim 2, wherein the substrate is a hydrogel.

4. The substrate of claim 1, wherein the water soluble polymer is selected from the group consisting of a hydrophilic polymer, cellulose derivative, polysaccharide, and poly (amino acid).

5. The substrate of claim 1, wherein the protein is albumin or a high density lipoprotein particle comprising Apo A-I and lipids.

6. The substrate of claim 1, wherein the protein has from about 2 to about 7 lipid binding sites.

7. The substrate of claim 1, wherein the protein is a lipoprotein selected from the group consisting of chylomicrons, very low density lipoproteins, intermediate density lipoproteins, low density lipoproteins, and high density lipoproteins.

8. The substrate of claim 4, wherein the water soluble polymer is polyethylene glycol.

9. The substrate of claim 1, further comprising a therapeutic molecule non covalently conjugated to the protein.

10. The substrate of claim 1, wherein the substrate further comprises a therapeutic molecule that converts an endogenous precursor form of a molecule to an active form of the endogenous molecule in a subject.

11. The substrate of claim 10, wherein the therapeutic molecule is an enzyme.

12. The substrate of claim 11, wherein the enzyme is a recombinant enzyme having an added GST tag.

13. The substrate of claim 11, wherein the enzyme is sphingosine kinase.

14. The substrate of claim 13, wherein the sphingosine kinase has an amino acid sequence encoded by a nucleic acid sequence selected from the group consisting of SEQ ID NO:1 and SEQ ID NO:2.

15. The substrate of claim 1, wherein the substrate further comprises a polypeptide that promotes adhesion of cells.

16. The substrate of claim 15, wherein the polypeptide comprises the amino acid sequence RGD.

17. The substrate of claim 1, wherein the protein is a recombinant protein having the amino acid sequence of a native protein, further comprising an added amino acid residue that reacts with the water soluble polymer to form cross-links between the protein layers and the water soluble polymer layers.

18. The substrate of claim 17, wherein the added amino acid residue is cysteine and wherein the cysteine residue is added to the recombinant protein at the N terminus, C terminus, or both.

19. The substrate of claim 18, wherein the recombinant protein has an amino acid sequence encoded by a nucleic acid sequence comprising SEQ ID NO. 3 or SEQ ID NO:4.

20. The substrate of claim 1, wherein the substrate is from about 90 percent to about 99 percent protein rejecting.

21. The substrate of claim 1, where the substrate has from about 4 to about 50 distinctly-formed layers.

22. The substrate of claim 1, wherein the substrate is a medical device selected from the group consisting of a cardiovascular device, an artificial blood vessel, an artificial bone joint, a scaffold that supports tissue growth, a biosensor, and a percutaneous device.

23. A surface which is a material selected from the group consisting of a metal, glass, a silicon containing material, iron oxide, titanium oxide and silicon oxide, comprising a plurality of cross-linked, distinctly-formed layers, the plurality of cross-linked, distinctly-formed layers comprising at least three layers wherein the at least three layers comprise a first water soluble polymer layer, a second protein layer, and a third water soluble polymer layer, wherein the first water soluble polymer layer comprises a water soluble polymer that comprises a reactive group selected from the group consisting of sulfones, sulfoxides, sulfonates, sulfonamides, phosphonates and phosphonamides;

the second protein layer comprises at least one protein that comprises at least one lipid binding site and at least one functional group selected from the group consisting of an amino group and a sulfhydryl group; and the third water soluble polymer layer comprises a reactive group selected from the group consisting of sulfones, sulfoxides, sulfonates, sulfonamides, phosphonates and phosphonamides; and whereby the second protein layer is disposed between the first water soluble polymer layer and the third water soluble polymer layer to cross-link the first water soluble polymer layer and the third water soluble polymer layer together to form the plurality of cross-linked, distinctly-formed layers.

24. The surface of claim 23, wherein the surface is a material selected from the group consisting of silver, gold, stainless steel, titanium, cadmium, palladium, platinum, iron, nickel, cobalt, and copper.

25. The surface of claim 23, wherein the layer thickness is from about 1 nm to 100 μm.

26. The surface of claim 23, wherein the water soluble polymer is selected from the group consisting of a hydrophilic polymer, a cellulose derivative, a polysaccharide, and a poly(amino acid).

27. The surface of claim 23, wherein the protein is albumin or a high density lipoprotein particle comprising Apo A-I and lipids.

28. The surface of claim 23, wherein the protein has from about 2 to about 7 lipid binding sites.

29. The surface of claim 23, wherein the protein is a lipoprotein selected from the group consisting of chylomicrons, very low density lipoproteins, intermediate density lipoproteins, low density lipoproteins, and high density lipoproteins.

30. The surface of claim 23, wherein the water soluble polymer is polyethylene glycol.

31. The surface of claim 23, further comprising a therapeutic molecule conjugated to the protein.

32. The surface of claim 23, wherein the surface further comprises a therapeutic molecule that converts an endogenous precursor form of a molecule to the active form of an endogenous molecule in a subject.

33. The surface of claim 32, wherein the therapeutic molecule is an enzyme.

34. The surface of claim 33, wherein the enzyme is a recombinant enzyme having an added GST tag.

35. The surface of claim 32, wherein the enzyme is sphingosine kinase.

36. The surface of claim 33, wherein the sphingosine kinase has an amino acid sequence encoded by a nucleic acid sequence selected from the group consisting of SEQ ID NO:1 and SEQ ID NO:2.

37. The surface of claim 23, wherein the surface further comprises a polypeptide that promotes adhesion of cells.

38. The surface of claim 37, wherein the polypeptide comprises the amino acid sequence RGD.

39. The surface of claim 23, wherein the protein is a recombinant protein having the amino acid sequence of a native protein, further comprising amino acid residues that react with the water soluble polymer to form cross-links between the protein layers and the water soluble polymer layers.

40. The surface of claim 39, wherein the added amino acid residue is cysteine.

41. The surface of claim 39, wherein the recombinant protein has an amino acid sequence encoded by a nucleic acid sequence comprising SEQ ID NO:3 or SEQ ID NO:4.

42. The surface of claim 23, wherein the surface is from about 90 percent to about 99 percent protein rejecting.

43. The surface of claim 23, where the surface has from about 4 to about 50 distinctly-formed layers.

44. The surface of claim 23, wherein the surface is a medical device selected from the group consisting of a vascular graft, a cardiovascular device, an artificial blood vessel, an artificial bone joint, a scaffold that support tissue growth, a biosensor, and a percutaneous device.

* * * * *